(12) United States Patent
Jung et al.

(10) Patent No.: US 10,003,029 B2
(45) Date of Patent: Jun. 19, 2018

(54) COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventors: Hyejin Jung, Yongin-si (KR);
Youngkook Kim, Yongin-si (KR);
Seokhwan Hwang, Yongin-si (KR);
Kwanghyun Kim, Yongin-si (KR);
Sanghyun Han, Yongin-si (KR);
Miehwa Park, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 94 days.

(21) Appl. No.: 15/140,342

(22) Filed: Apr. 27, 2016

(65) Prior Publication Data
US 2017/0012205 A1  Jan. 12, 2017

(30) Foreign Application Priority Data
Jul. 7, 2015  (KR) .................. 10-2015-0096778

(51) Int. Cl.

| | |
|---|---|
| *H01L 51/00* | (2006.01) |
| *C07C 211/54* | (2006.01) |
| *C07D 307/91* | (2006.01) |
| *C07D 209/86* | (2006.01) |
| *C07D 209/88* | (2006.01) |
| *C07C 211/61* | (2006.01) |
| *C07F 7/08* | (2006.01) |
| *C07D 405/12* | (2006.01) |
| *C07D 405/04* | (2006.01) |
| *C07D 213/38* | (2006.01) |
| *C07D 209/80* | (2006.01) |
| *H01L 51/50* | (2006.01) |

(52) U.S. Cl.
CPC .......... *H01L 51/006* (2013.01); *C07C 211/54* (2013.01); *C07C 211/61* (2013.01); *C07D 209/80* (2013.01); *C07D 209/86* (2013.01); *C07D 209/88* (2013.01); *C07D 213/38* (2013.01); *C07D 307/91* (2013.01); *C07D 405/04* (2013.01); *C07D 405/12* (2013.01); *C07F 7/0818* (2013.01); *H01L 51/0061* (2013.01); *C07C 2603/18* (2017.05); *C07C 2603/26* (2017.05); *C07C 2603/40* (2017.05); *C07F 7/0812* (2013.01); *H01L 51/001* (2013.01); *H01L 51/0003* (2013.01); *H01L 51/0056* (2013.01); *H01L 51/0058* (2013.01); *H01L 51/0067* (2013.01); *H01L 51/0072* (2013.01); *H01L 51/0073* (2013.01); *H01L 51/506* (2013.01); *H01L 2251/308* (2013.01)

(58) Field of Classification Search
CPC ........................ C07C 211/54; C07D 307/91
See application file for complete search history.

(56) References Cited

U.S. PATENT DOCUMENTS

| | | | |
|---|---|---|---|
| 2006/0100433 A1 | 5/2006 | Yamaguchi et al. |
| 2009/0085468 A1 | 4/2009 | Funahashi et al. |
| 2014/0239279 A1 | 8/2014 | Park et al. |

FOREIGN PATENT DOCUMENTS

| | | |
|---|---|---|
| KR | 10-2008-0068862 A | 7/2008 |
| KR | 10-2013-0094171 A | 8/2013 |
| KR | 10-2014-0108117 A | 9/2014 |
| WO | WO 2014/072017 A1 | 5/2014 |

OTHER PUBLICATIONS

Tai et al. Organic Electronics 16 (2015) 54-70.*

* cited by examiner

*Primary Examiner* — Kuo Liang Peng
(74) *Attorney, Agent, or Firm* — Lewis Roca Rothgerber Christie LLP

(57) ABSTRACT

An organic light-emitting device includes a first electrode; a second electrode facing the first electrode; and an organic emission layer between the first electrode and the second electrode. The organic emission layer may include a compound represented by Formula 1:

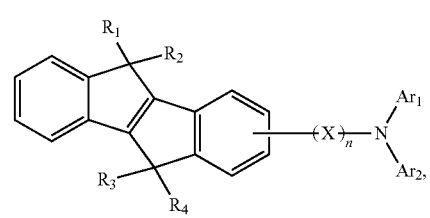

Formula 1 wherein Formula 1 contains an indenoindenyl moiety. The compound may increase hole mobility in the device when used as a hole transport and/or hole injection material, thereby improving its lifetime, current, voltage, and luminescent characteristics.

20 Claims, 1 Drawing Sheet

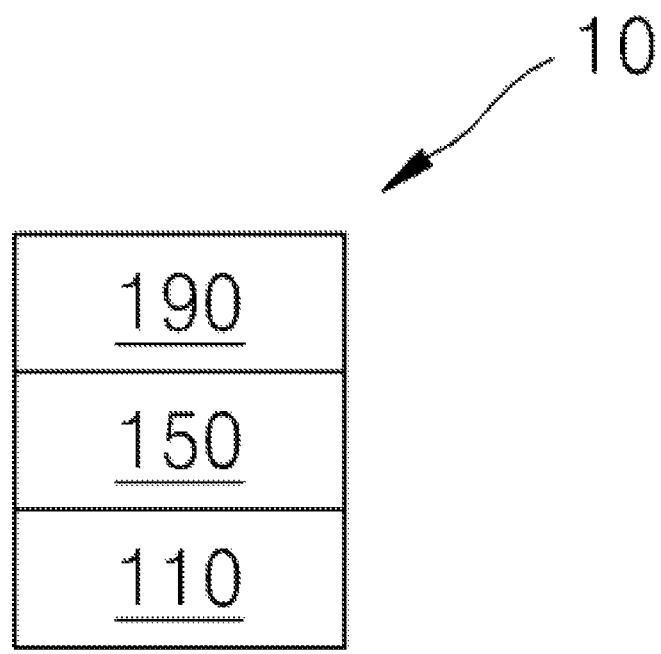

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0096778, filed on Jul. 7, 2015, in the Korean Intellectual Property Office, the entire content of which is incorporated herein by reference.

BACKGROUND

1. Field

One or more aspects of example embodiments of the present disclosure relate to a compound and an organic light-emitting device including the same.

2. Description of the Related Art

Organic light-emitting devices (OLEDs) are self-emission devices that have wide viewing angles, high contrast ratios, and/or short response times. In addition, OLEDs exhibit excellent luminance, driving voltage, and/or response speed characteristics, and may produce full-color images.

An organic light-emitting device may include a first electrode on a substrate, and a hole transport region, an emission layer, an electron transport region, and a second electrode sequentially positioned on the first electrode. Holes provided from the first electrode may move toward the emission layer through the hole transport region, and electrons provided from the second electrode may move toward the emission layer through the electron transport region. The holes and the electrons may recombine in the emission layer to produce excitons. These excitons may change from an excited state to a ground state to thereby generate light.

SUMMARY

One or more aspects of example embodiments of the present disclosure are directed toward a material for a hole transport region and an organic light-emitting device including the material.

Additional aspects will be set forth in part in the following description and, in part, will be apparent from the description, or may be learned by practice of the presented embodiments.

One or more example embodiments of the present disclosure provide a compound represented by Formula 1:

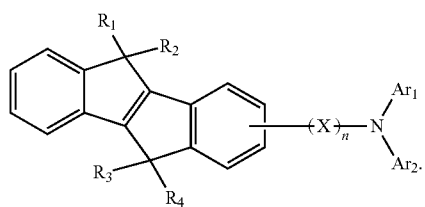

Formula 1

In Formula 1, $R_1$ to $R_4$ may each independently be selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $Ar_1$ and $Ar_2$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

X may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, n may be an integer selected from 0 to 5, and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, substituted $C_6$-$C_{60}$ arylene group, substituted $C_1$-$C_{60}$ heteroarylene group, substituted divalent non-aromatic condensed polycyclic group, and substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more example embodiments of the present disclosure, an organic light-emitting device includes a first electrode; a second electrode facing the first electrode; and an organic layer between the first electrode and the second electrode that includes an emission layer, wherein the organic layer includes the compound represented by Formula 1.

According to one or more example embodiments, a flat display device includes the organic light-emitting device, in which a first electrode is electrically connected to a source electrode or a drain electrode of a thin film transistor.

BRIEF DESCRIPTION OF THE DRAWING

These and/or other aspects will become apparent and more readily appreciated from the following description of the example embodiments, taken in conjunction with the accompanying drawing, which illustrates a schematic view of an organic light-emitting device according to one or more embodiments of the present disclosure.

DETAILED DESCRIPTION

Reference will now be made to example embodiments illustrated in the accompanying drawings, wherein like reference numerals refer to like elements throughout and duplicative descriptions thereof may not be provided. In this regard, the present example embodiments may have different forms and should not be construed as being limited to the descriptions set forth herein. Accordingly, the example embodiments are merely described below, by referring to the drawing, to explain aspects of the present description. As used herein, the term "and/or" includes any and all combinations of one or more of the associated listed items. Expressions such as "at least one of", "one of", and "selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

According to an example embodiment of the present disclosure, a compound is represented by Formula 1:

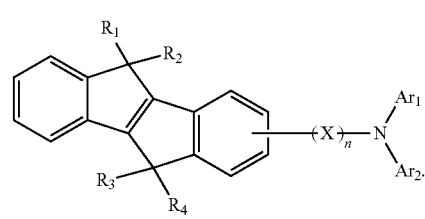

Formula 1

In Formula 1, $R_1$ to $R_4$ may each independently be selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $Ar_1$ and $Ar_2$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, X may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, n may be an integer selected from 0 to 5, and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, substituted $C_6$-$C_{60}$ arylene group, substituted $C_1$-$C_{60}$ heteroarylene group, substituted divalent non-aromatic condensed polycyclic group, and substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$) (e.g., a substituted amino group), —Si($Q_{13}$)($Q_{14}$)($Q_{15}$) (e.g., a substituted silyl group), and —B($Q_{16}$)($Q_{17}$) (e.g., a substituted boryl group);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$) (e.g., a substituted amino group), —Si($Q_{23}$)($Q_{24}$)($Q_{25}$) (e.g., a substituted silyl group), and —B($Q_{26}$)($Q_{27}$) (e.g., a substituted boryl group), and $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Various types (e.g., structures) of arylamine compounds have been reported and practically used as hole injection and/or hole transport layer materials in organic light-emitting devices in the related art.

Non-limiting examples of the hole injection and/or hole transport layer material may include an NPB compound, or in some embodiments, a compound including a biphenyl group.

An organic light-emitting device may be subject to excessive thermal stress during a deposition process, as well as various problems due to melting of the material during preparation. Thus the organic light-emitting device needs to be improved in these regards.

For example, a thermally resistant material that is not modified under a high temperature environment may be used. Also, the material may have improved driving characteristics in order to increase electrical power efficiency.

According to one or more embodiments of the present disclosure, a compound including an indenoindene moiety may enable increased mobility when used as a hole injection and/or hole transport layer material. Due to the high mobility of holes in the material, an organic light-emitting device having a high efficiency and long lifespan may be manufactured.

Substituents of Formula 1 will be described in more detail.

In some embodiments, in Formula 1, $R_1$ to $R_4$ may each independently be selected from a substituted or unsubstituted $C_1$-$C_{60}$ alkyl group, a substituted or unsubstituted $C_6$-$C_{60}$ aryl group, and a substituted or unsubstituted $C_1$-$C_{60}$ heteroaryl group.

In some embodiments, in Formula 1, adjacent substituents of $R_1$ to $R_4$ may link to each other and form a ring. For example, $R_1$ and $R_2$, or $R_3$ and $R_4$ may link to each other and form a spiro compound.

In some embodiments, in Formula 1, $Ar_1$ and $Ar_2$ may each independently be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 1, X may be at least one group selected from Formulae 2a and 2b:

2a

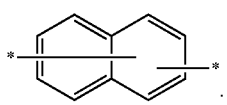
2b

In Formulae 2a and 2b, * may denote a binding site.

In some embodiments, in Formula 1, $Ar_1$ and $Ar_2$ may each independently be selected from the moieties of Formulae 3a to 3g:

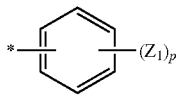
3a

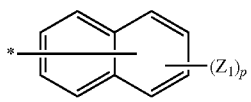
3b

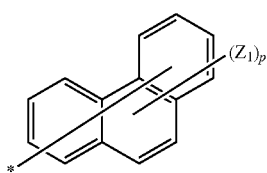
3c

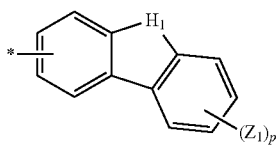
3d

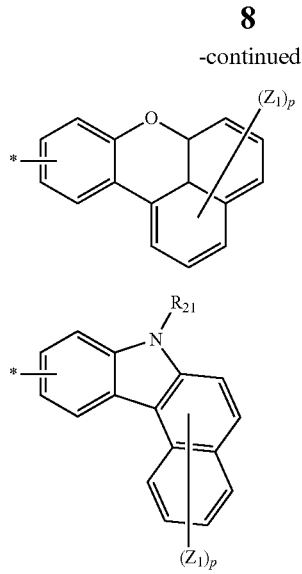
3e

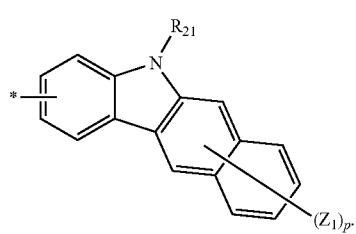
3f

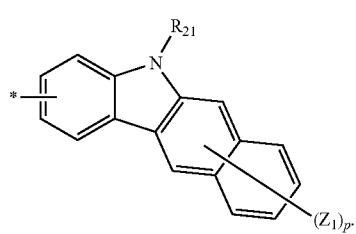
3g

In Formulae 3a to 3g, $H_1$ may denote oxygen (O), sulfur (S), $NR_{31}$, or $C(R_{32})(R_{33})$, $R_{31}$ to $R_{33}$, $R_{21}$, and $Z_1$ may each independently be selected from hydrogen, deuterium, a halogen, $Si(R_{41})(R_{42})(R_{43})$, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, $R_{41}$ to $R_{43}$ may each independently be selected from a substituted or $C_1$-$C_{20}$ alkyl group and a substituted or unsubstituted $C_6$-$C_{20}$ aryl group, p may denote an integer selected from 1 to 9, and

* may denote a binding site.

In some embodiments, $R_{32}$ and $R_{33}$ may link to each other and form a ring. For example, $R_{32}$ and $R_{33}$ may link to each other and form a spiro compound.

In some embodiments, in Formula 1, $R_1$ to $R_4$ may each independently be selected from the moieties of Formulae 4a to 4c:

4a

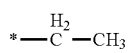
4b

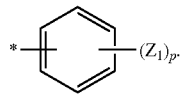
4c

In Formulae 4a to 4c, $Z_1$ may be selected from hydrogen, deuterium, a halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p may be an integer selected from 1 to 5, and

* may denote a binding site.

In some embodiments, the compound represented by Formula 1 may be a compound represented by Formula 2:

Formula 2

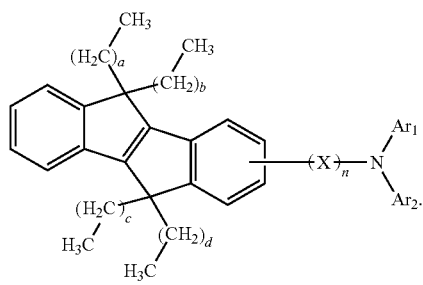

In Formula 2, a, b, c, and d may each independently be an integer selected from 0 and 1.

In some embodiments, the compound represented by Formula 1 may be a compound represented by Formula 3:

Formula 3

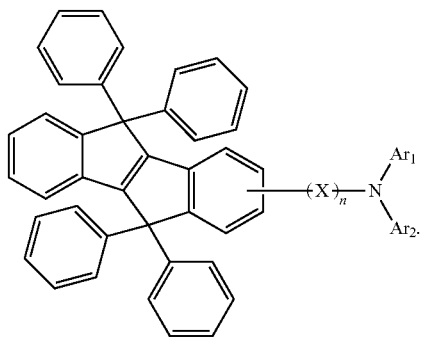

In some embodiments, the compound represented by Formula 1 may be a compound represented by Formula 4:

Formula 4

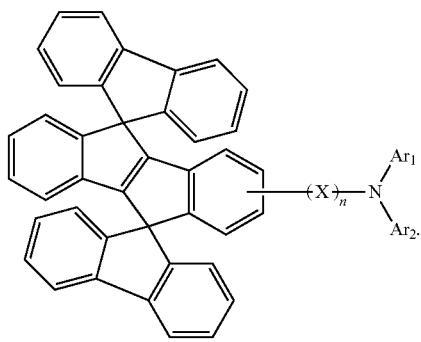

In some embodiments, the compound represented by Formula 1 may be selected from the compounds below:

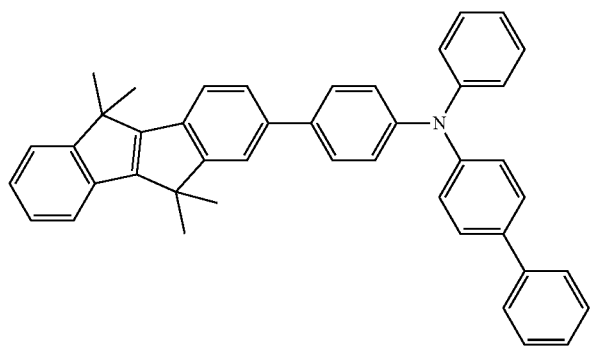

1

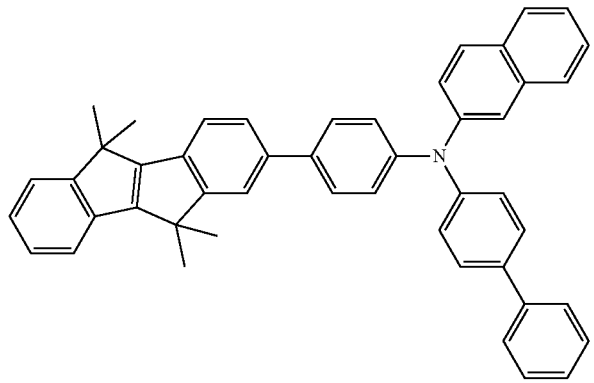

2

-continued
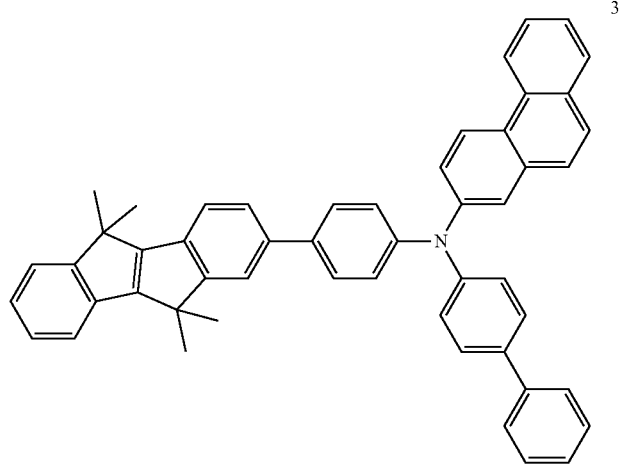
3
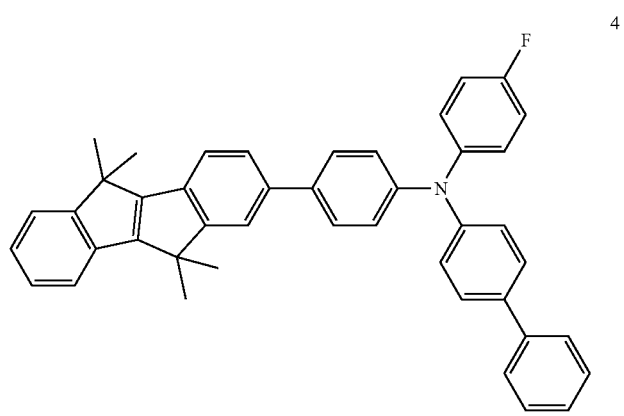
4
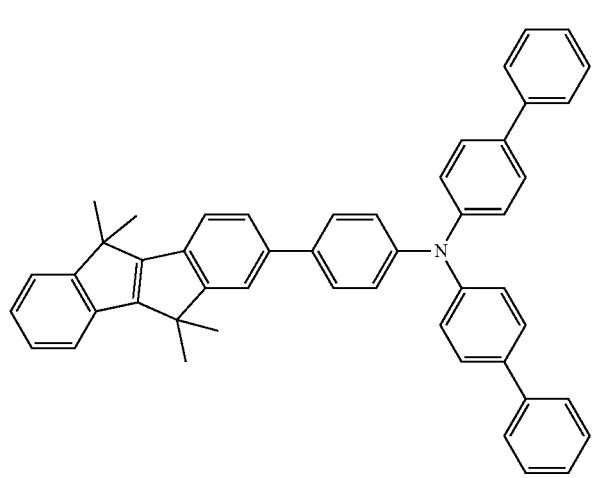
5

-continued
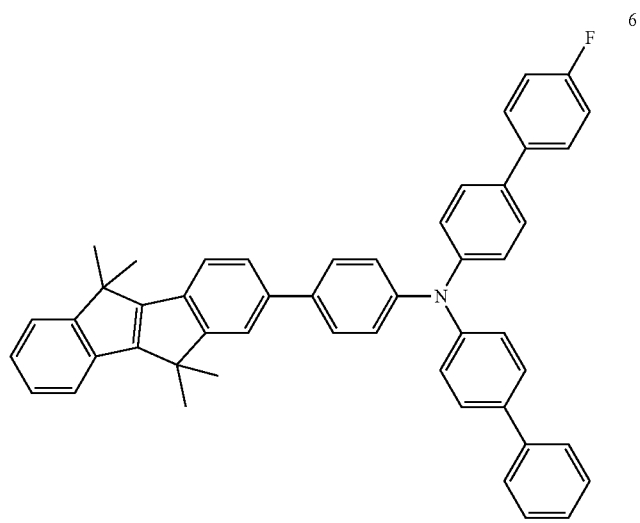
6
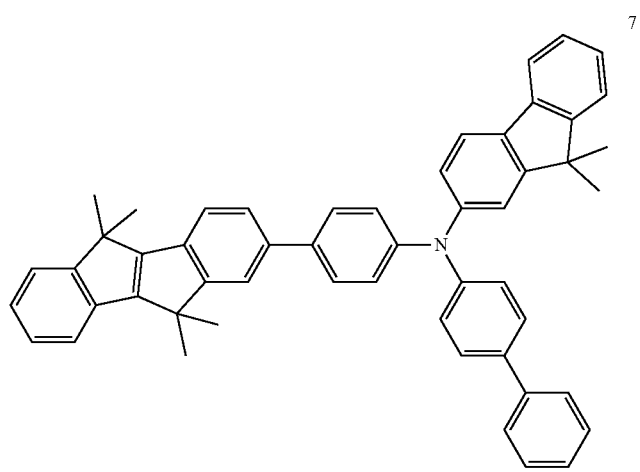
7
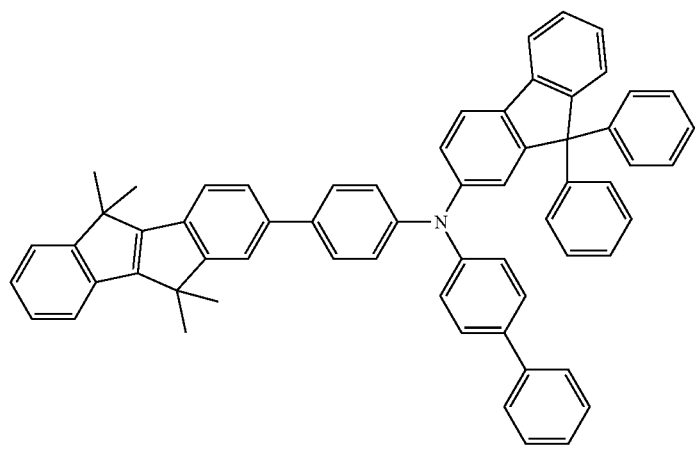
8

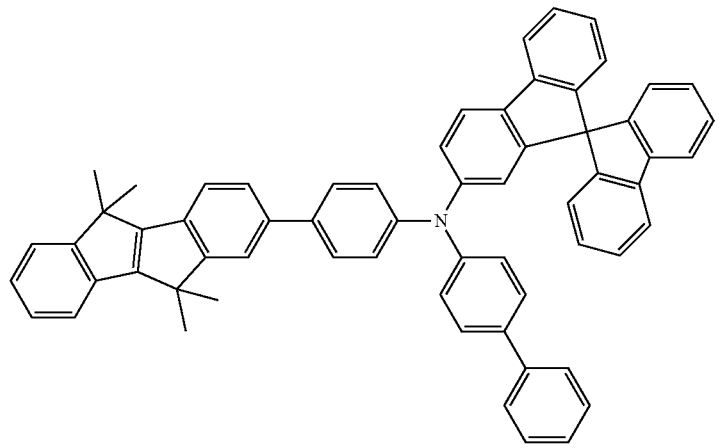
9
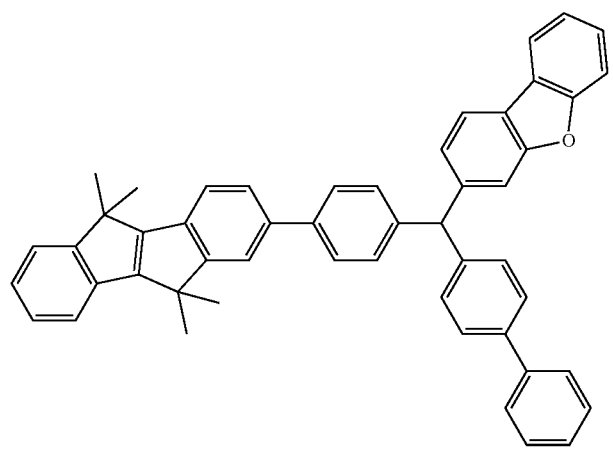
10
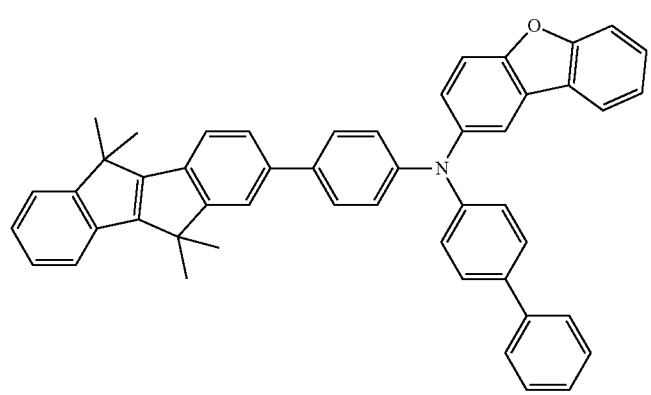
11

-continued
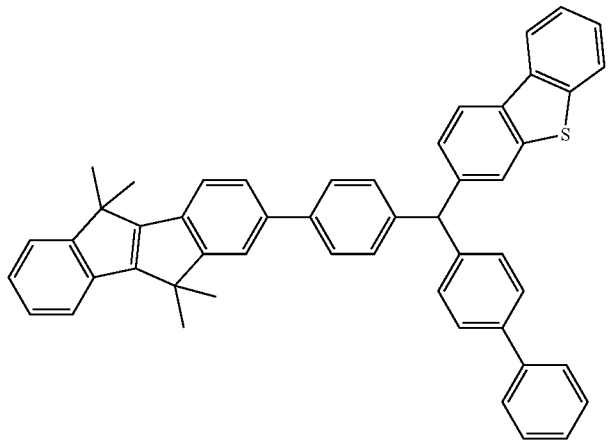
12
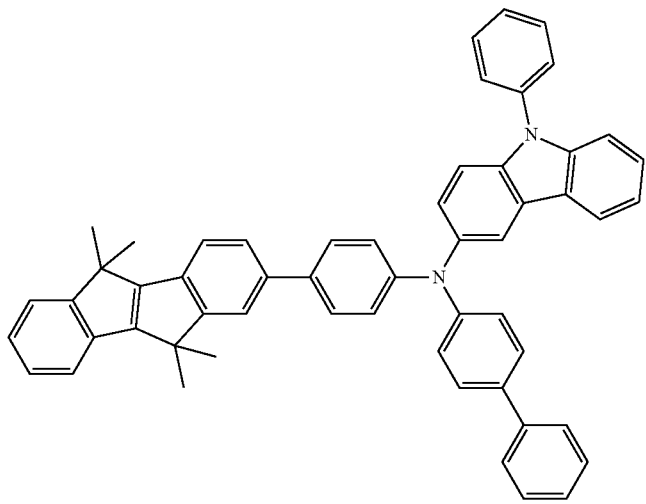
13
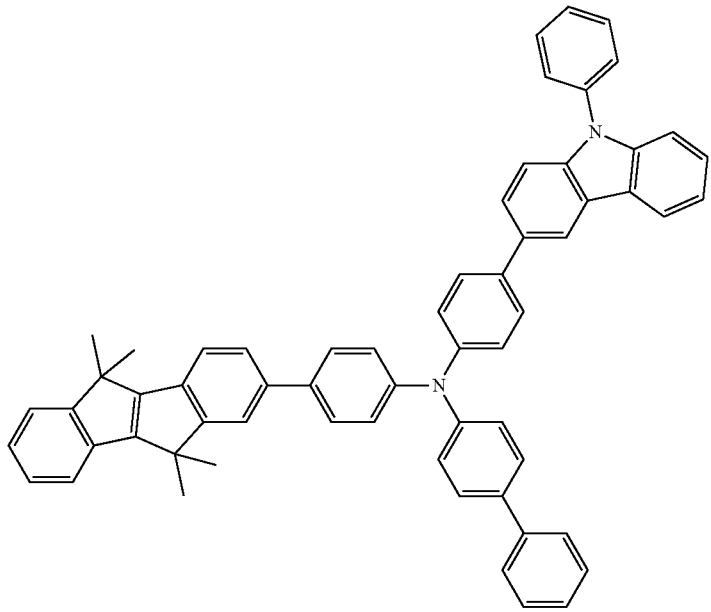
14

-continued
15
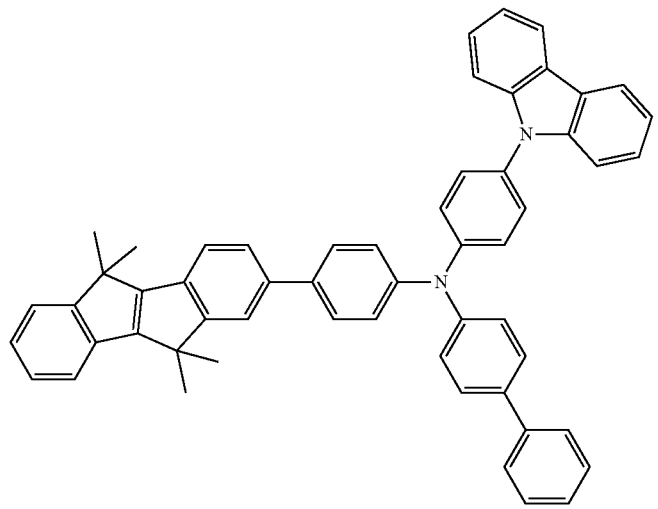
16
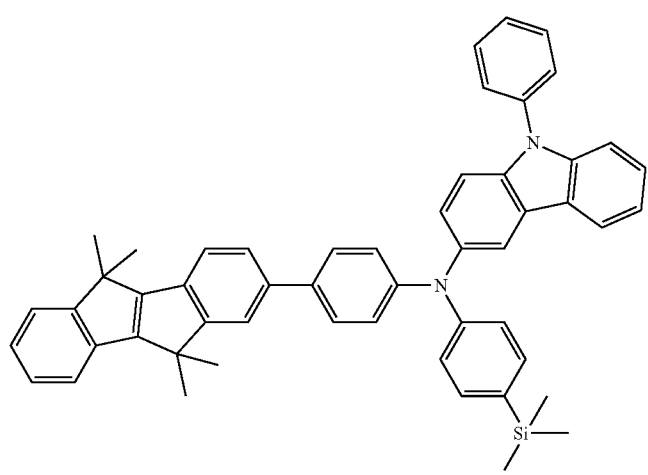
17
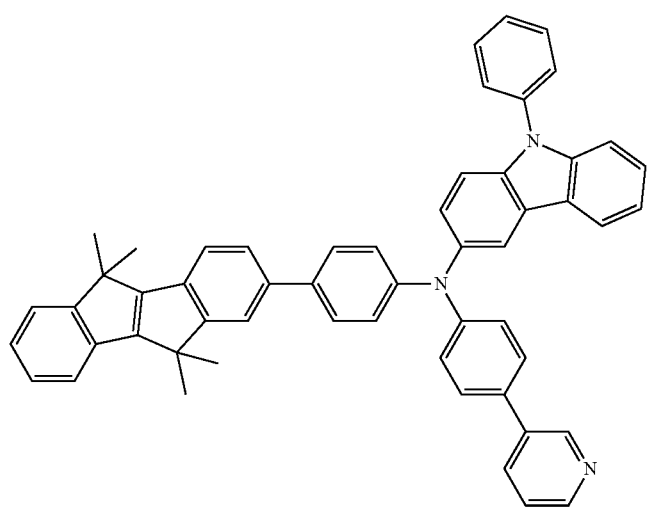

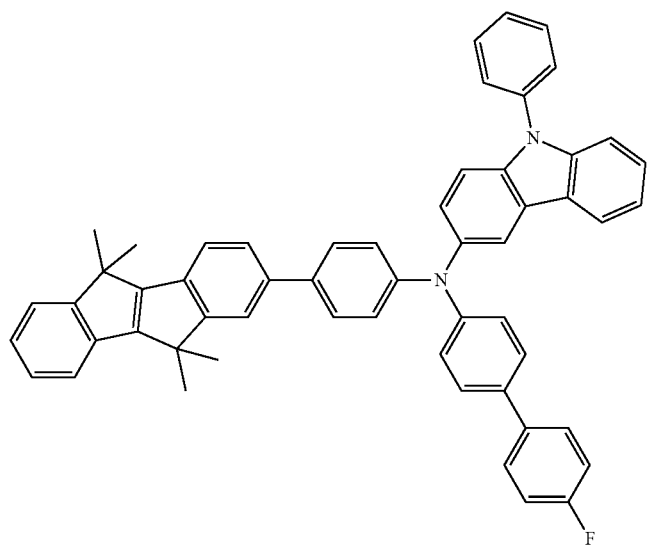
18
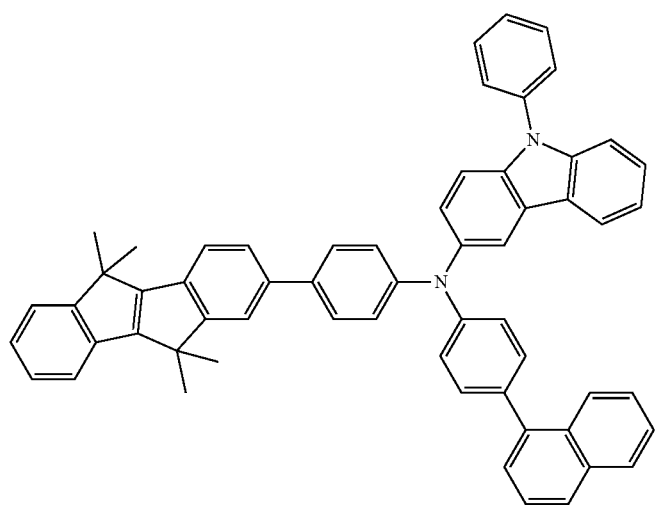
19
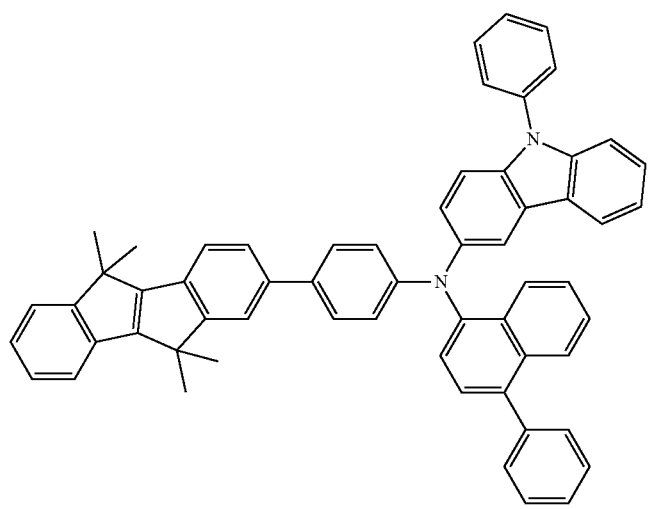
20

-continued
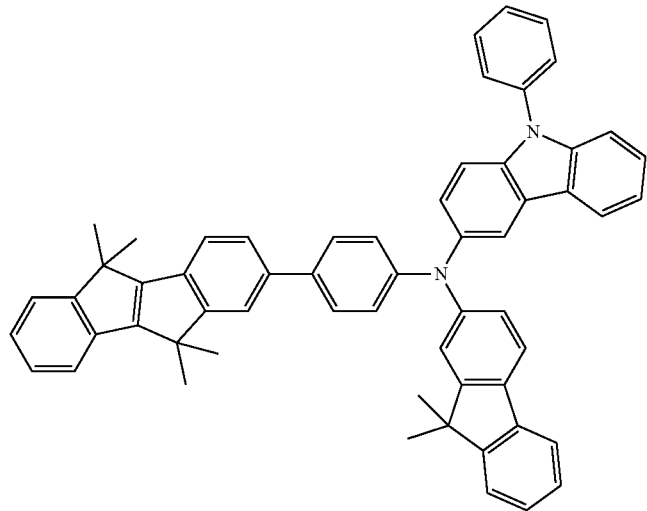
21
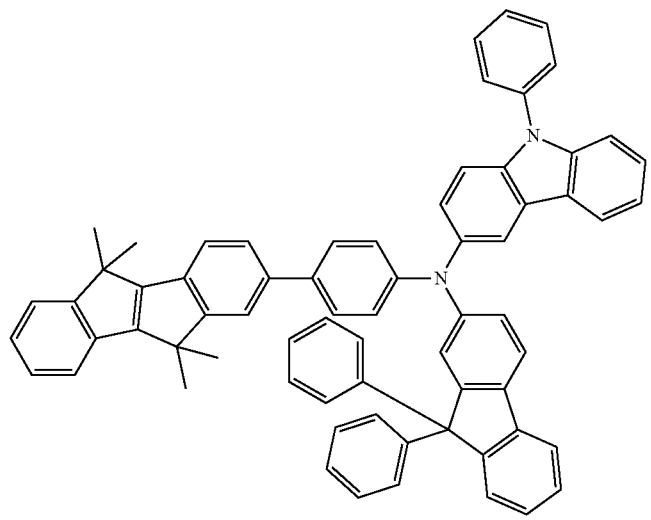
22
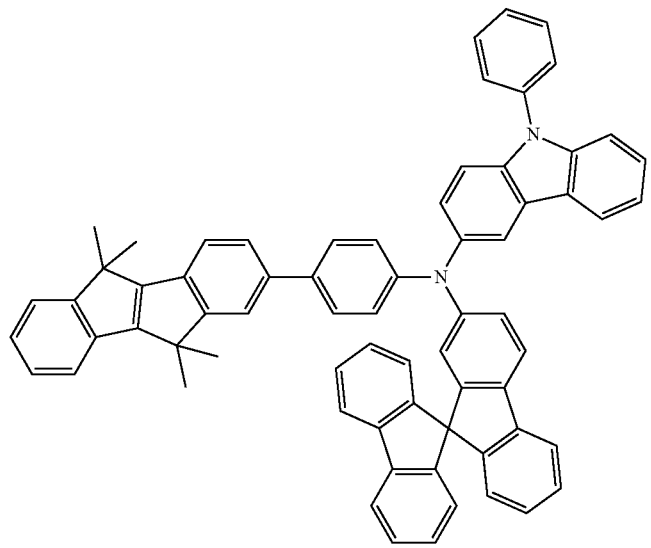
23

-continued
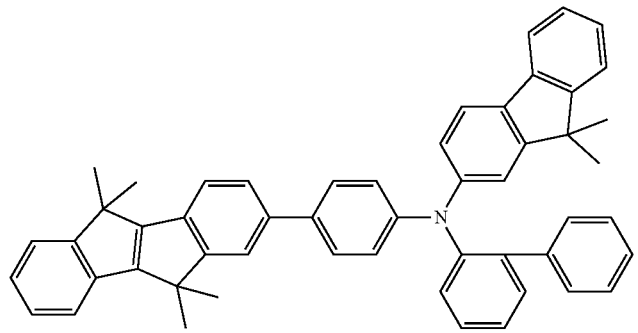
24
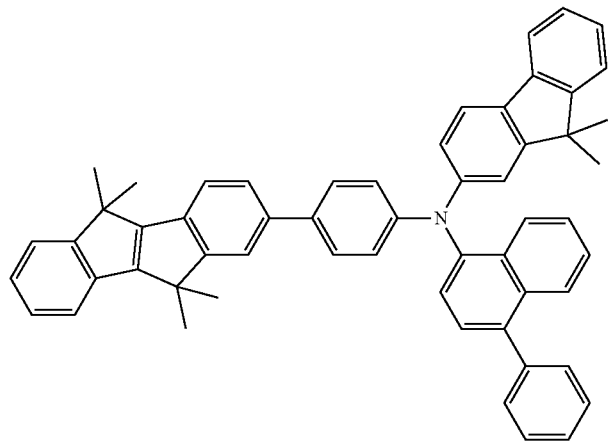
25
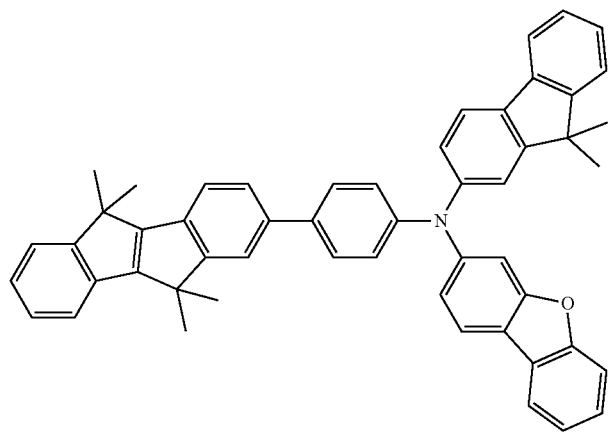
26
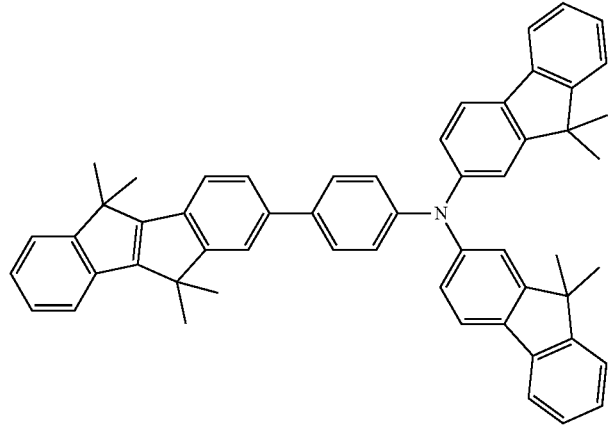
27

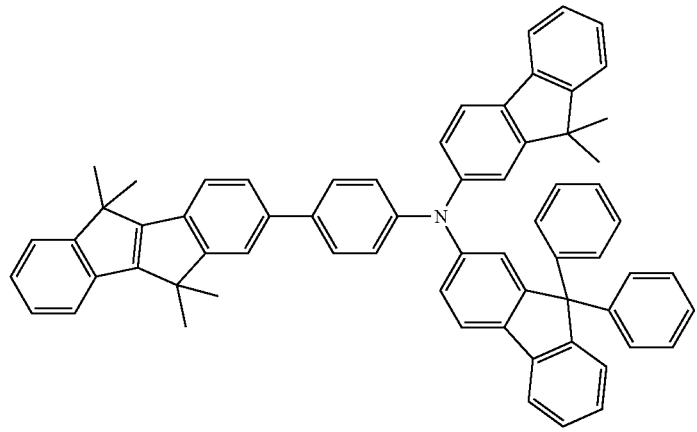
28
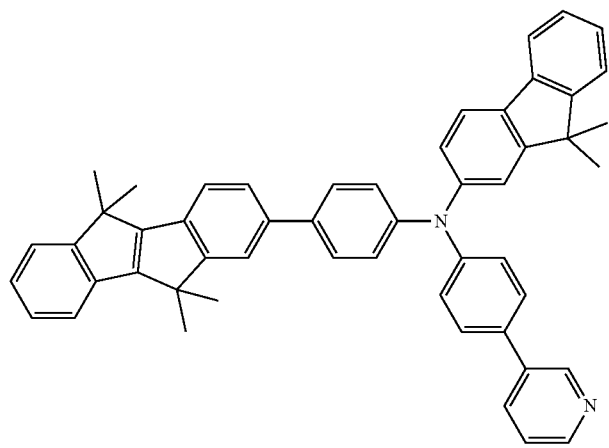
29
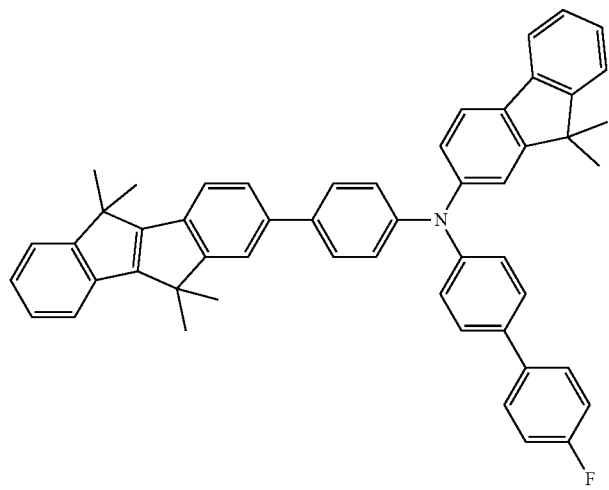
30

-continued
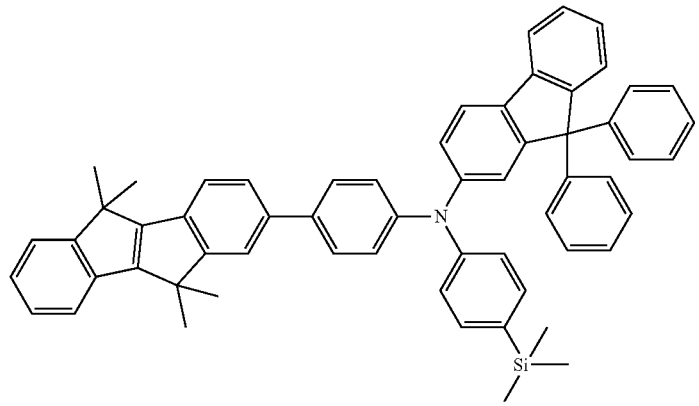
31
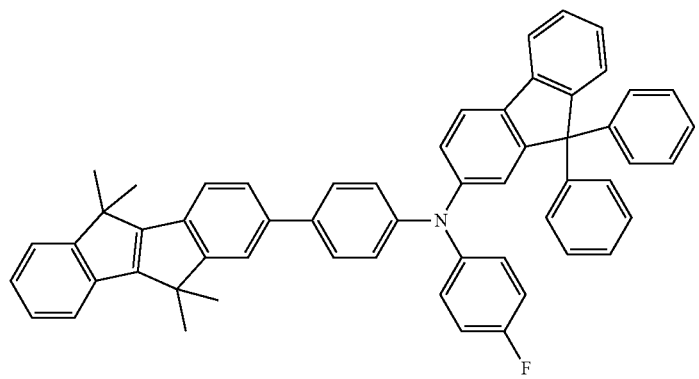
32
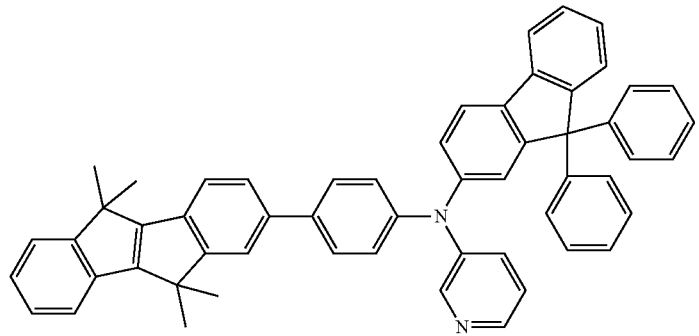
33
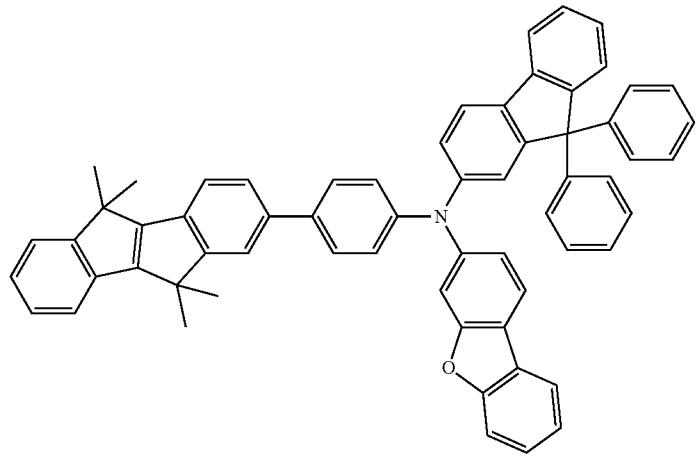
34

-continued
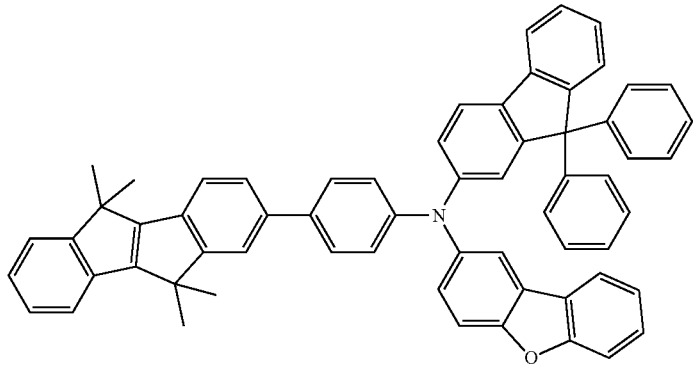
35
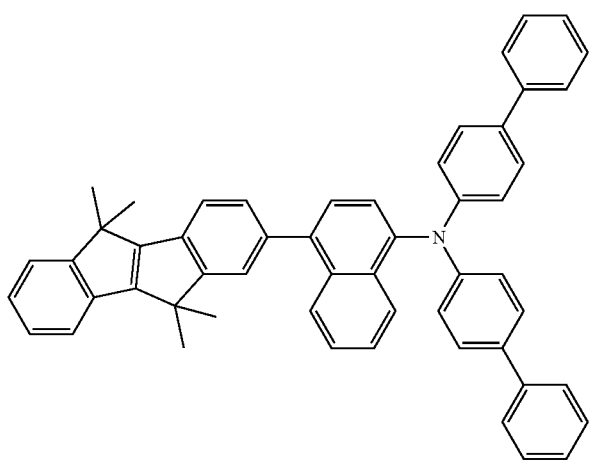
36
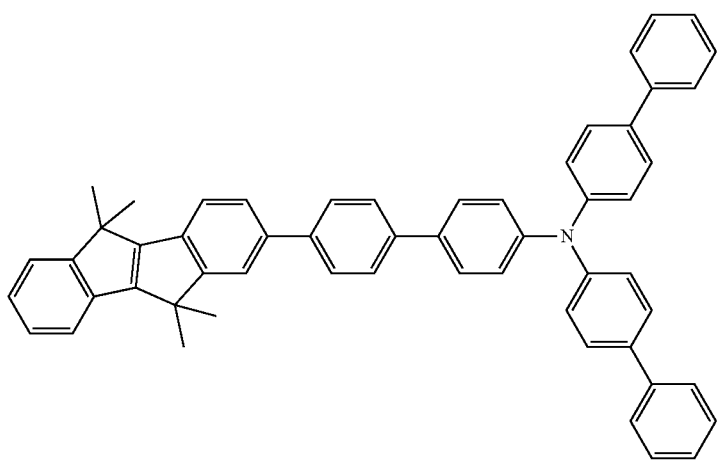
37

-continued
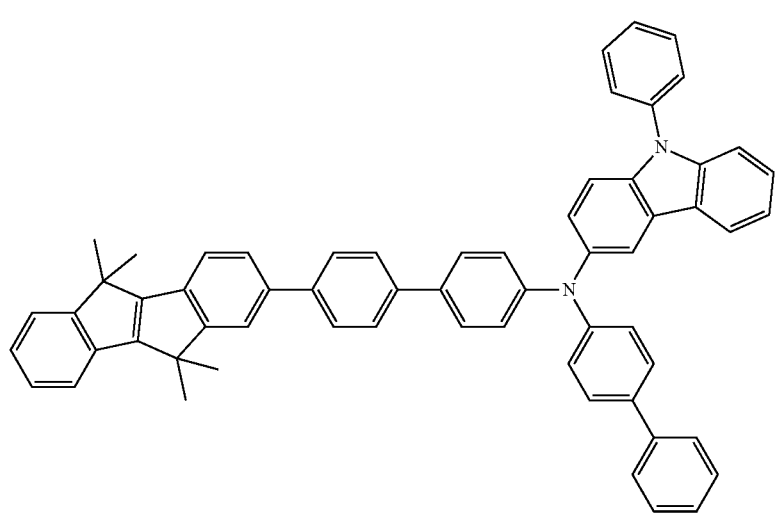
38
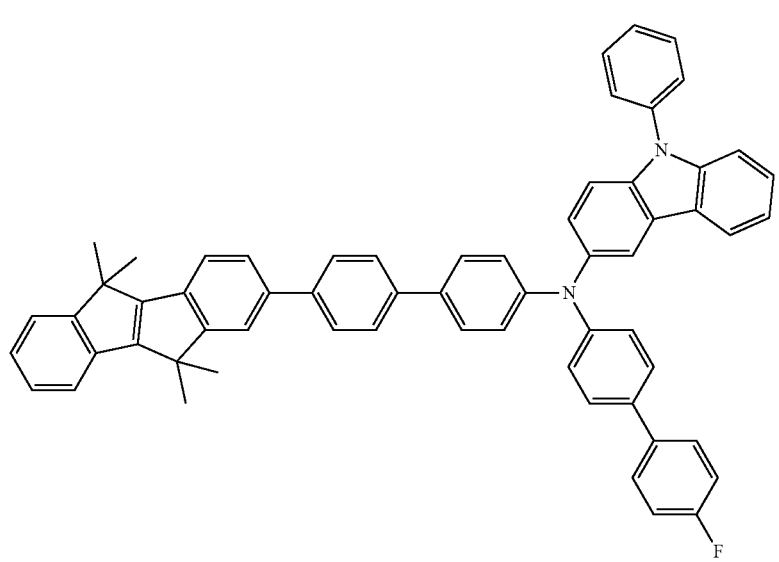
39
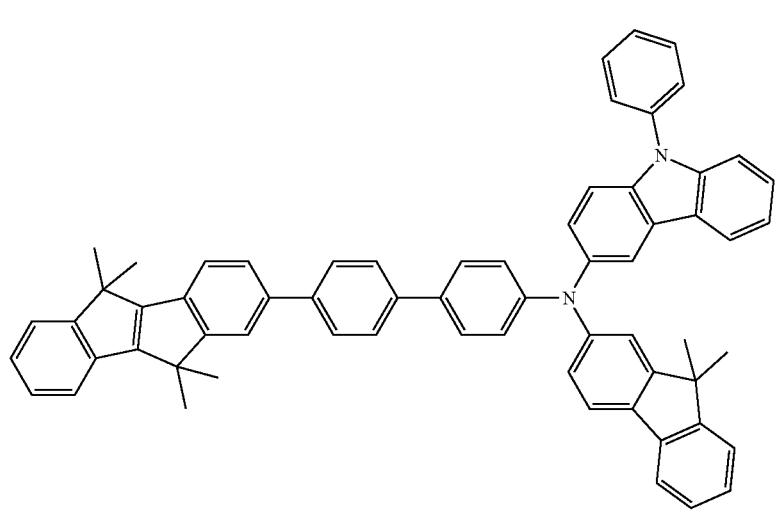
40

41
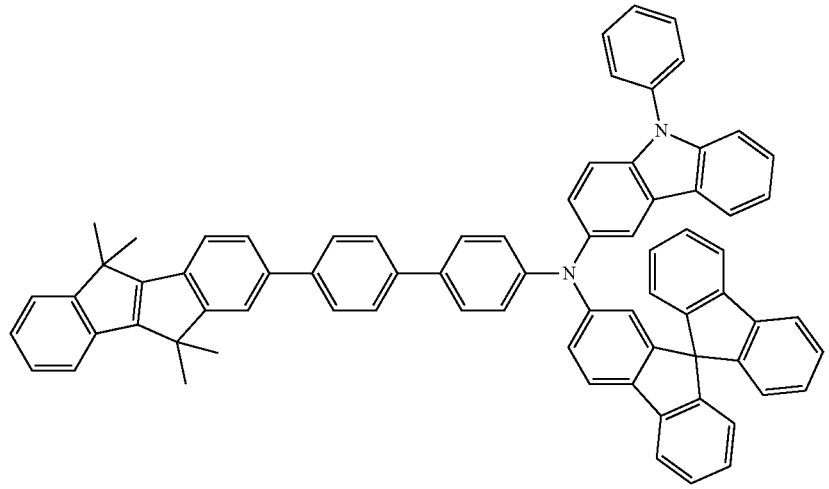
42
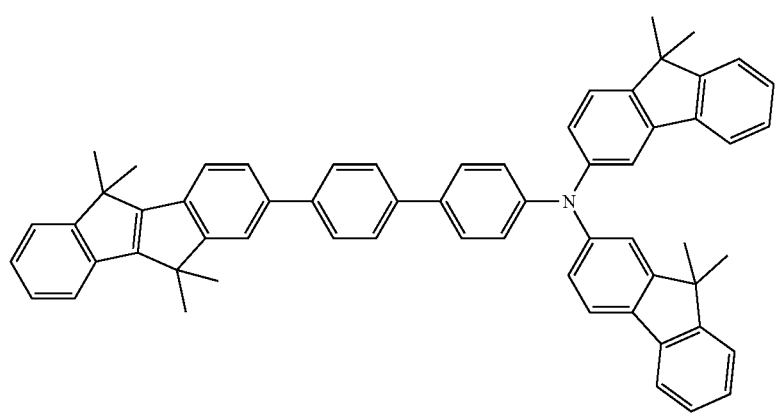
43
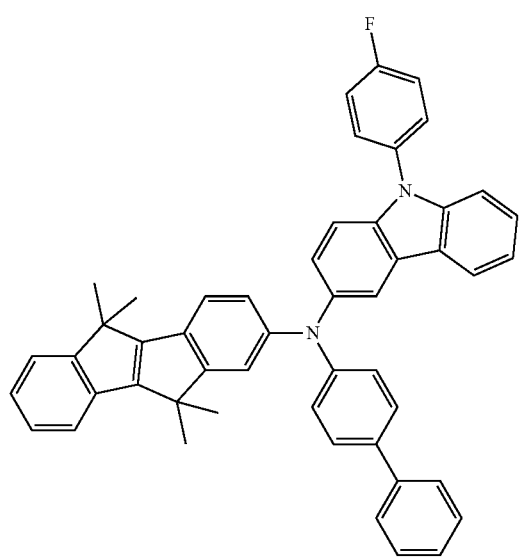

44
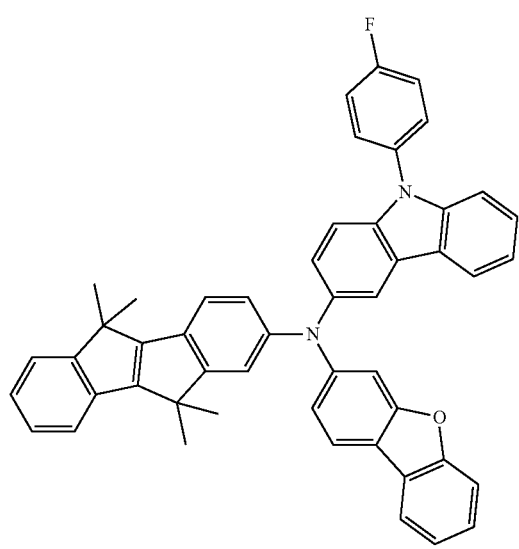
45
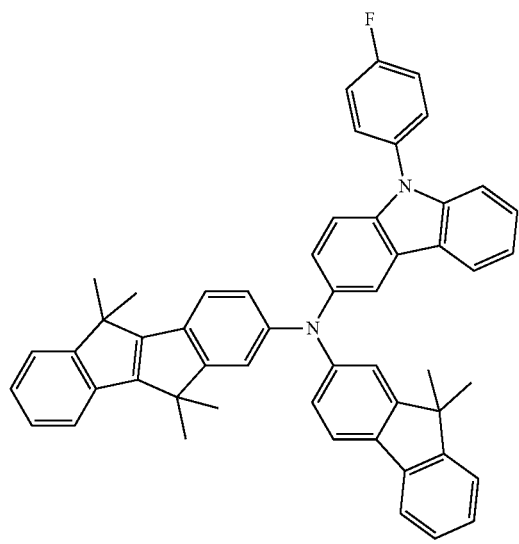
46
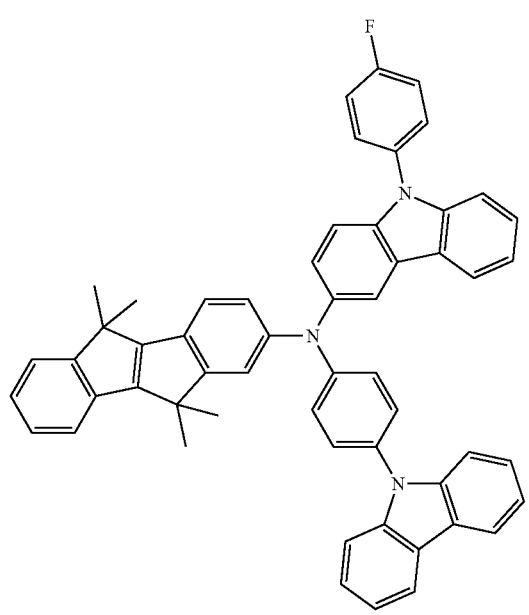

47
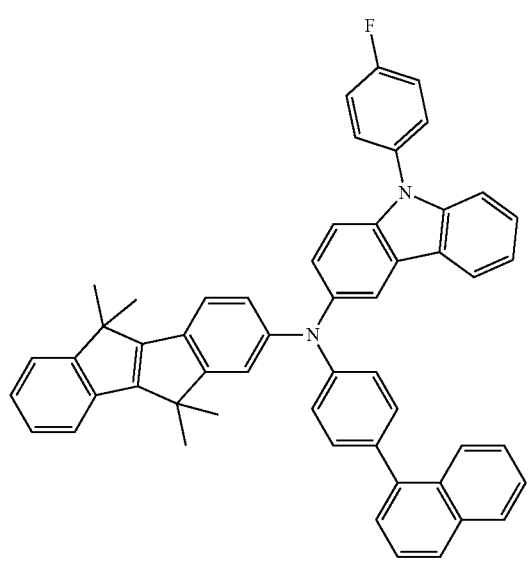
48
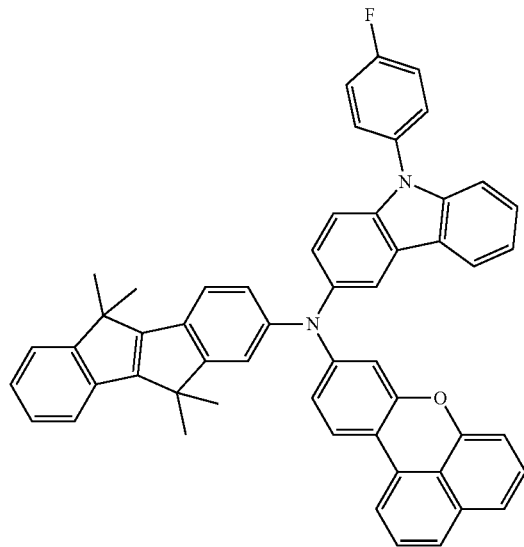
49
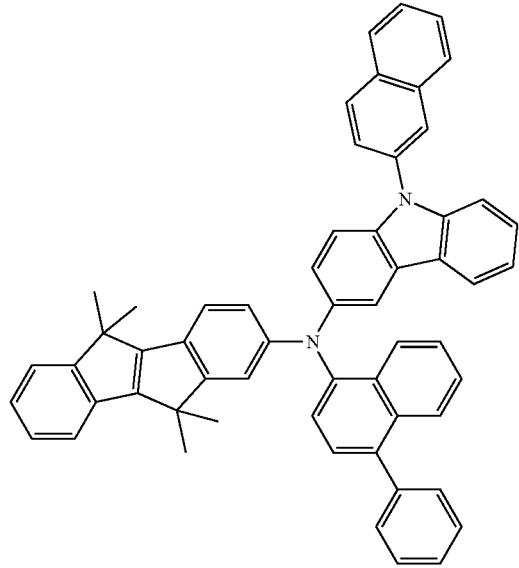

-continued
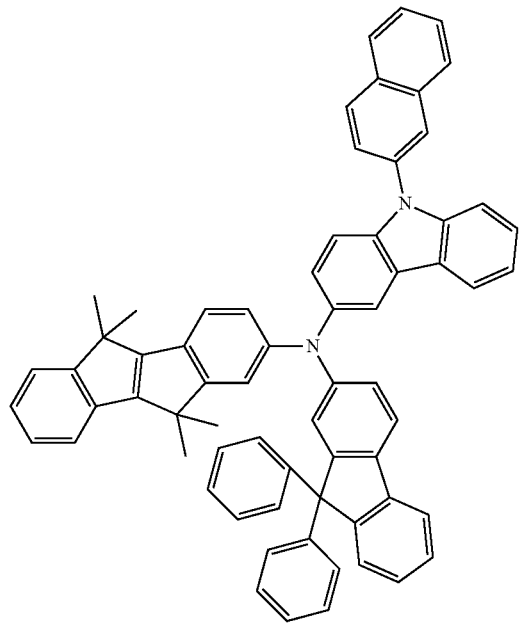
50
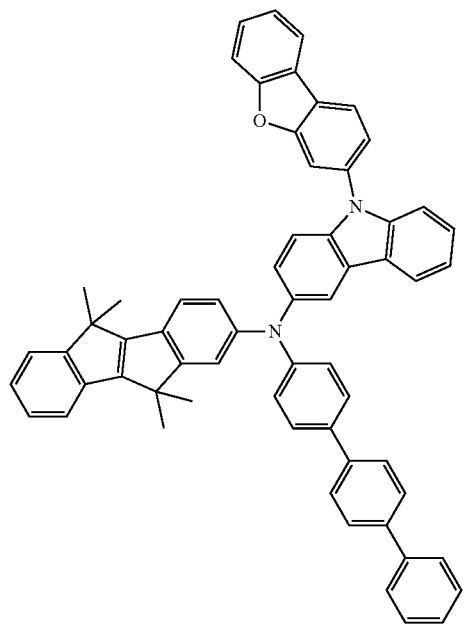
51

-continued
52
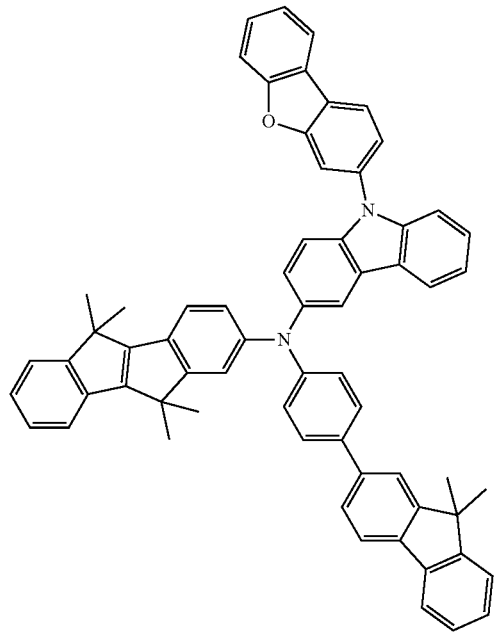
53
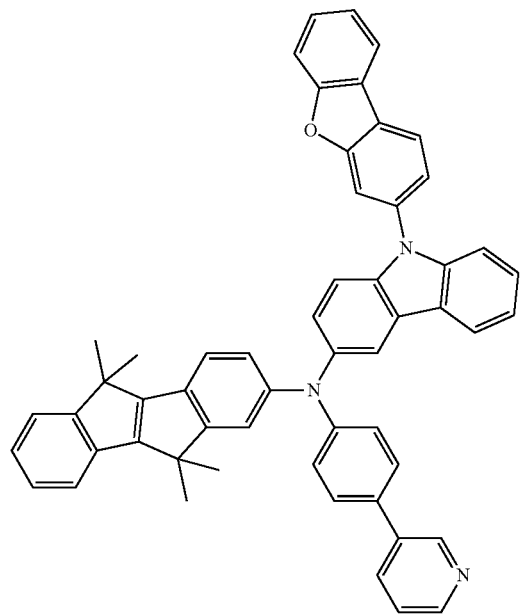

-continued
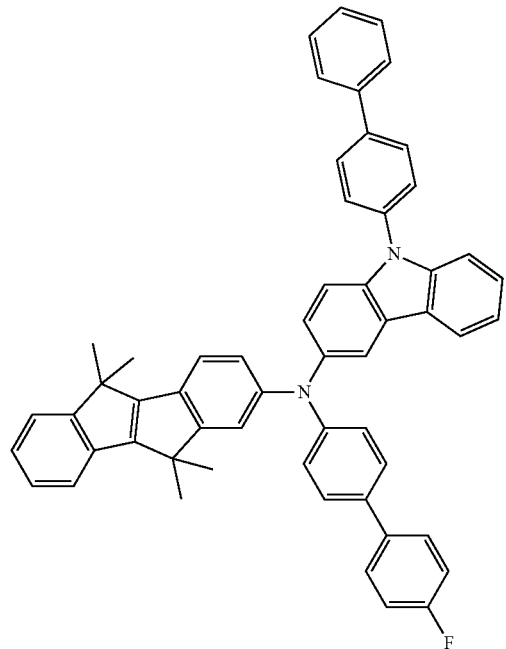
54
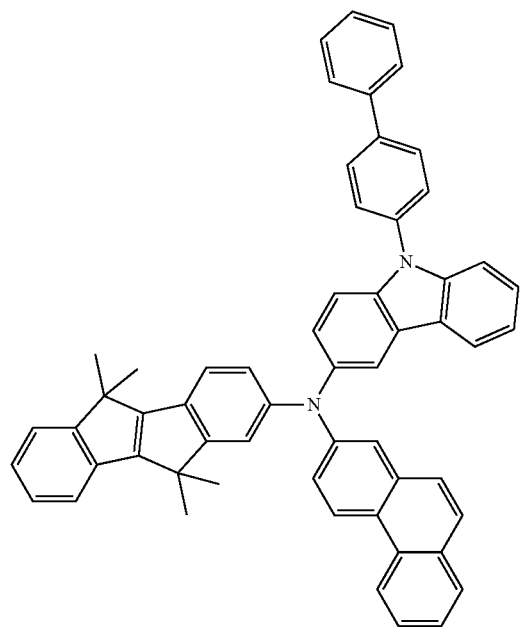
55

-continued
56
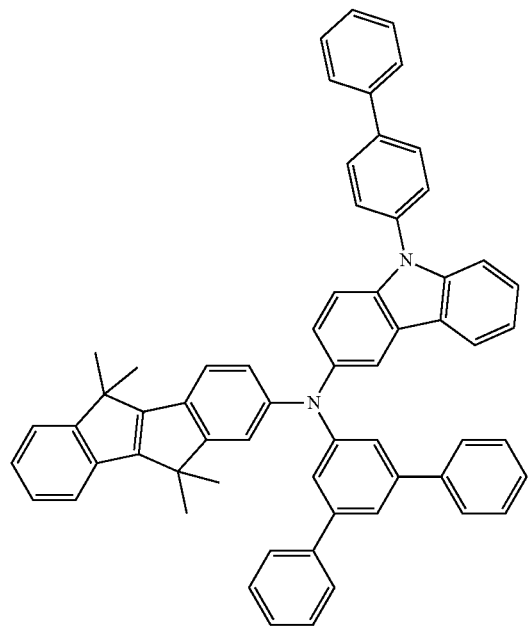
57
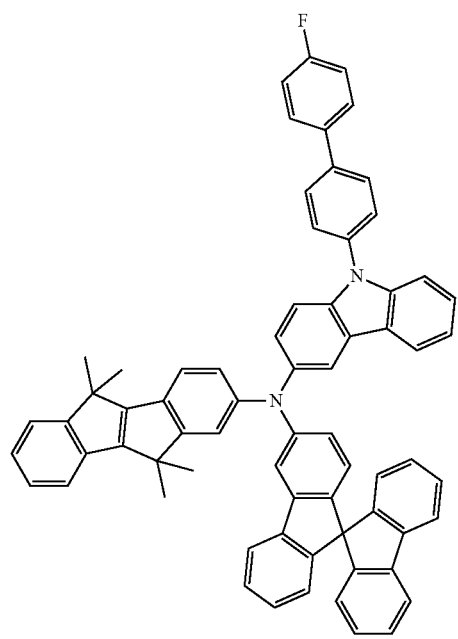
58
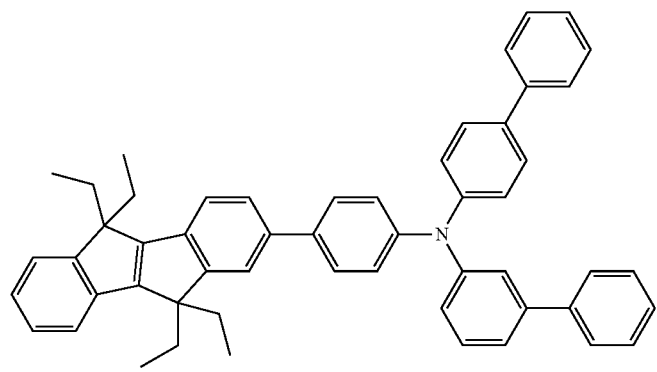

-continued
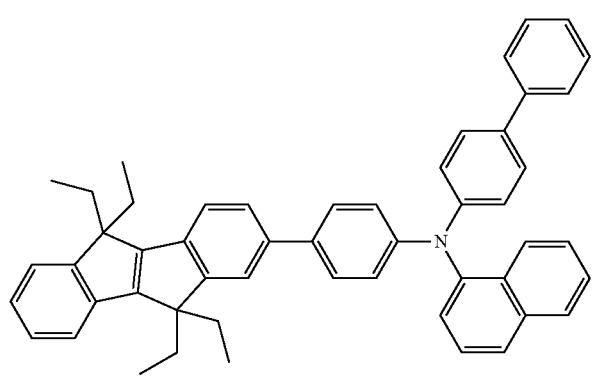
59
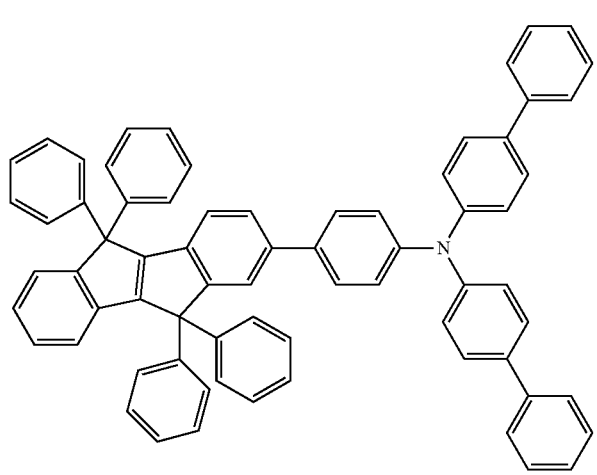
60
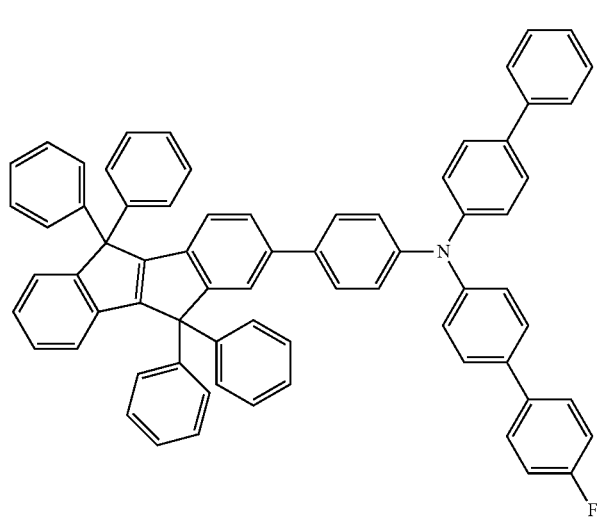
61

-continued
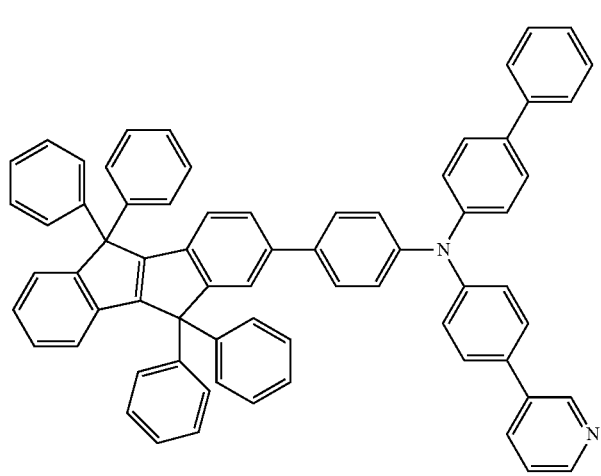
62
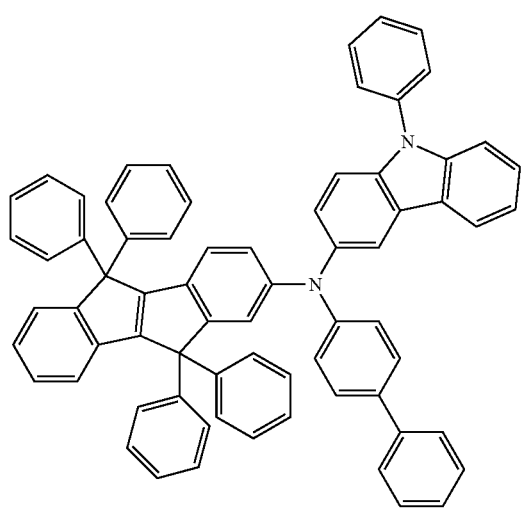
63
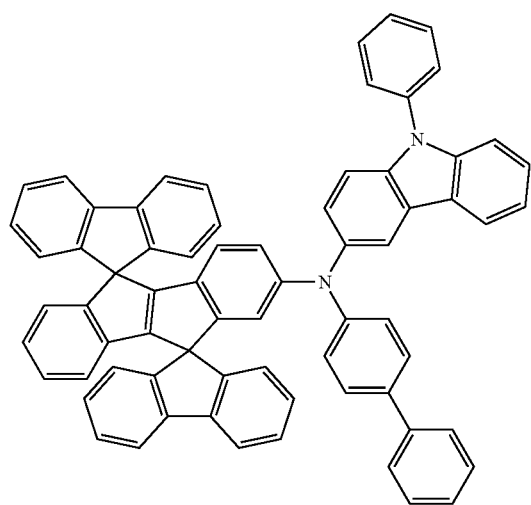
64

65
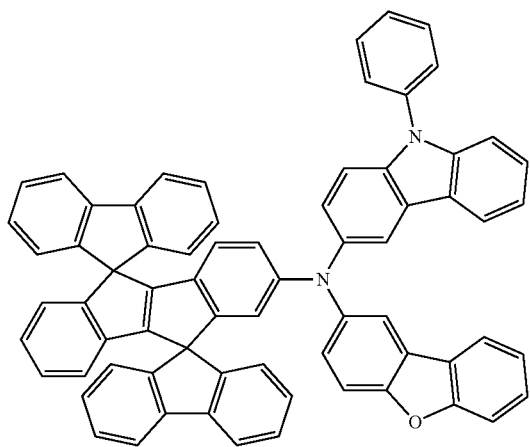
66
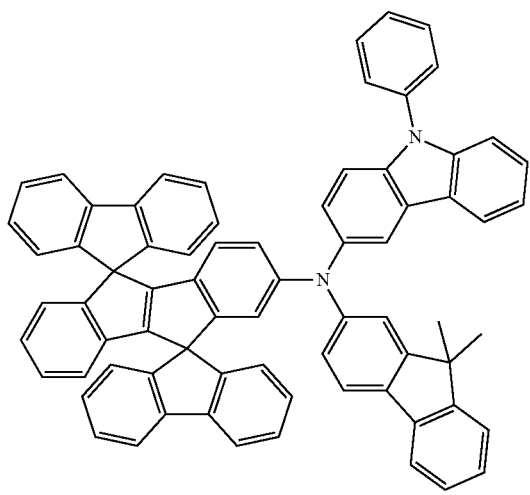
67
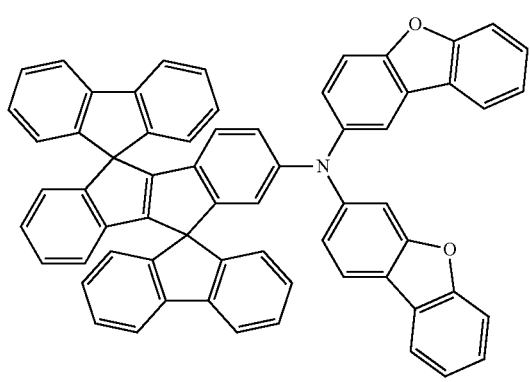

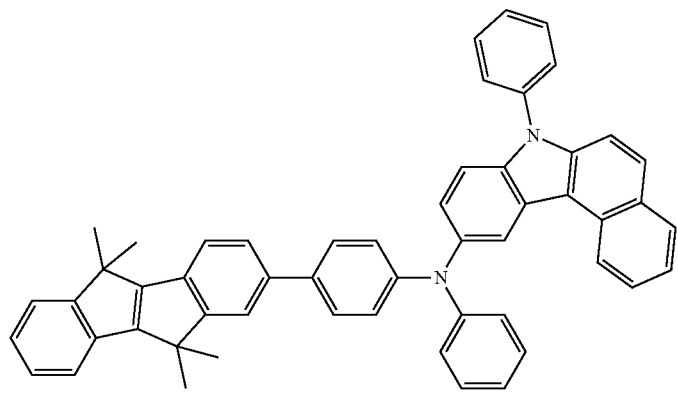
68
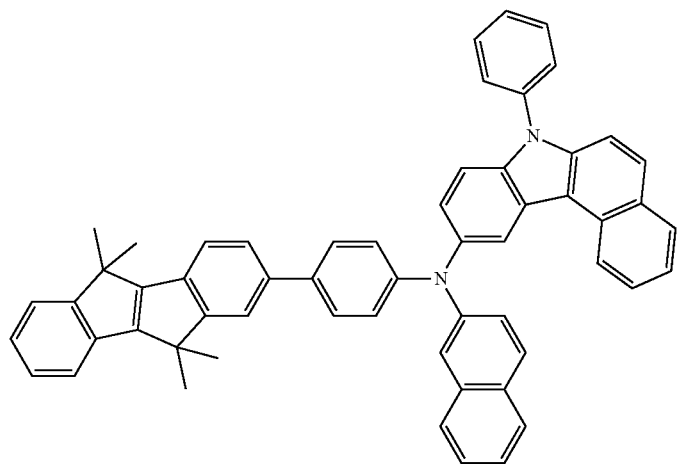
69
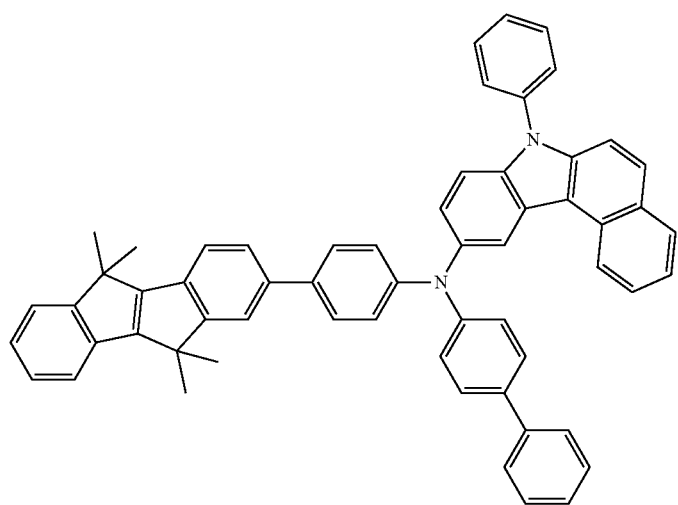
70

-continued
71
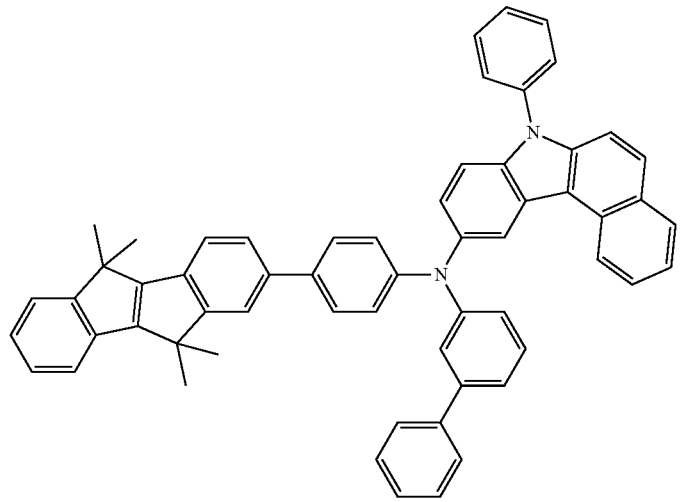
72
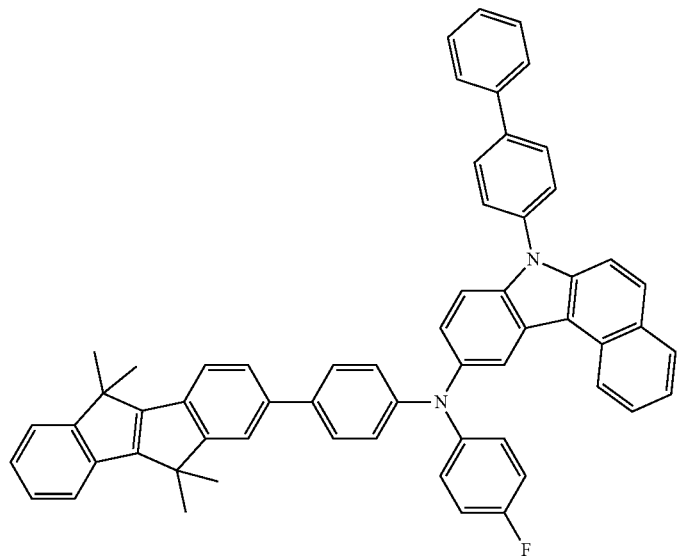
73
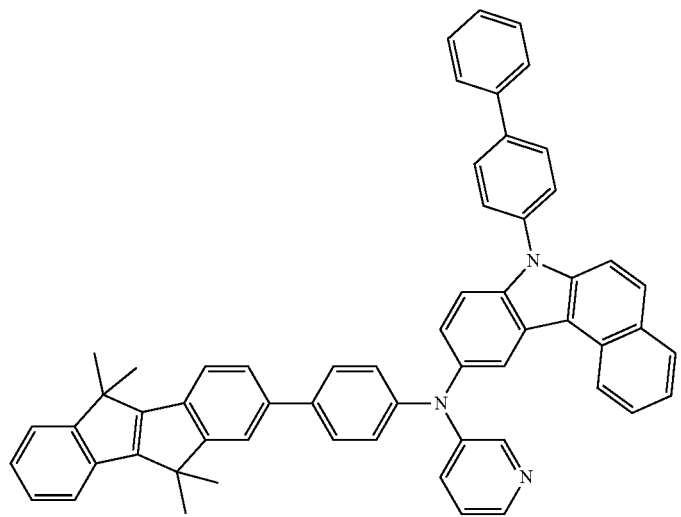

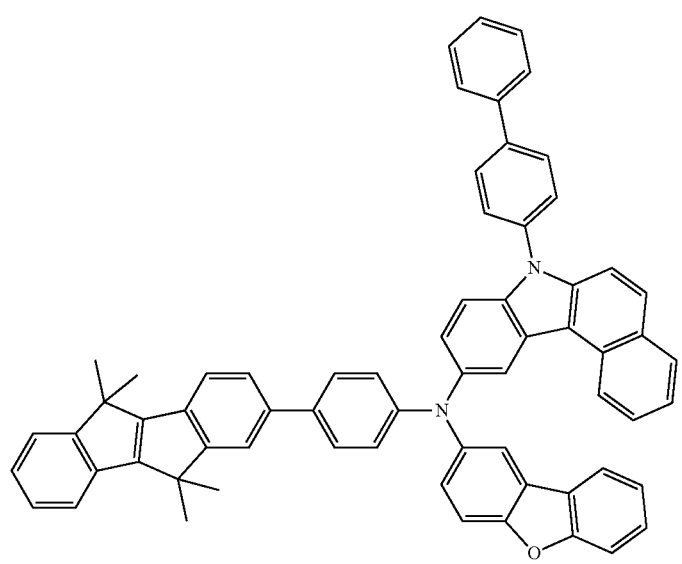
74
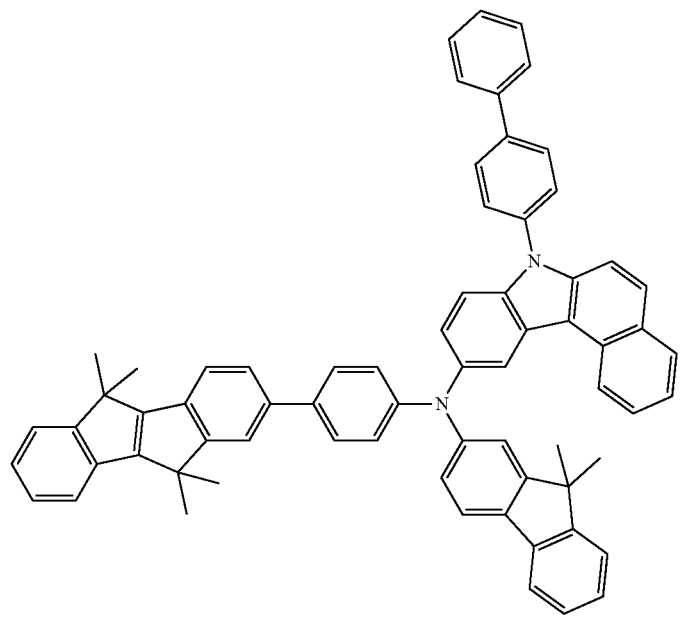
75

-continued
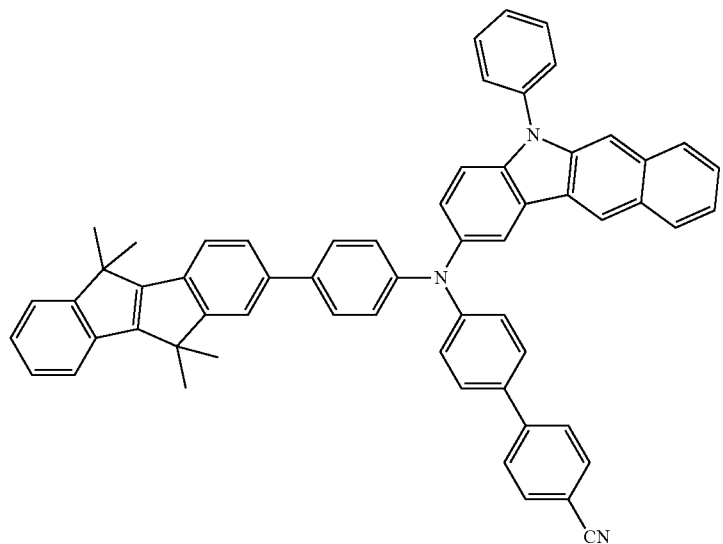
76
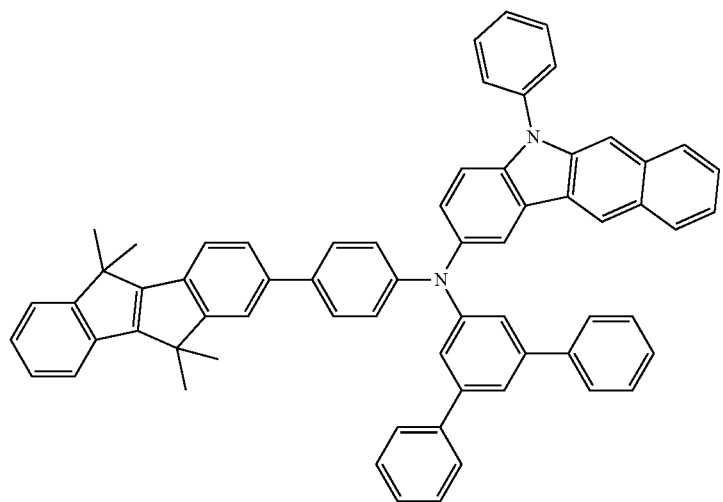
77
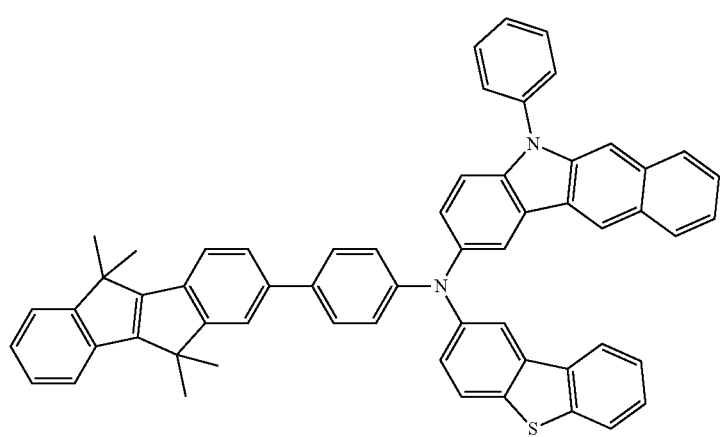
78

79
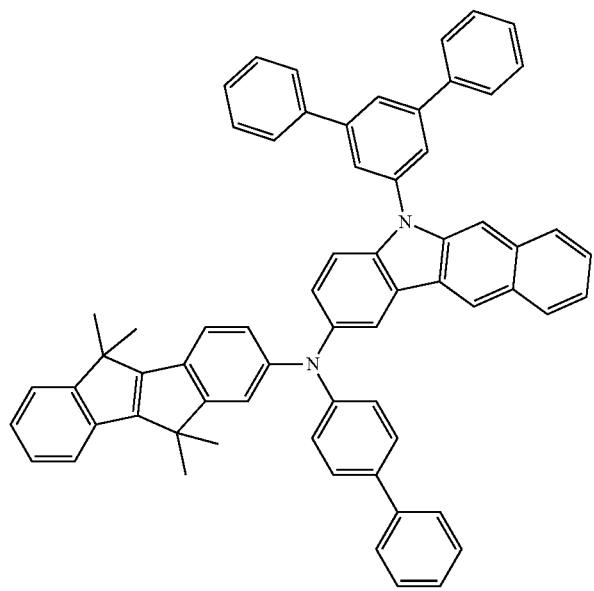
80
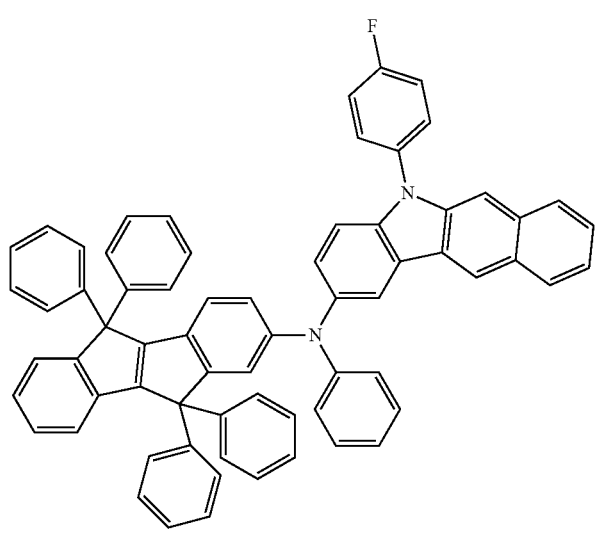
81
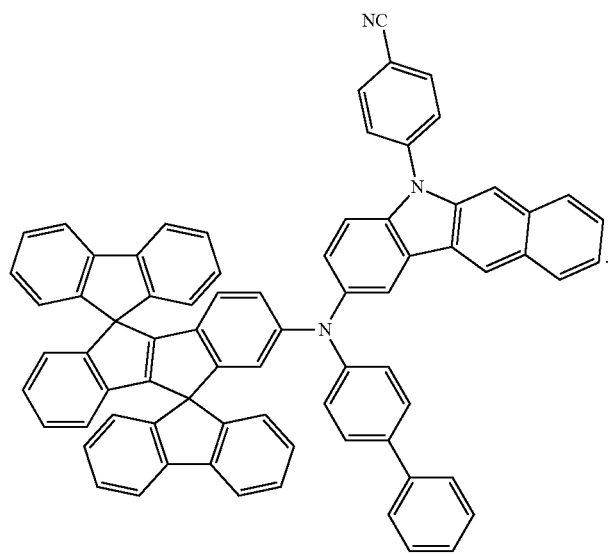

As used herein, the term "organic layer" may refer to a single layer and/or a plurality of layers between the first electrode and the second electrode in an organic light-emitting device. The material included in the "organic layer" is not limited to a particular organic material.

The drawing is a schematic view of an organic light-emitting device 10 according to one or more embodiments of the present disclosure. The organic light-emitting device 10 may include a first electrode 110, an organic layer 150, and a second electrode 190.

Hereinafter, a structure and a method of manufacturing the organic light-emitting device according to one or more embodiments of the present disclosure will be described with reference to the drawing.

Referring to the drawing, a substrate may be additionally positioned under the first electrode 110 or on the second electrode 190. The substrate may be a glass substrate and/or a transparent plastic substrate, each with excellent mechanical strength, thermal stability, transparency, surface smoothness, ease of handling, and/or water resistance.

The first electrode 110 may be formed by depositing and/or sputtering a first electrode material on the substrate. When the first electrode 110 is an anode, the first electrode material may be selected from materials with a high work function in order to facilitate hole injection. The first electrode 110 may be a reflective electrode, a semi-transmissive electrode, or a transmissive electrode. The first electrode material may be a transparent and highly conductive material, and non-limiting examples of such a material may include indium tin oxide (ITO), indium zinc oxide (IZO), tin oxide ($SnO_2$), and/or zinc oxide (ZnO). Alternatively, in order to form the first electrode 110 that is a semi-transmissive electrode or a reflective electrode, at least one material selected from magnesium (Mg), aluminum (Al), aluminum-lithium (Al—Li), calcium (Ca), magnesium-indium (Mg—In), and magnesium-silver (Mg—Ag) may be used as a first electrode material.

The first electrode 110 may have a single-layer structure, or a multi-layer structure including a plurality of layers. For example, the first electrode 110 may have a triple-layer structure of ITO/Ag/ITO, but embodiments of the present disclosure are not limited thereto.

The organic layer 150 may be positioned on the first electrode 110. The organic layer 150 may include an emission layer.

The organic layer 150 may further include a hole transport region between the first electrode 110 and the emission layer, and/or an electron transport region between the emission layer and the second electrode 190.

The hole transport region may include a hole transport layer; and at least one layer selected from a hole injection layer, a buffer layer, and an electron blocking layer, but embodiments of the present disclosure are not limited thereto. The electron transport region may include at least one layer selected from a hole blocking layer, an electron transport layer, and an electron injection layer, but embodiments of the present disclosure are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single layer formed of a plurality of different materials, or may have a structure of hole injection layer/hole transport layer, hole injection layer/hole transport layer/buffer layer, hole injection layer/buffer layer, hole transport layer/buffer layer, or hole injection layer/hole transport layer/electron blocking layer, wherein layers of each structure are sequentially stacked on the first electrode 110 in these stated orders, but embodiments of the present disclosure are not limited thereto.

When the hole transport region includes a hole injection layer, the hole injection layer may be formed on the first electrode 110 using one or more suitable methods, such as vacuum-deposition, spin coating, casting, a Langmuir-Blodgett (LB) method, ink-jet printing, laser-printing, and/or laser-induced thermal imaging (LITI).

When the hole injection layer is formed by vacuum deposition, the deposition may be performed, e.g., at a deposition temperature of about 100° C. to about 500° C., at a vacuum degree of about $10^{-8}$ torr to about $10^{-3}$ torr, and a deposition rate of about 0.01 Å/sec to about 100 Å/sec, taking into account the compound to be included in the hole injection layer and the desired structure of the hole injection layer.

When the hole injection layer is formed by spin coating, the coating may be performed, e.g., at a coating speed of about 2,000 rpm to about 5,000 rpm and at a temperature of about 80° C. to about 200° C., taking into account the compound to be included in the hole injection layer and the desired structure of the hole injection layer.

When the hole transport region includes a hole transport layer, the hole transport layer may be formed on the first electrode 110 or on the hole injection layer using one or more suitable methods, such as vacuum-deposition, spin coating, casting, an LB method, ink-jet printing, laser-printing, and/or LITI. When the hole transport layer is formed by vacuum-deposition and/or spin coating, the conditions for vacuum-deposition and coating may be similar to the above-described vacuum-deposition and coating conditions for forming the hole injection layer.

The hole transport region may include the compound represented by Formula 1 according to one or more embodiments of the present disclosure. The hole transport region may further include at least one compound selected from m-MTDATA, TDATA, 2-TNATA, NPB, β-NPB, TPD, spiro-TPD, spiro-NPB, α-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), and polyaniline/poly(4-styrenesulfonate) (PANI/PSS), in addition to the compound represented by Formula 1:

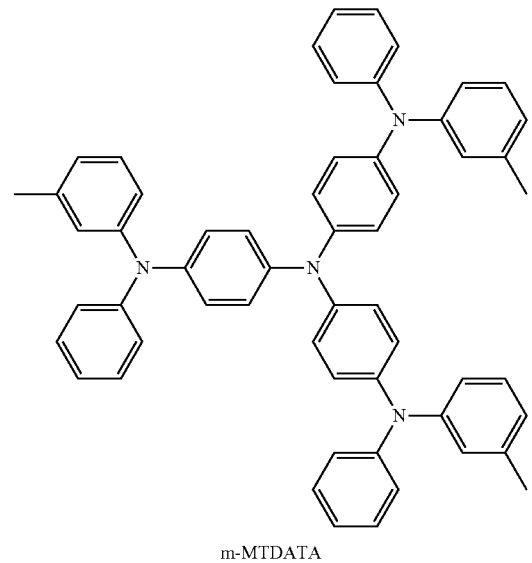

m-MTDATA

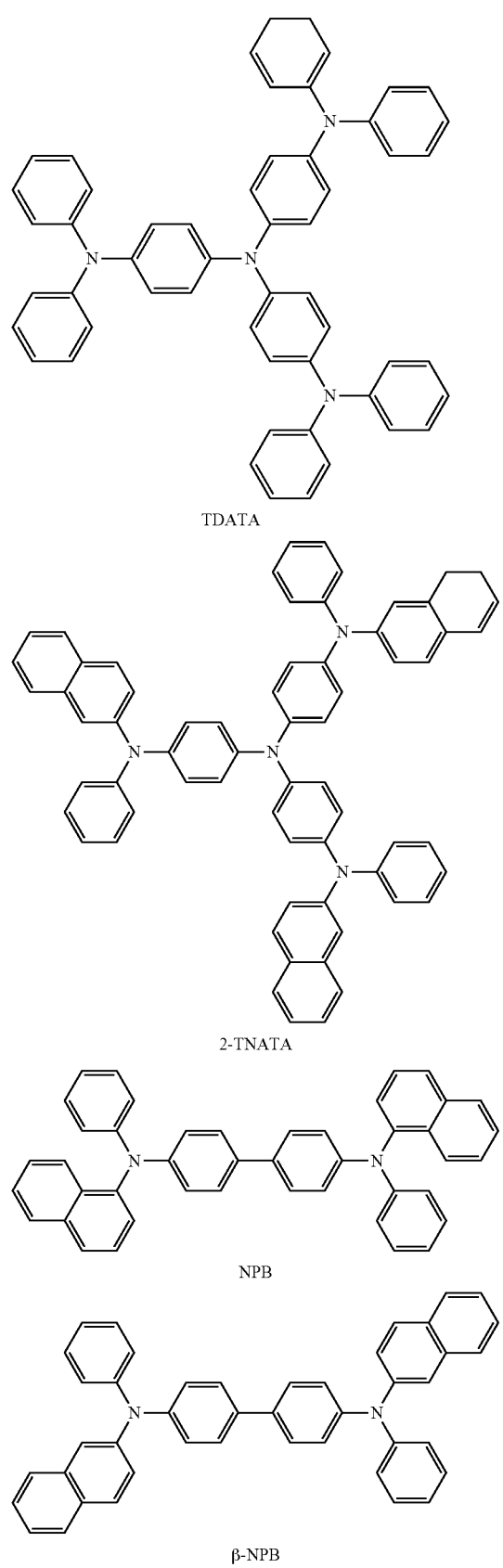
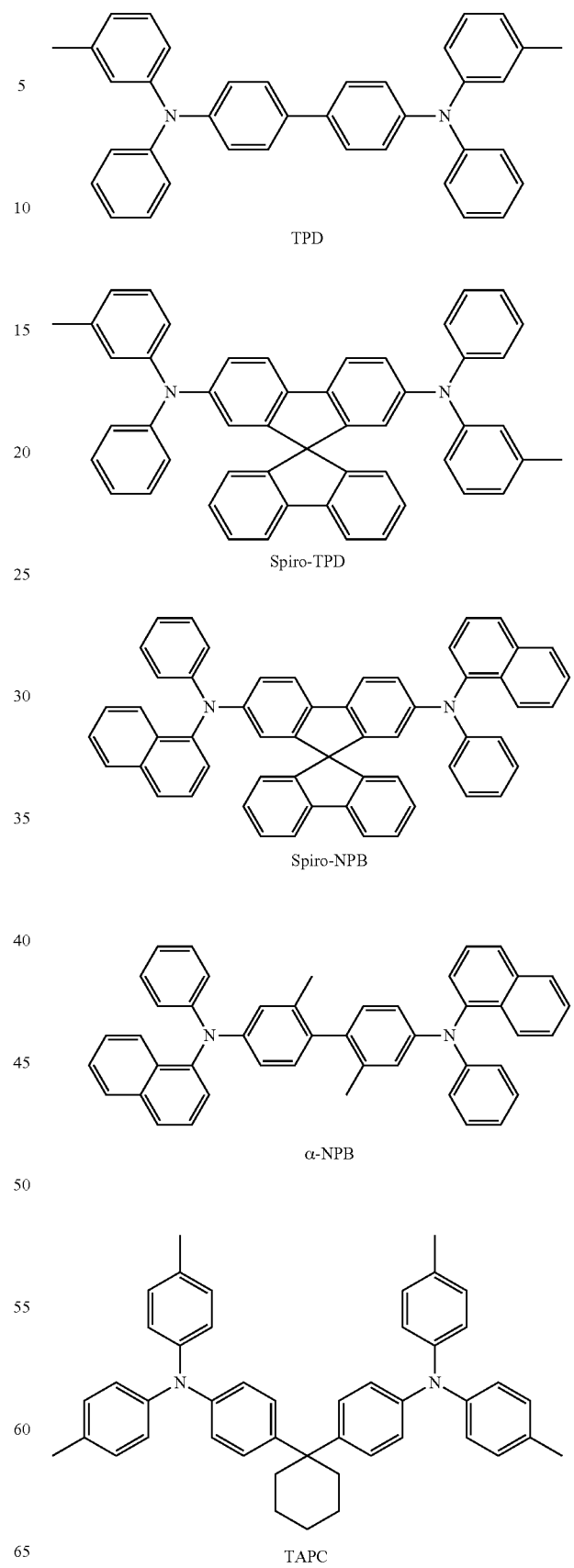

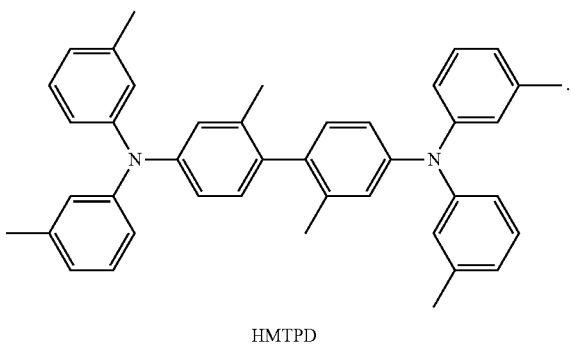

HMTPD

The thickness of the hole transport region may be about 100 Å to about 10,000 Å, and in some embodiments, about 100 Å to about 1,000 Å. When the hole transport region includes a hole injection layer and a hole transport layer, the thickness of the hole injection layer may be about 100 Å to about 10,000 Å, and in some embodiments, about 100 Å to about 1,000 Å; the thickness of the hole transport layer may be about 50 Å to about 2,000 Å, and in some embodiments, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be a material selected from a quinone derivative, a metal oxide, and a compound containing a cyano group, but embodiments of the present disclosure are not limited thereto. For example, non-limiting examples of the p-dopant may include a quinone derivative (such as tetracyanoquinonedimethane (TCNQ) and/or 2,3,5,6-tetrafluoro-tetracyano-1,4-benzoquinonedimethane (F4-TCNQ)); a metal oxide (such as a tungsten oxide and/or a molybdenum oxide), and Compound HT-D1, illustrated below, but embodiments of the present disclosure are not limited thereto.

Compound HT-D1

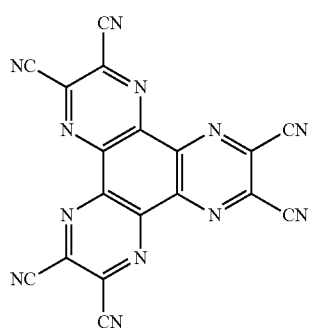

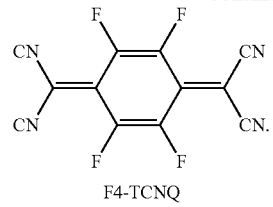

F4-TCNQ

The hole transport region may further include a buffer layer in addition to the electron blocking layer, hole injection layer, and hole transport layer described above. Since the buffer layer may be used to tune the optical resonance distance according to the wavelength of light emitted from the emission layer, the light-emission efficiency of the organic light-emitting device may be improved. Materials that are included in the hole transport region may also be included in the buffer layer. The electron blocking layer may prevent or reduce injection of electrons from the electron transport region.

An emission layer may be formed on the first electrode 110 or on the hole transport region using one or more suitable methods, such as vacuum-deposition, spin coating, casting, an LB method, ink-jet printing, laser-printing, and/or LITI. When the emission layer is formed by vacuum-deposition and/or spin coating, the deposition and coating conditions for the emission layer may be similar to the above-described deposition and coating conditions for forming the hole injection layer.

When the organic light-emitting device 10 is a full color organic light-emitting device, the emission layer may be patterned into a red emission layer, a green emission layer, and/or a blue emission layer, according to a sub pixel. In one or more embodiments, the emission layer may have a stacked structure including a red emission layer, a green emission layer, and a blue emission layer, or may include a red-light emission material, a green-light emission material, and a blue-light emission material, which are mixed with each other in a single layer to thereby emit white light.

The emission layer may include a host and a dopant.

In some embodiments, the host may include at least one compound selected from TPBi, TBADN, ADN (or "DNA"), CBP, CDBP, and TCP:

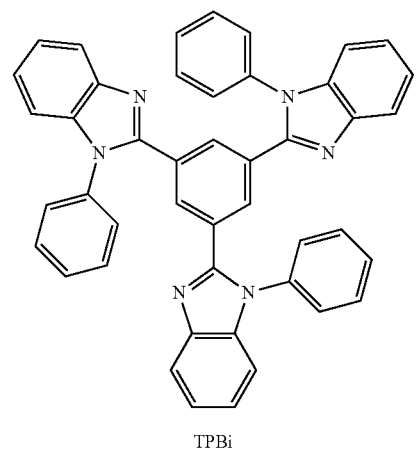

TPBi

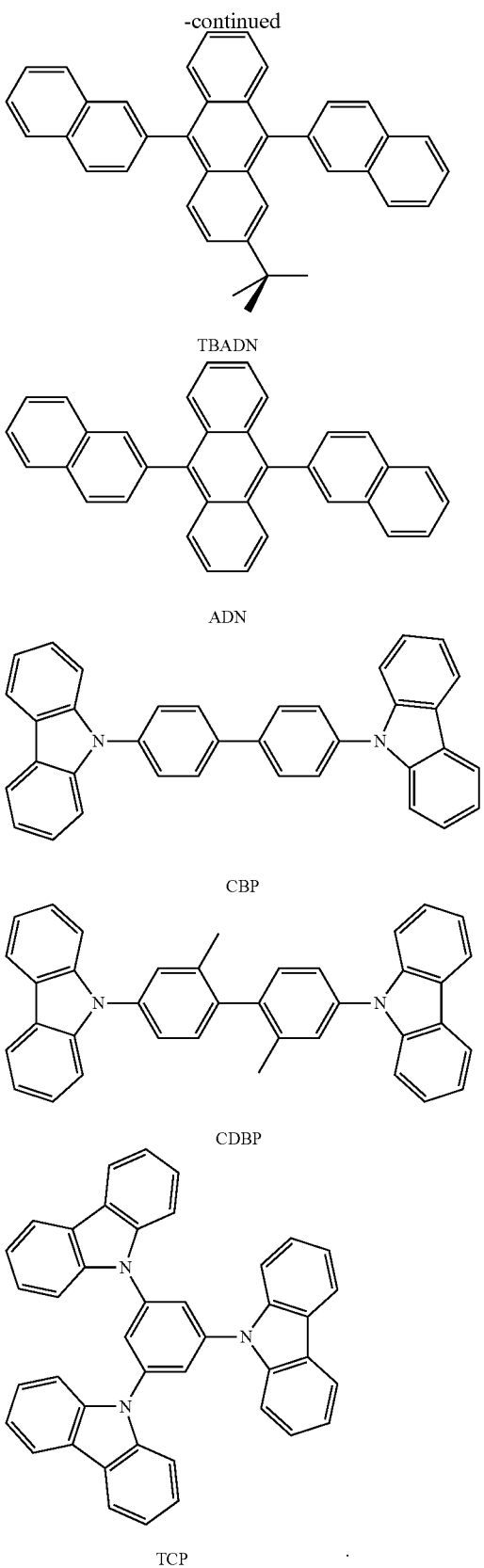

TBADN

ADN

CBP

CDBP

TCP

In one or more embodiments, the host may further include a compound represented by Formula 301:

$$Ar_{301}\text{-}[(L_{301})_{xb1}\text{-}R_{301}]_{xb2}.$$  Formula 301

In Formula 301,

Ar$_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{301}$)(Q$_{302}$)(Q$_{303}$) (e.g., a substituted silyl group) (wherein Q$_{301}$ to Q$_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

L$_{301}$ may be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

R$_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3, and xb2 may be selected from 1, 2, 3, and 4.

In some embodiments, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present disclosure are not limited thereto.

In some embodiments, the host may include a compound represented by Formula 301A:

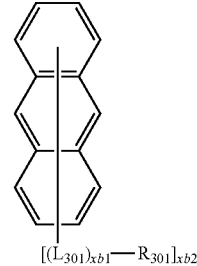

Formula 301A $[(L_{301})_{xb1}\text{—}R_{301}]_{xb2.}$

The descriptions for Formula 301A may be understood by referring to the descriptions provided herein in connection with Formula 301.

The compound represented by Formula 301 may include at least one compound selected from Compounds H1 to H42, but embodiments of the present disclosure are not limited thereto:

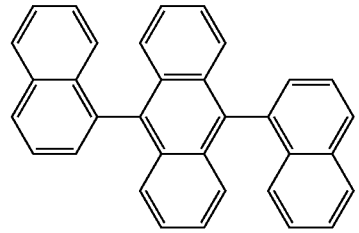

H1

H2
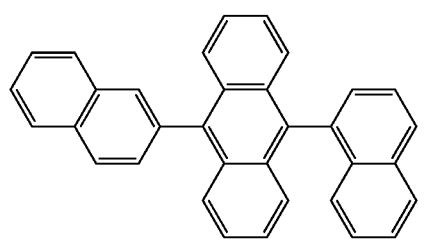
H3
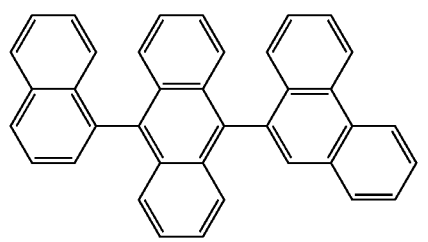
H4
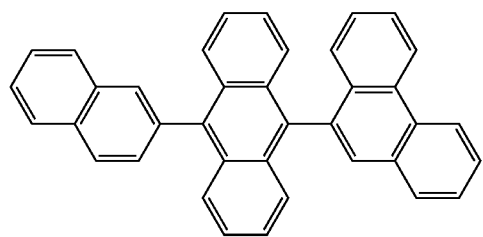
H5
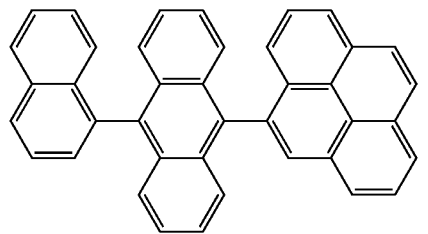
H6
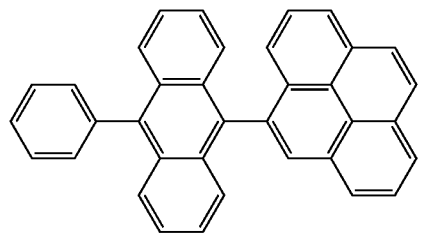
H7
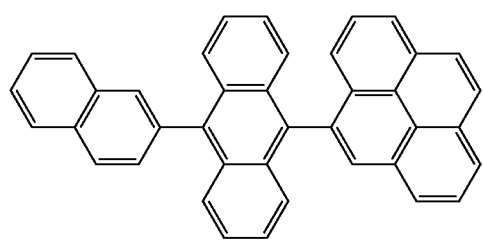
H8
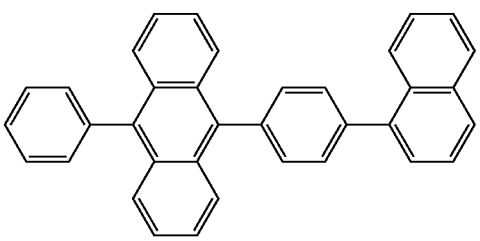
H9
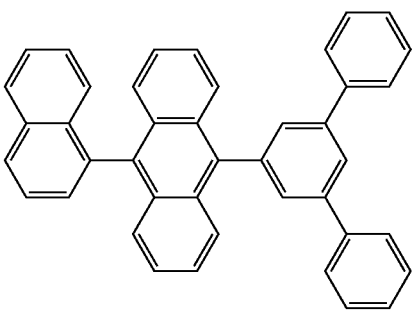
H10
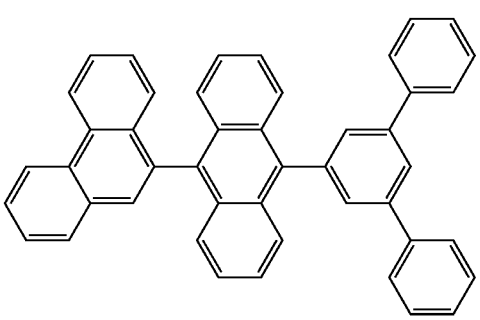
H11
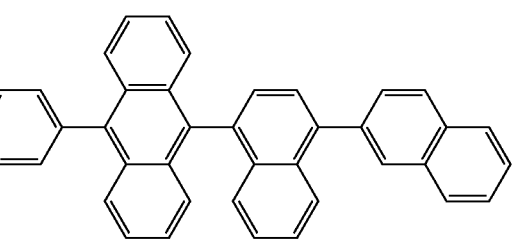
H12
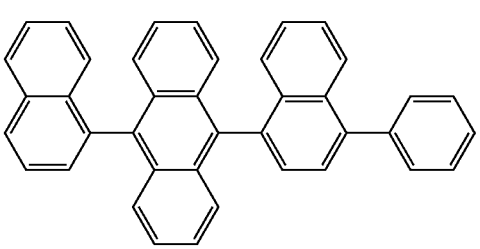
H13
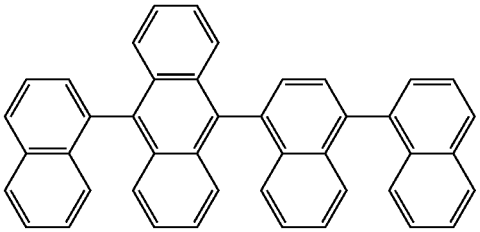

H14
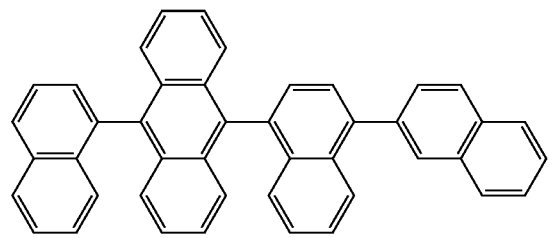
H15
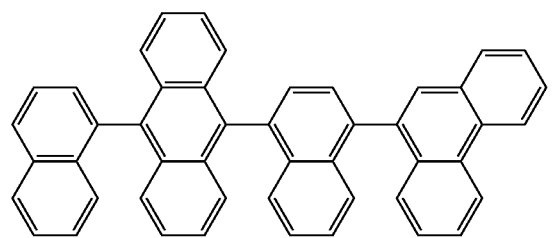
H16
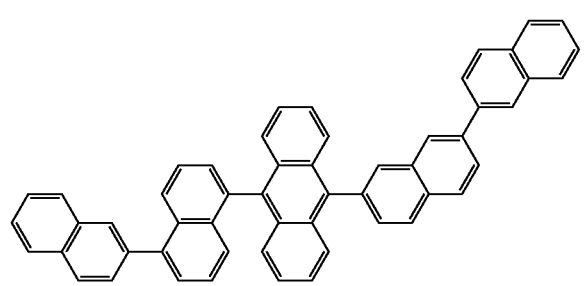
H17
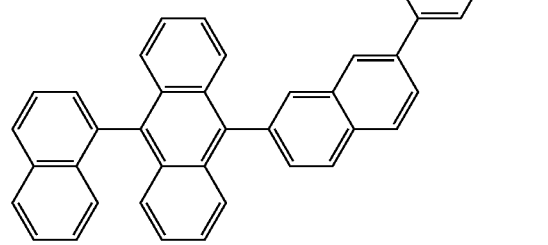
H18
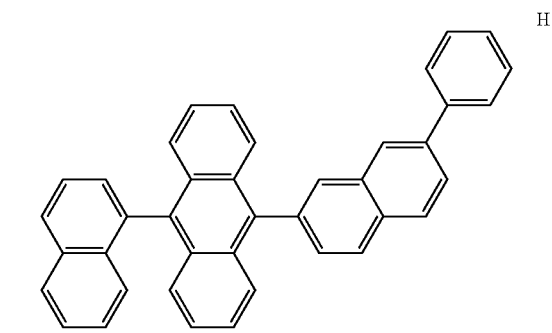
H19
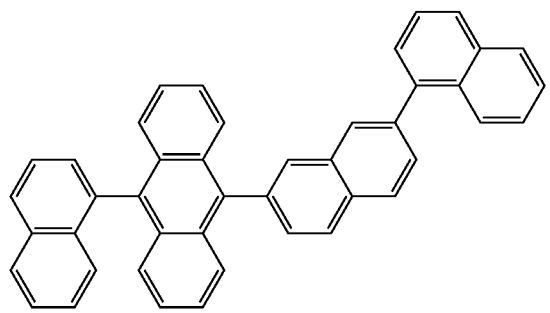
H20
H21
H22
H23
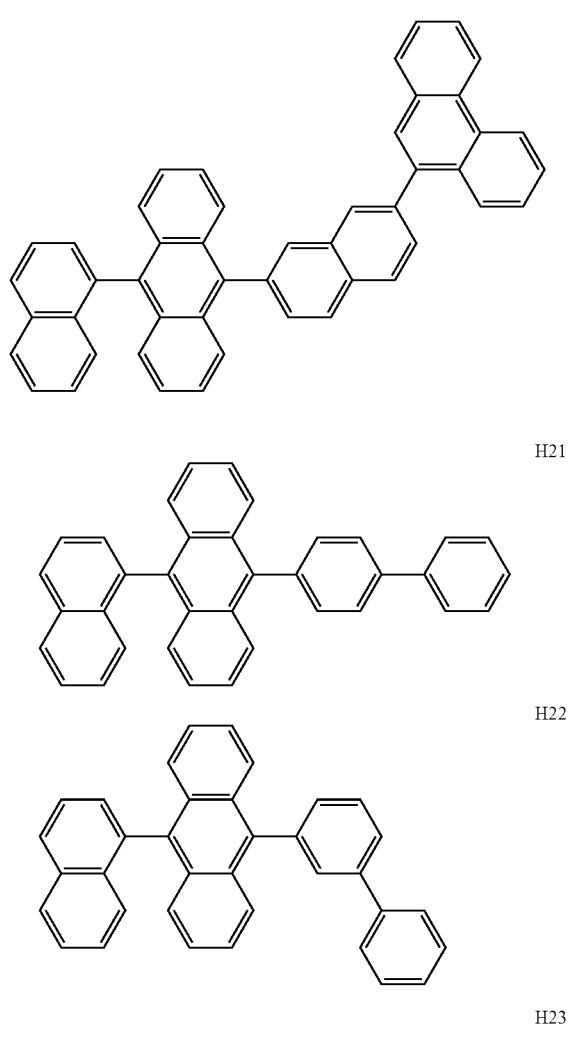

-continued
H24
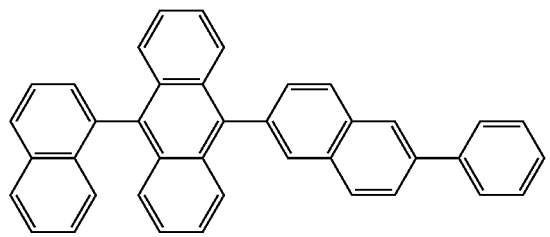
H25
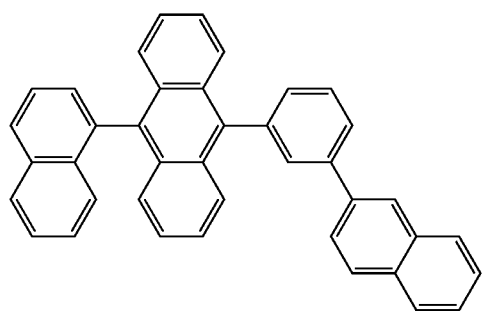
H26
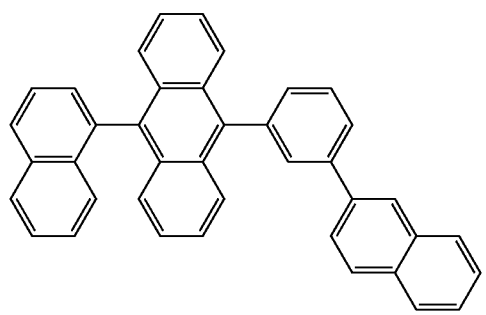
H27
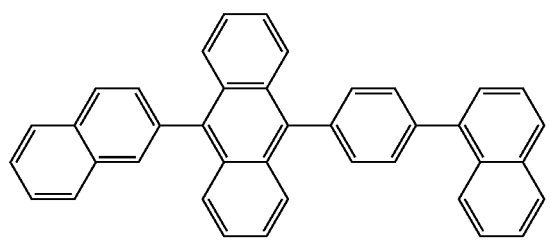
H28
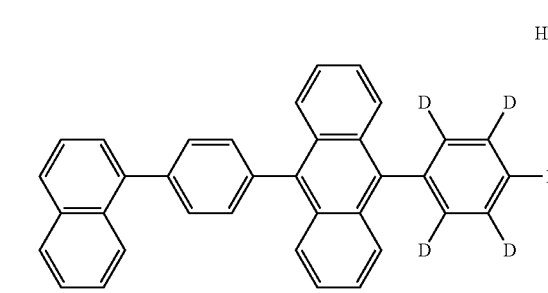
-continued
H29
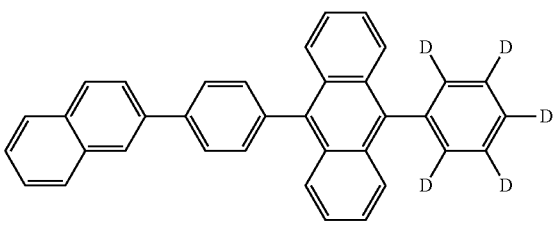
H30
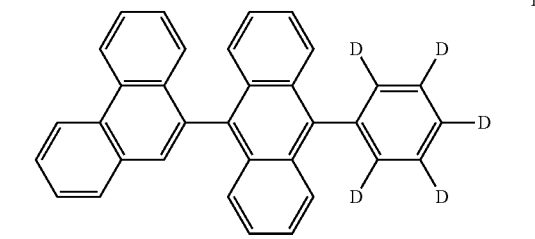
H31
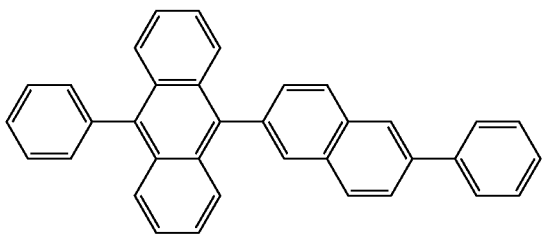
H32
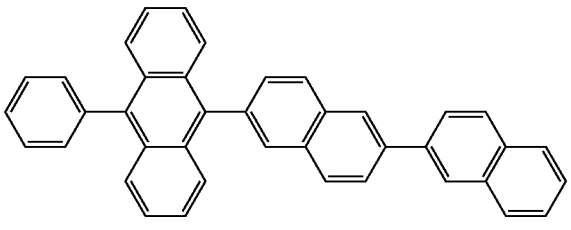
H33
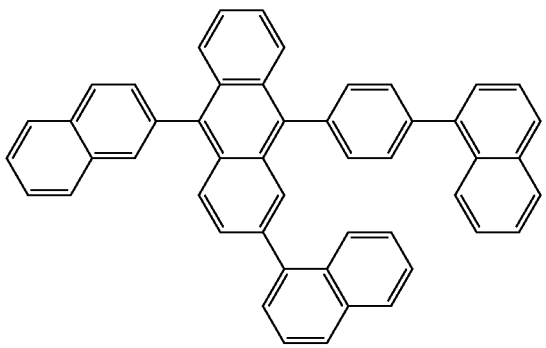

H34
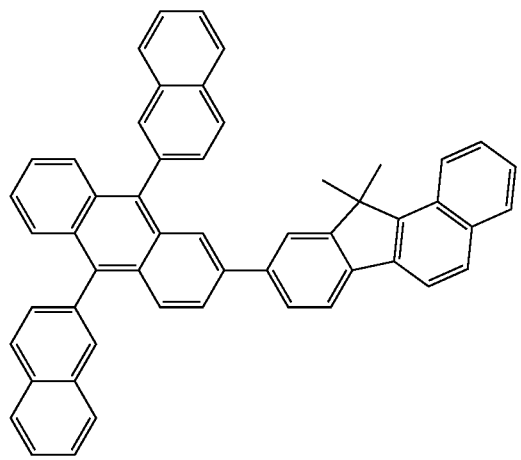
H35
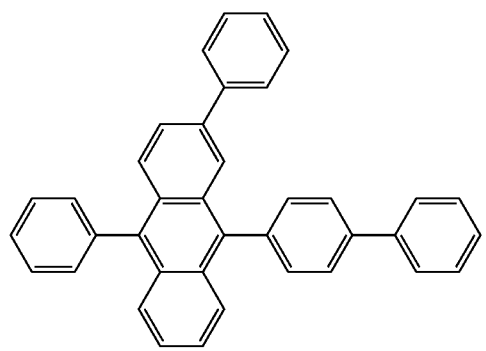
H36
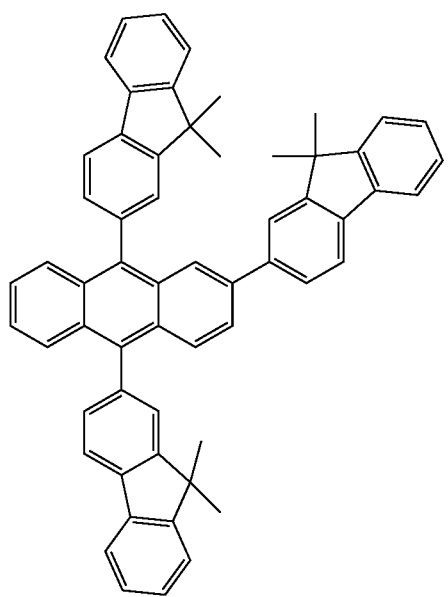
H37
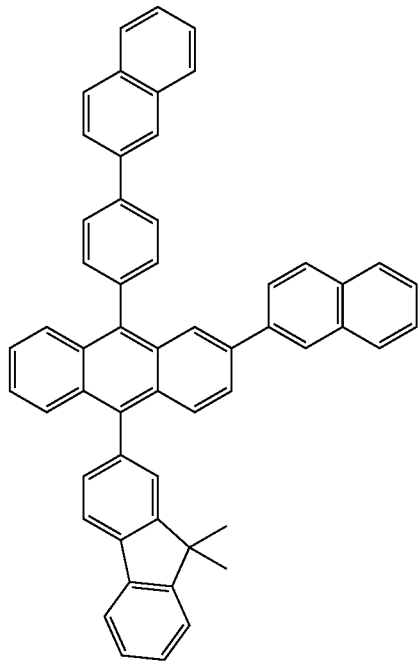
H38
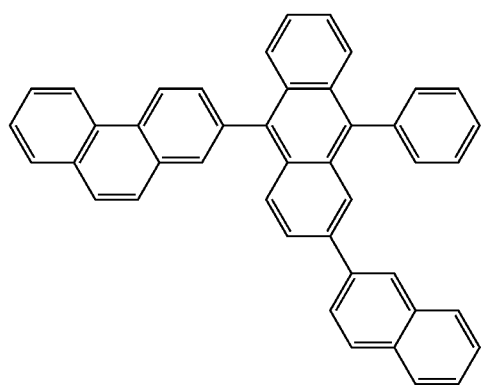
H39
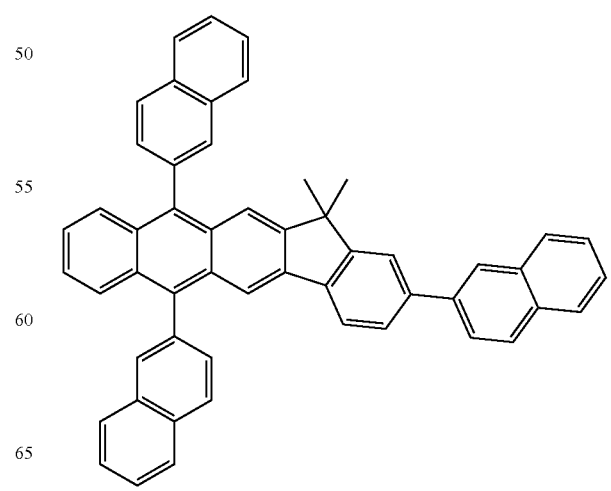

H40
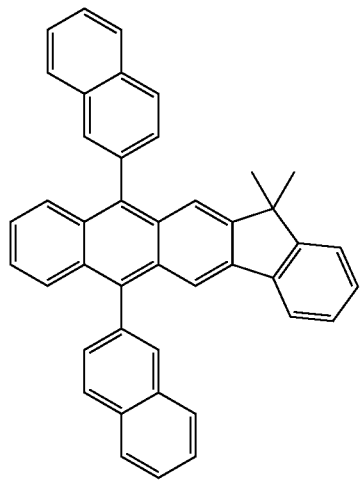
H41
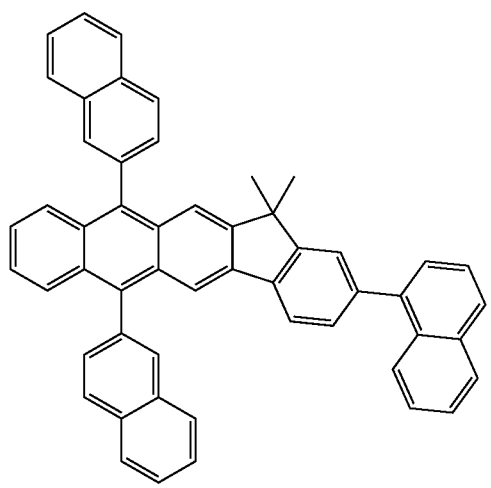
H42
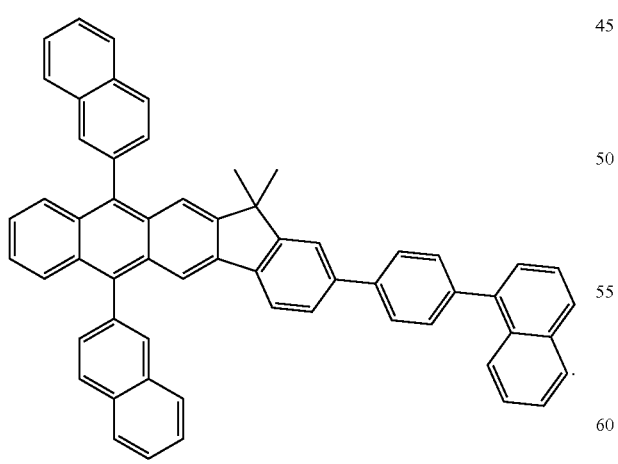
In some embodiments, the host may include at least one compound selected from Compounds H43 to H49 below, but embodiments of the present disclosure are not limited thereto:
H43
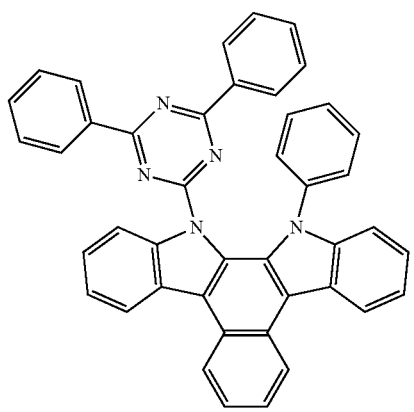
H44
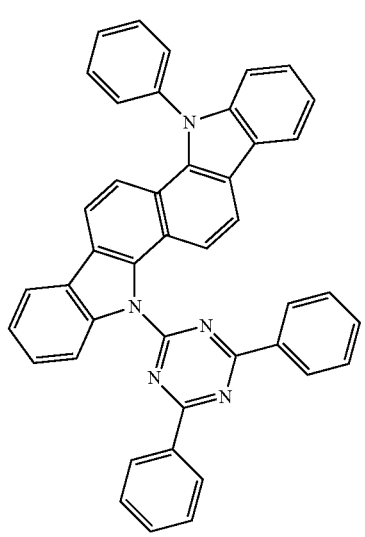
H45
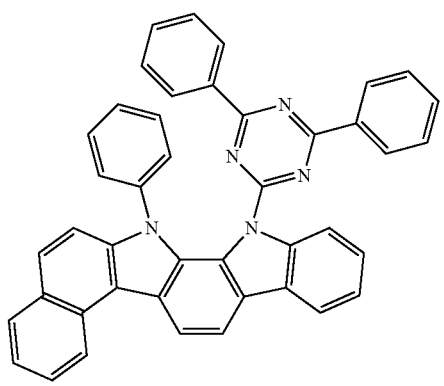

-continued

H46

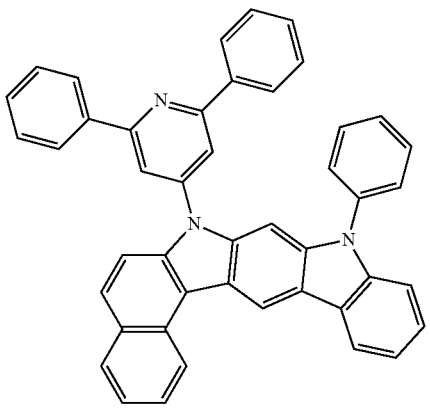

H47

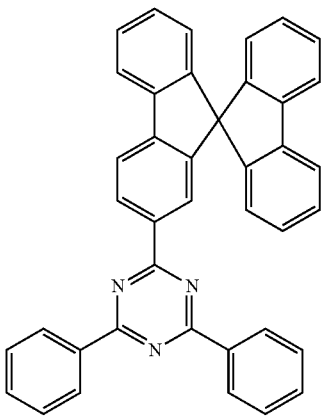

H48

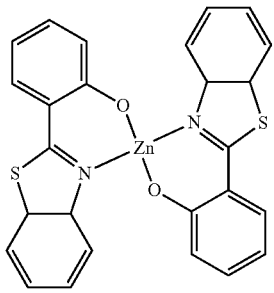

H49

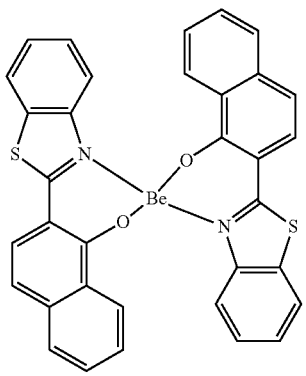

The dopant may include at least one compound selected from a fluorescent dopant and a phosphorescent dopant.

The phosphorescent dopant may include an organometallic complex represented by Formula 401 below:

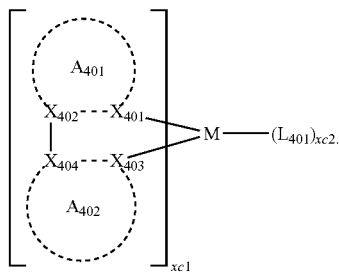

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be selected from nitrogen (N) and carbon (C);

$A_{401}$ and $A_{402}$ may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_2$-$C_{60}$ alkyl group, a $C_2$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$) (e.g., a substituted amino group), —Si($Q_{403}$)($Q_{404}$)($Q_{405}$) (e.g., a substituted silyl group), and —B($Q_{406}$)($Q_{407}$) (e.g., a substituted boryl group);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_2$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{412}$), —Si($Q_{423}$)($Q_{424}$)($Q_{425}$), and —B($Q_{426}$)($Q_{427}$), $L_{401}$ may be an organic ligand, xc1 may be selected from 1, 2, and 3, and xc2 may be selected from 0, 1, 2, and 3.

$L_{401}$ may be selected from any suitable monovalent, divalent, and trivalent organic ligand. For example, $L_{401}$ may be selected from a halogen ligand (e.g., Cl and/or F), a diketone ligand (e.g., acetylacetonate, 1,3-diphenyl-1,3-propanedionate, 2,2,6,6-tetramethyl-3,5-heptanedionate, and/or hexafluoroacetonate), a carboxylic acid ligand (e.g., picolinate, dimethyl-3-pyrazolecarboxylate, and/or benzoate), a carbon monoxide ligand, an isonitrile ligand, a cyano group ligand, and a phosphorus-based ligand (e.g., phosphine and/or phosphite), but embodiments of the present disclosure are not limited thereto.

When $A_{401}$ in Formula 401 has a plurality of substituents, the plurality of substituents of $A_{401}$ may bind to each other to form a saturated or unsaturated ring.

When $A_{402}$ in Formula 401 has a plurality of substituents, the plurality of substituents of $A_{402}$ may bind to each other to form a saturated or unsaturated ring.

When xc1 in Formula 401 is two or more, a plurality of ligands,

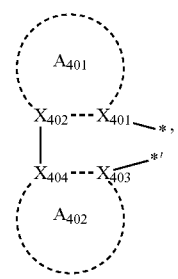

in Formula 401 may be identical to or different from each other. When xc1 in Formula 401 is 2 or greater, $A_{401}$ and $A_{402}$ may be directly connected or connected via a linking group (for example, a $C_1$-$C_5$ alkylene group, —N(R')— (where R' may be a $C_1$-$C_{10}$ alkyl group or a $C_6$-$C_{20}$ aryl group), or —C(═O)—) to other adjacent ligands of $A_{401}$ and $A_{402}$, respectively.

The phosphorescent dopant may include at least one selected from Compounds PD1 to PD74 below, but embodiments of the present disclosure are not limited thereto:

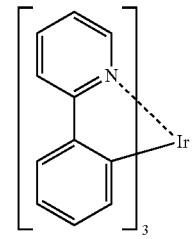

PD1

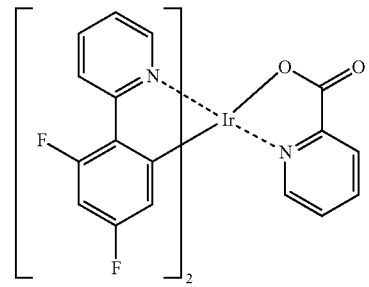

PD2

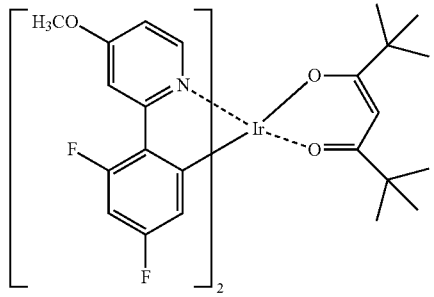

PD3

-continued
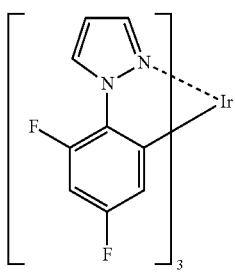 PD4
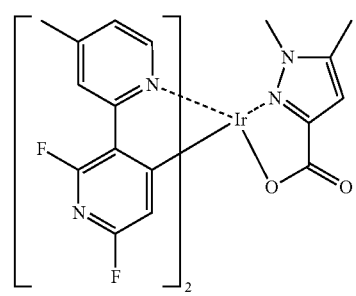 PD9
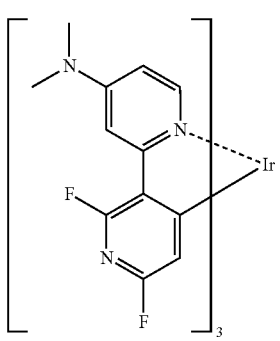 PD5
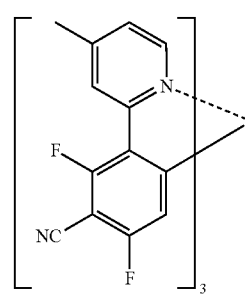 PD10
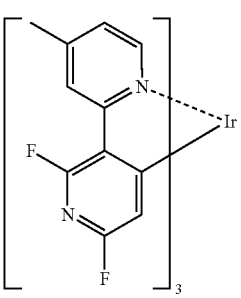 PD6
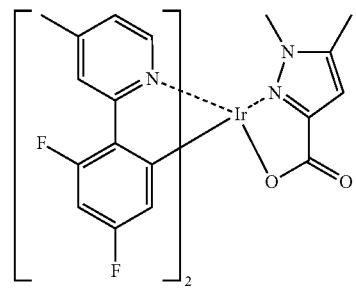 PD11
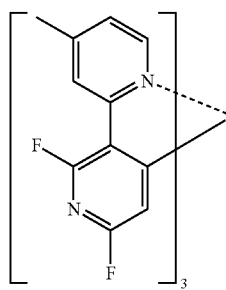 PD7
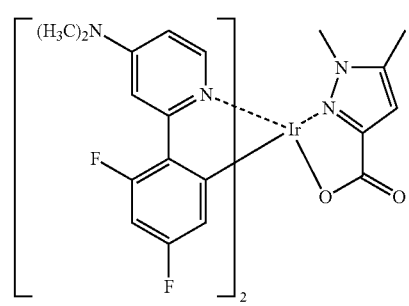 PD12
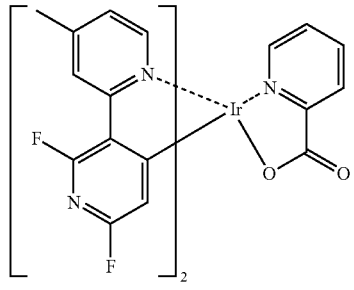 PD8
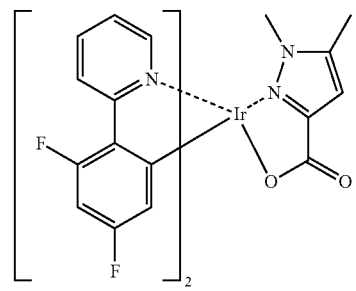 PD13

PD14
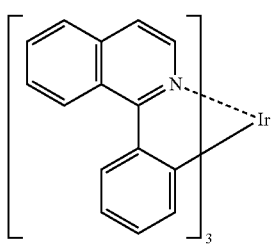
PD15
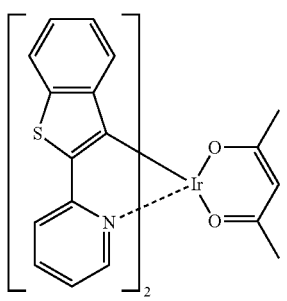
PD16
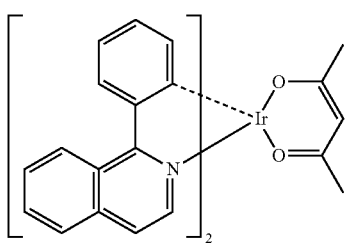
PD17
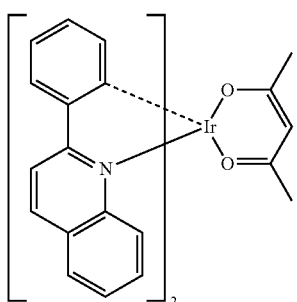
PD18
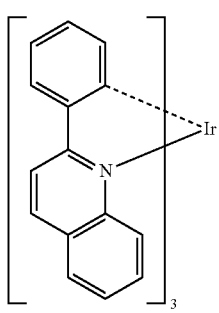
PD19
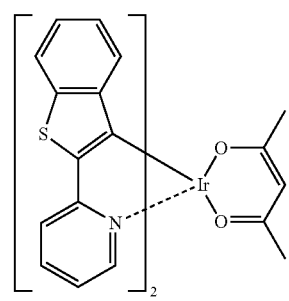
PD20
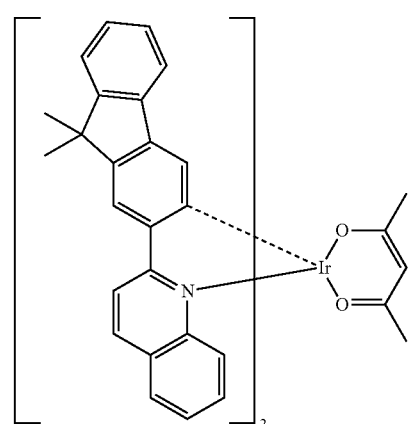
PD21
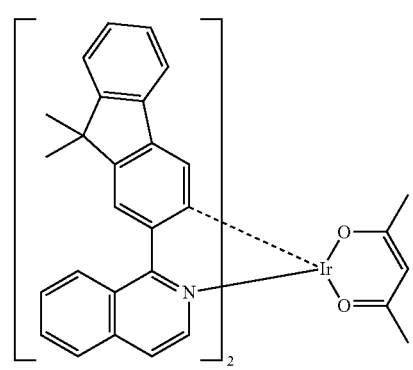
PD22
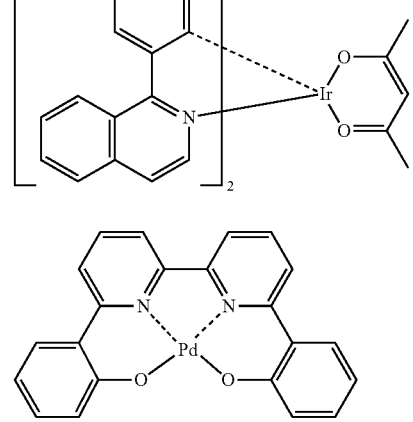
PD23
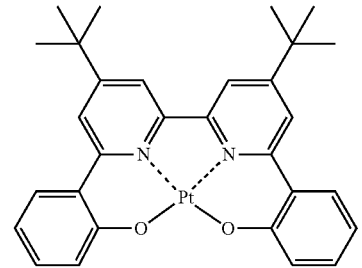

PD24 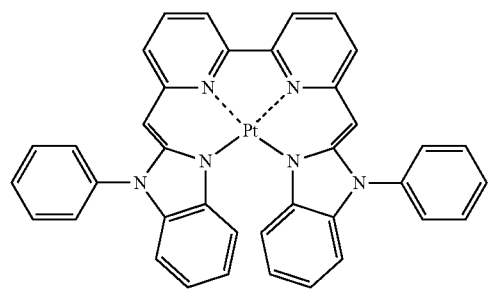
PD25 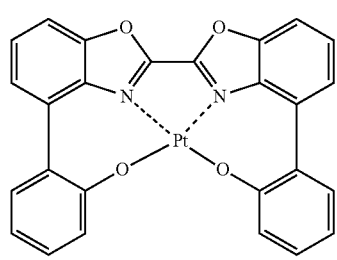
PD26 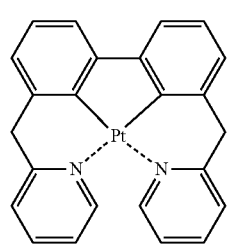
PD27 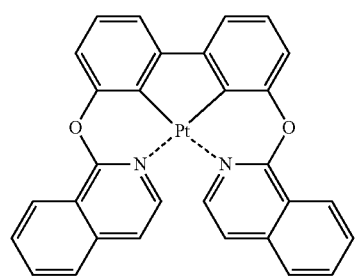
PD28 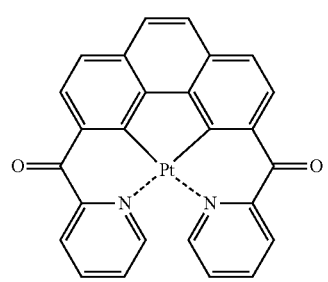
PD29 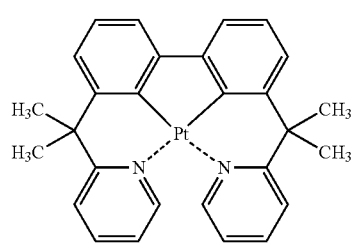
PD30 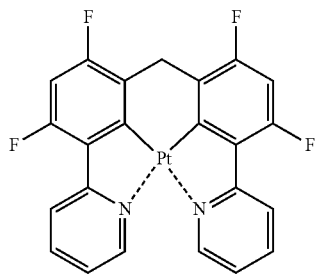
PD31 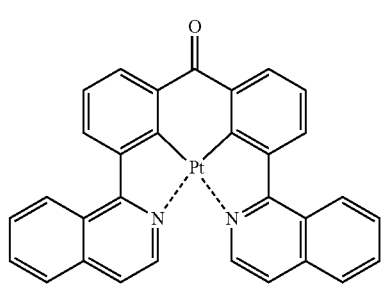
PD32 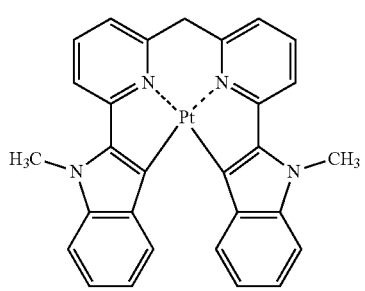
PD33 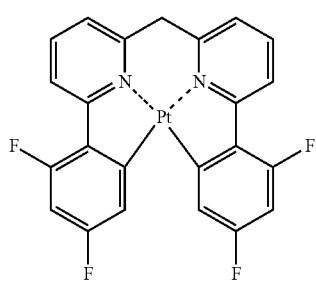
PD34 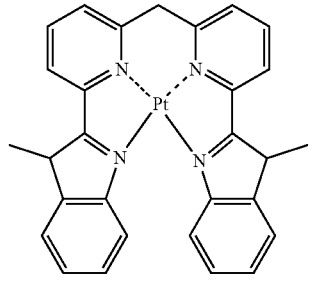

PD35 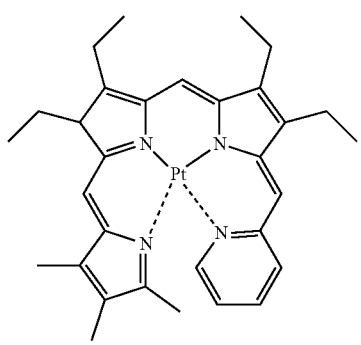
PD36 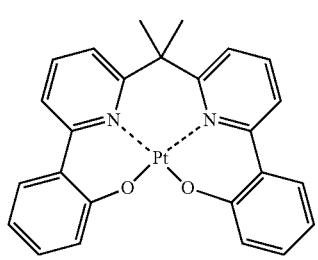
PD37 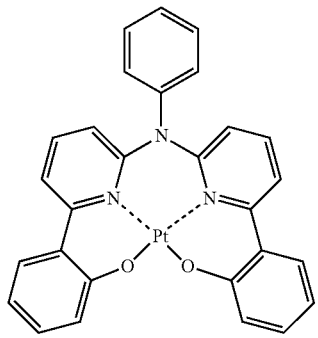
PD38 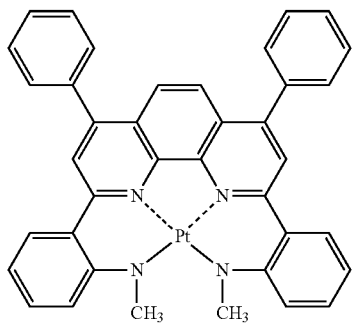
PD39 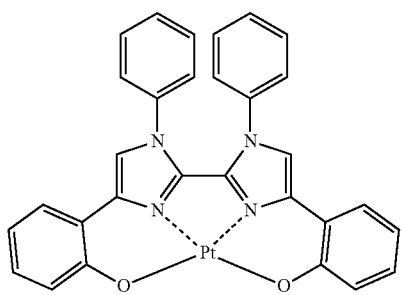
PD40 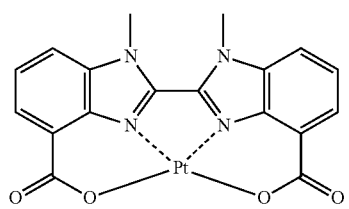
PD41 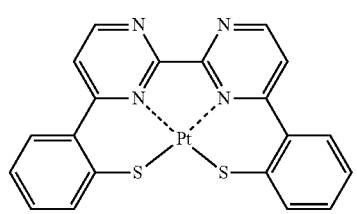
PD42 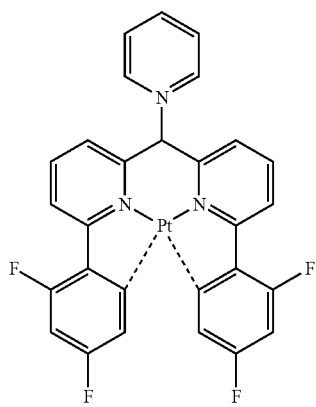
PD43 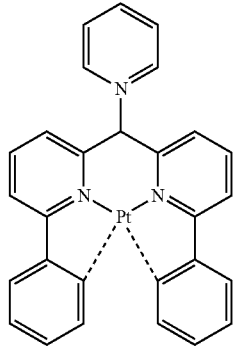
PD44 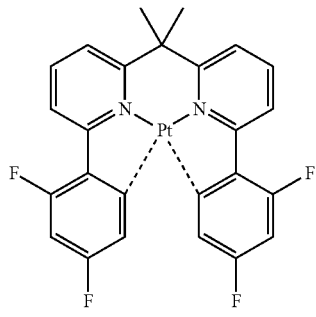

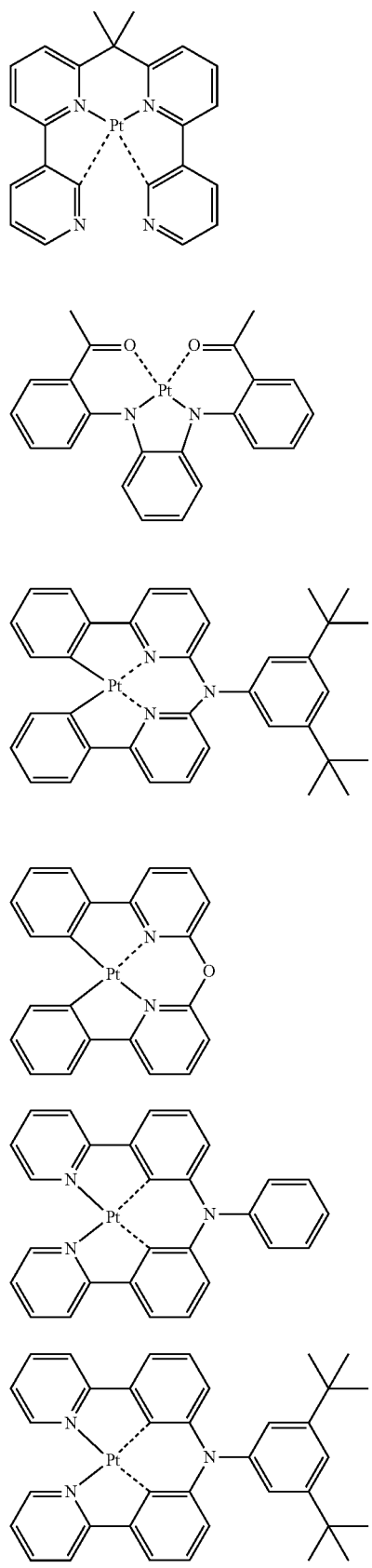
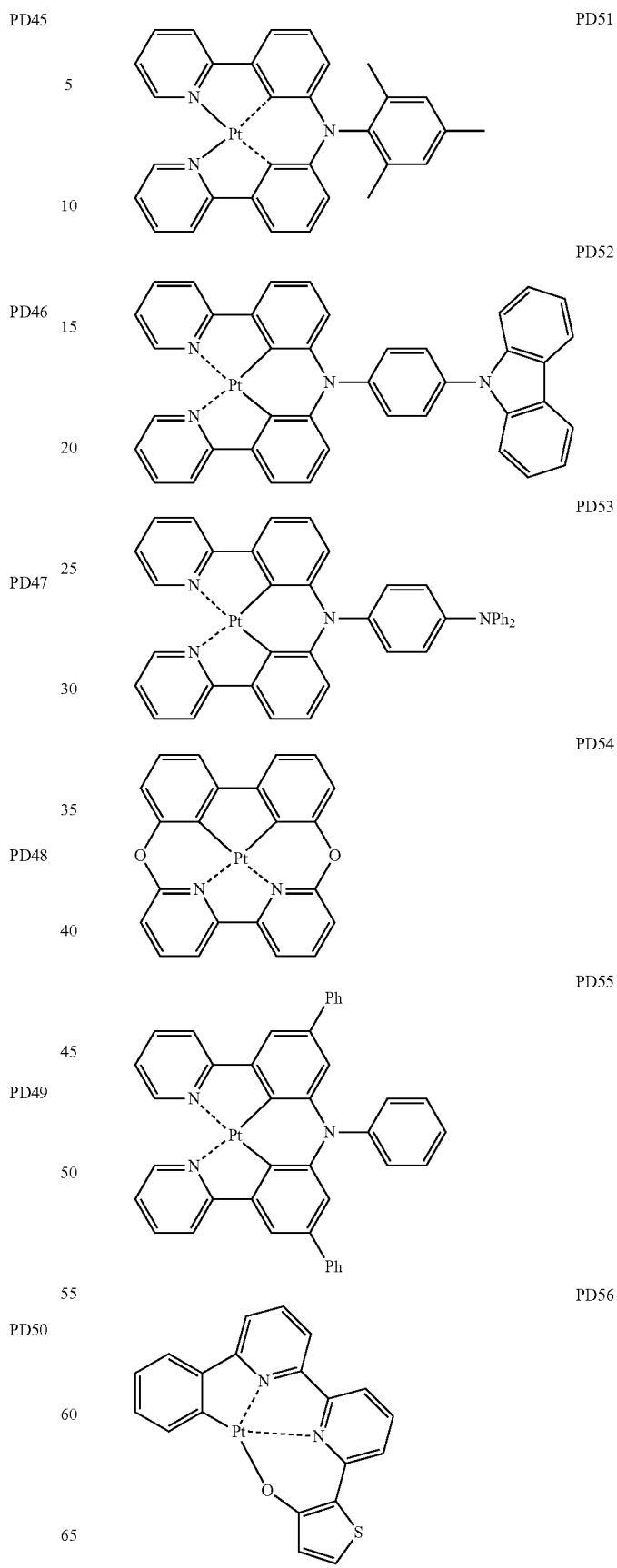

PD57
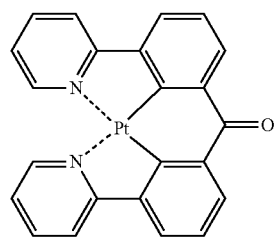
PD58
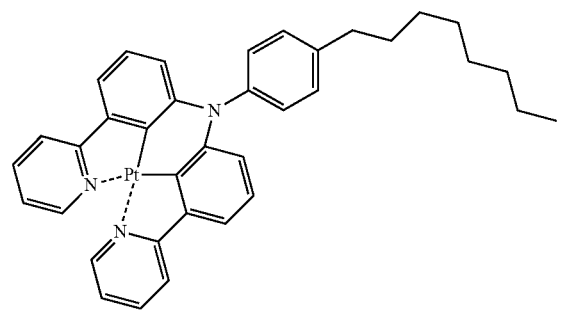
PD59
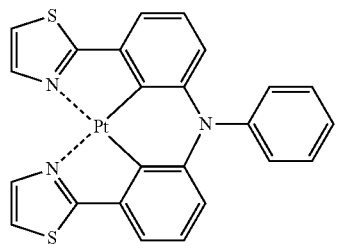
PD60
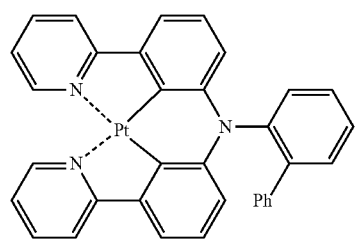
PD61
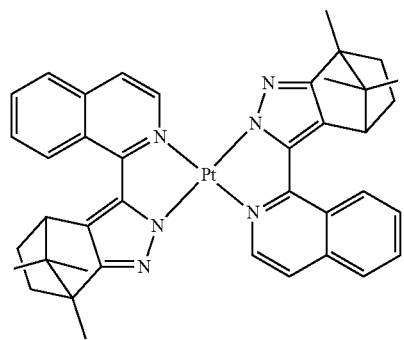
PD62
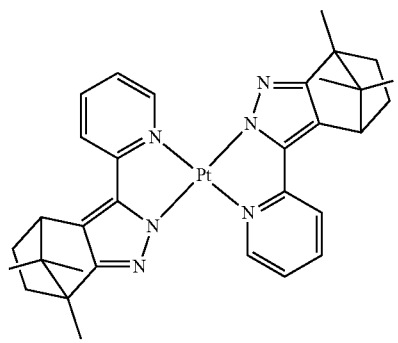
PD63
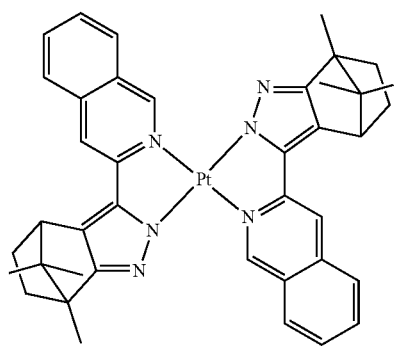
PD64
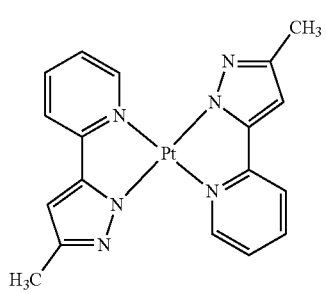
PD65
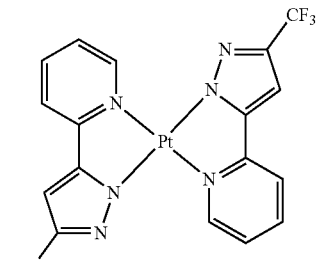
PD66
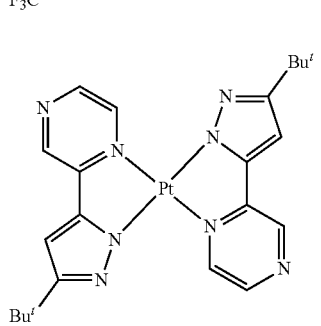

PD67
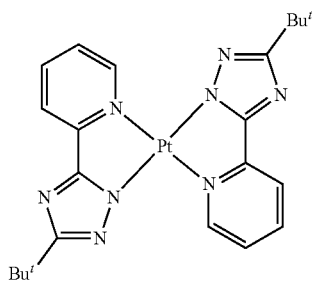
PD68
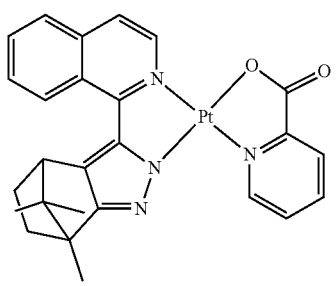
PD69
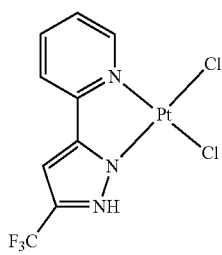
PD70
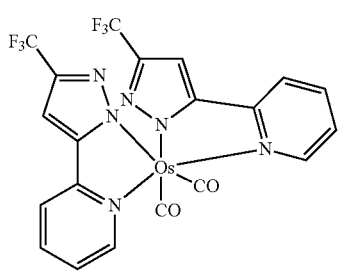
PD71
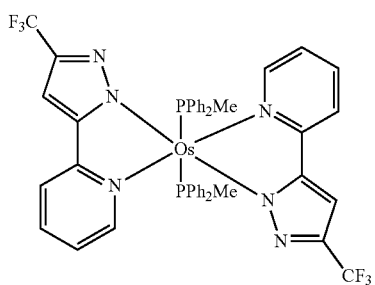
PD72
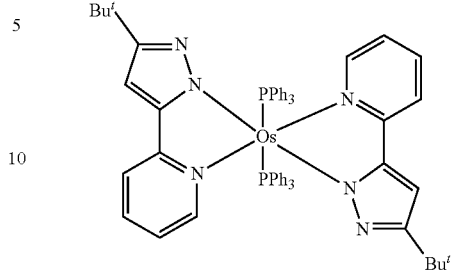
PD73
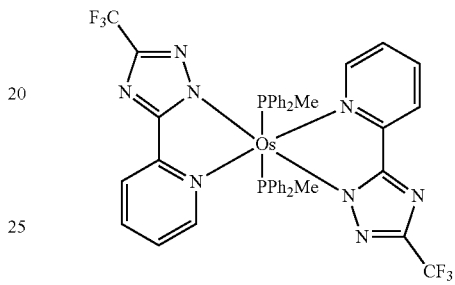
PD74
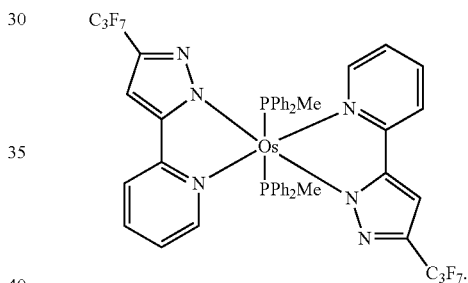
In some embodiments, the phosphorescent dopant may include PtOEP below:
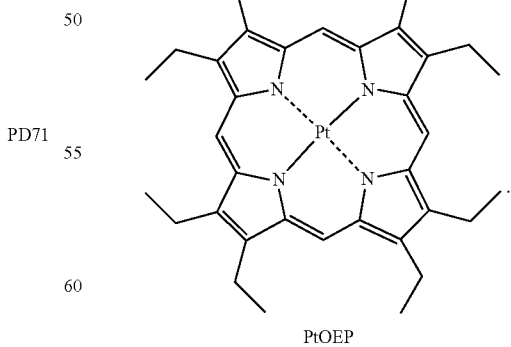
PtOEP
The fluorescent dopant may include at least one compound selected from DPVBi, DPAVBi, TBPe, DCM, DCJTB, Coumarin 6, and C545T.

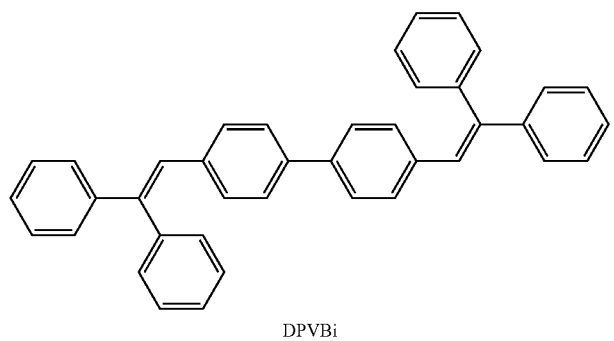

DPVBi

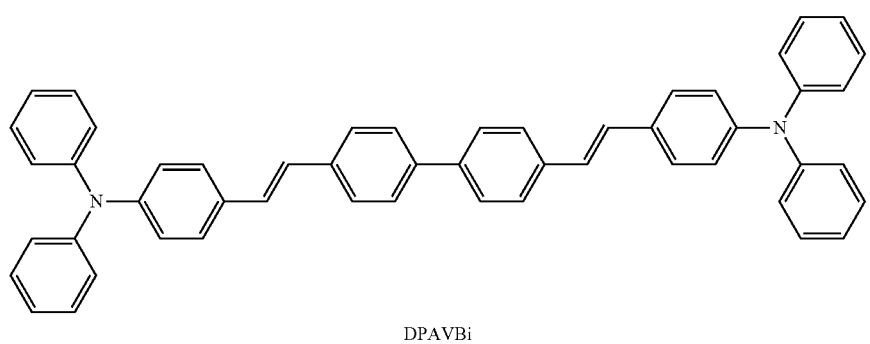

DPAVBi

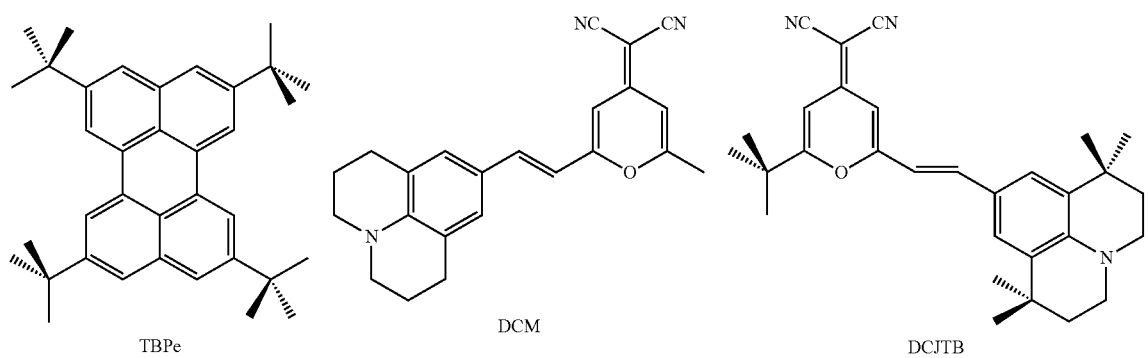

TBPe    DCM    DCJTB

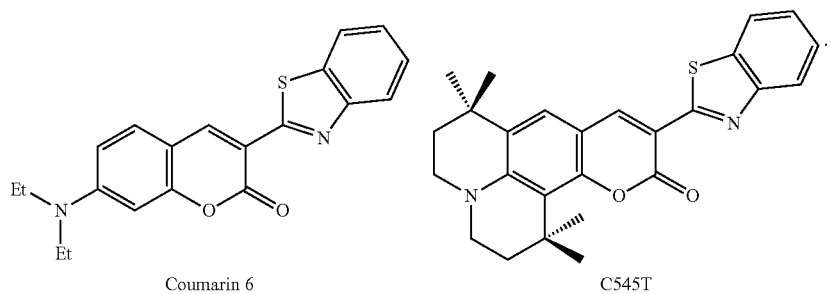

Coumarin 6    C545T

Alternatively, the fluorescent dopant may include a compound represented by Formula 501:

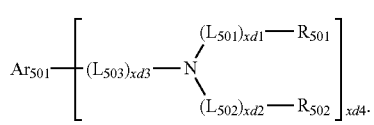

Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (e.g., a substituted silyl group), wherein $Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{501}$ to $L_{503}$ may be the same as defined in connection with $L_{301}$ herein, wherein $R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3, and xb4 may be selected from 1, 2, 3, and 4.

The fluorescent host may include at least one compound selected from compounds FD1 to FD8:

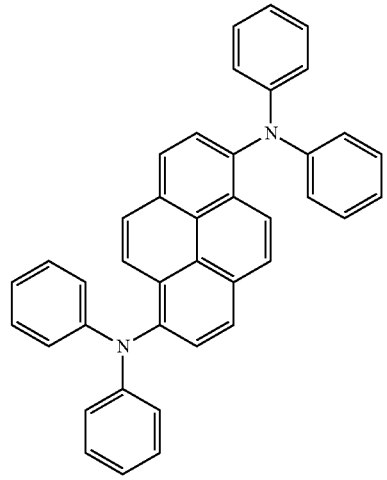

FD1

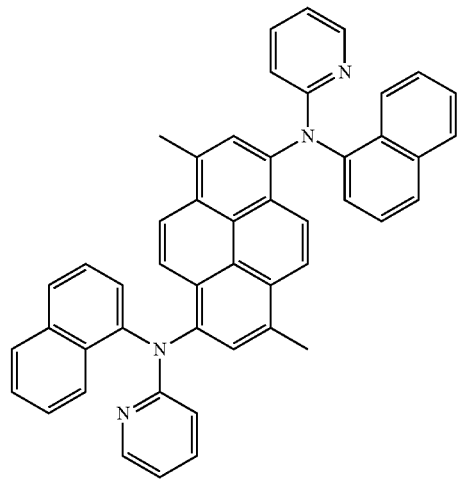

FD2

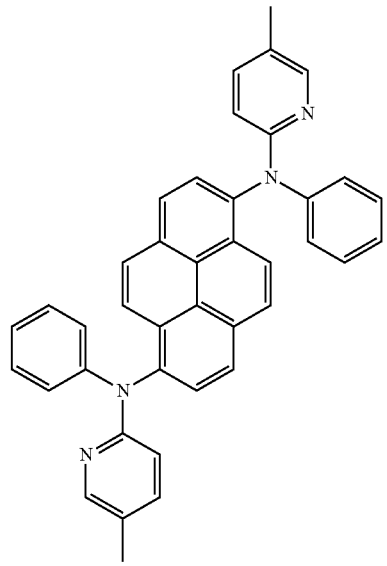

FD3

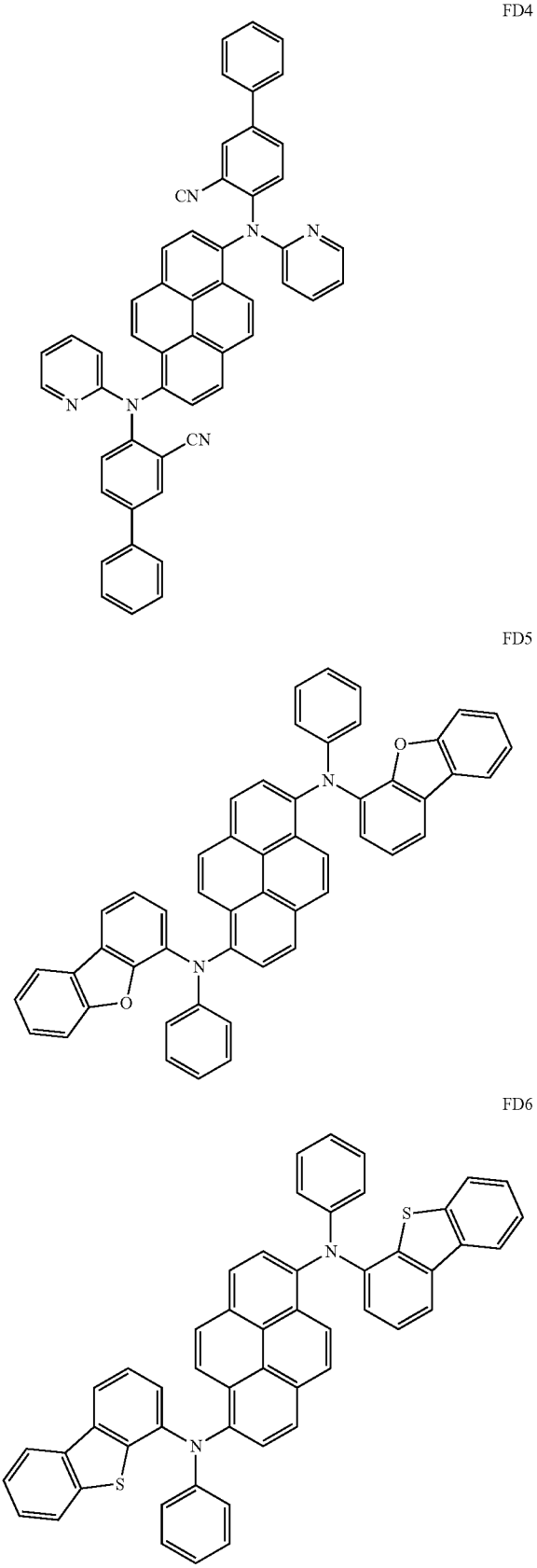

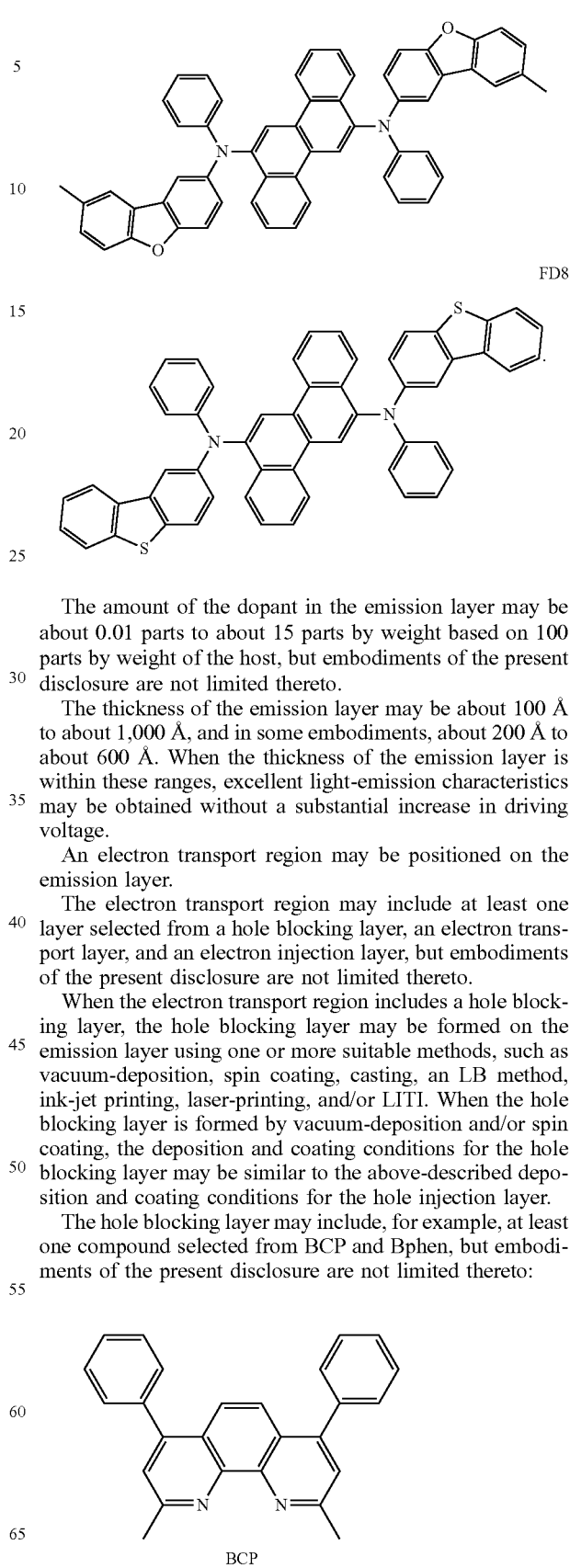

The amount of the dopant in the emission layer may be about 0.01 parts to about 15 parts by weight based on 100 parts by weight of the host, but embodiments of the present disclosure are not limited thereto.

The thickness of the emission layer may be about 100 Å to about 1,000 Å, and in some embodiments, about 200 Å to about 600 Å. When the thickness of the emission layer is within these ranges, excellent light-emission characteristics may be obtained without a substantial increase in driving voltage.

An electron transport region may be positioned on the emission layer.

The electron transport region may include at least one layer selected from a hole blocking layer, an electron transport layer, and an electron injection layer, but embodiments of the present disclosure are not limited thereto.

When the electron transport region includes a hole blocking layer, the hole blocking layer may be formed on the emission layer using one or more suitable methods, such as vacuum-deposition, spin coating, casting, an LB method, ink-jet printing, laser-printing, and/or LITI. When the hole blocking layer is formed by vacuum-deposition and/or spin coating, the deposition and coating conditions for the hole blocking layer may be similar to the above-described deposition and coating conditions for the hole injection layer.

The hole blocking layer may include, for example, at least one compound selected from BCP and Bphen, but embodiments of the present disclosure are not limited thereto:

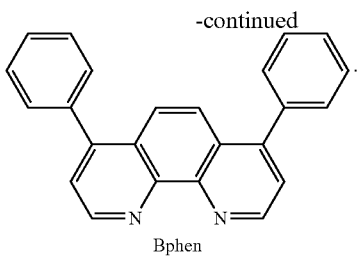

Bphen

The thickness of the hole blocking layer may be about 20 Å to about 1,000 Å, and in some embodiments, about 30 Å to about 300 Å. When the thickness of the hole blocking layer is within these ranges, excellent hole blocking characteristics may be obtained without a substantial increase in driving voltage.

The electron transport region may have a structure of electron transport layer/electron injection layer or a structure of hole blocking layer/electron transport layer/electron injection layer, wherein layers of each structure are sequentially stacked on the emission layer in these stated orders, but embodiments of the present disclosure are not limited thereto.

In some embodiments, the organic layer 150 of the organic light-emitting device may include an electron transport region between the emission layer and the second electrode 190, wherein the electron transport region may include an electron transport layer. The electron transport layer may include a plurality of layers. In some embodiments, the electron transport region may include a first electron transport layer and a second electron transport layer.

The electron transport layer may include at least one compound selected from BCP, Bphen, $Alq_3$, BAlq, TAZ, and NTAZ:

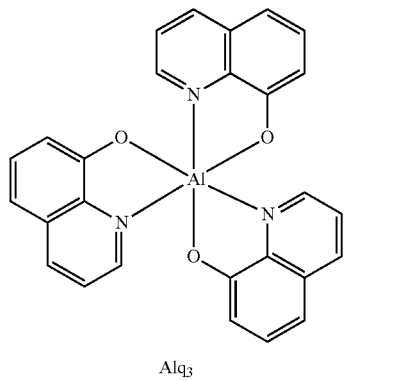

$Alq_3$

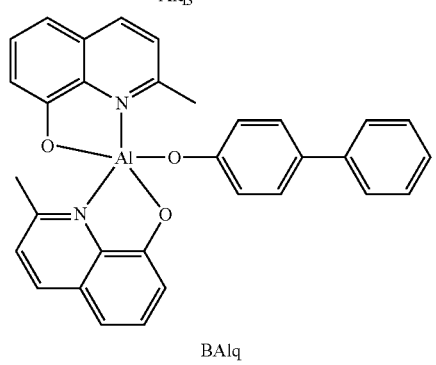

BAlq

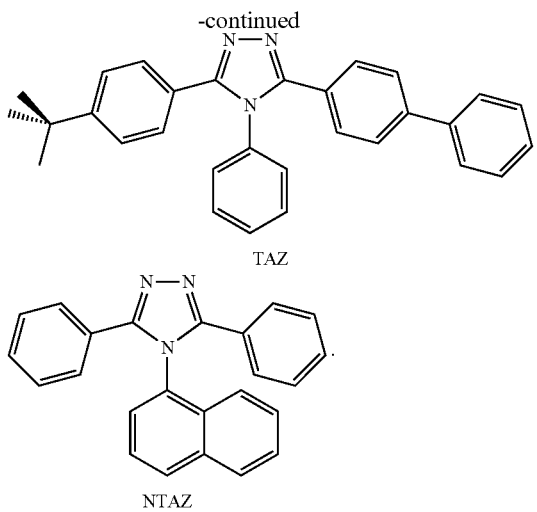

TAZ

NTAZ

In some embodiments, the electron transport layer may include at least one compound selected from a compound represented by Formula 601 and a compound represented by Formula 602:

$$Ar_{601}\text{-}[(L_{601})_{xe1}\text{-}E_{601}]_{xe2}.$$  Formula 601

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{301})(Q_{302})(Q_{303})$ (e.g., a substituted silyl group), wherein $Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group, the descriptions for $L_{601}$ may be the same as defined herein in connection with $L_{301}$, $E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, $xe1$ may be selected from 0, 1, 2, and 3, and $xe2$ may be selected from 1, 2, 3, and 4.

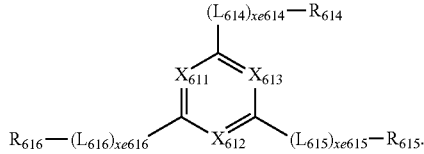

Formula 602

In Formula 602, $X_{611}$ may be selected from N and C-$(L_{611})_{xe611}$-$R_{611}$, $X_{612}$ may be selected from N and C-$(L_{612})_{xe612}$-$R_{612}$, $X_{613}$ may be selected from N and C-$(L_{613})_{xe613}$-$R_{613}$, and at least one atom selected from $X_{611}$ to $X_{613}$ may be N;

$L_{611}$ to $L_{616}$ may be the same as defined herein in connection with $L_{301}$;

$R_{611}$ to $R_{616}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and $xe611$ to $xe616$ may each independently be selected from 0, 1, 2, and 3.

The compound represented by Formula 601 and the compound represented by Formula 602 may each independently be selected from Compounds ET1 to ET15 illustrated below:

ET1
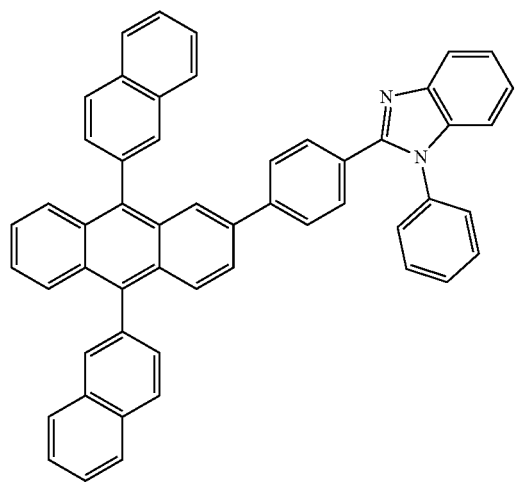
ET2
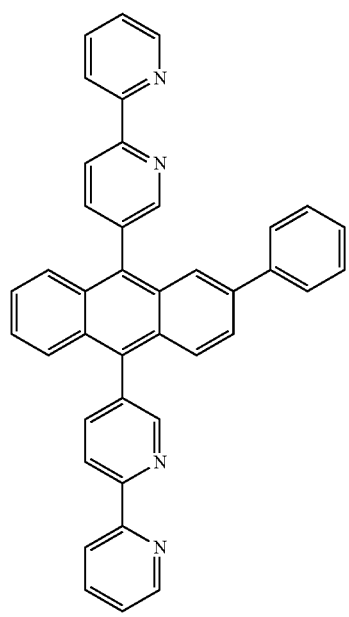
ET3
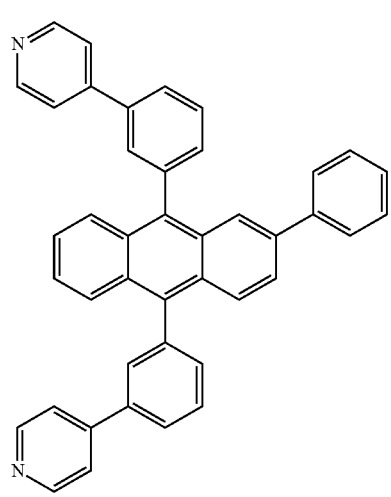
ET4
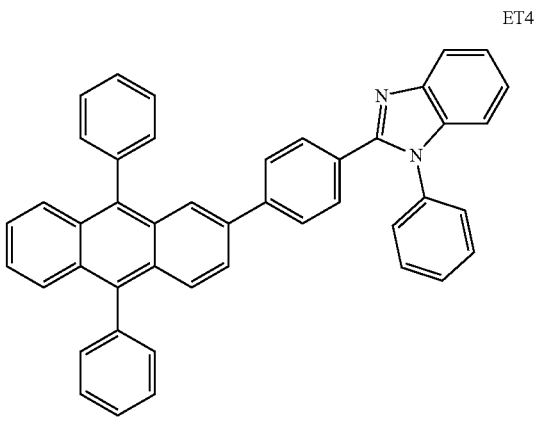
ET5
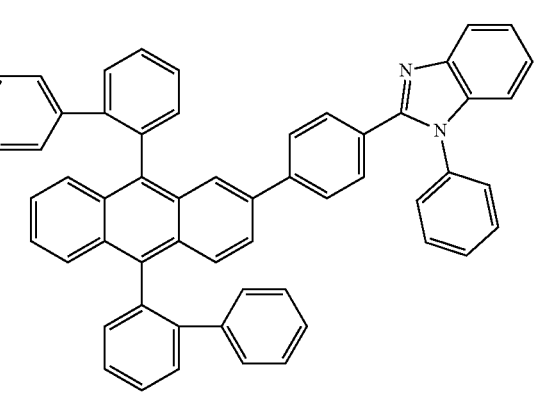
ET6
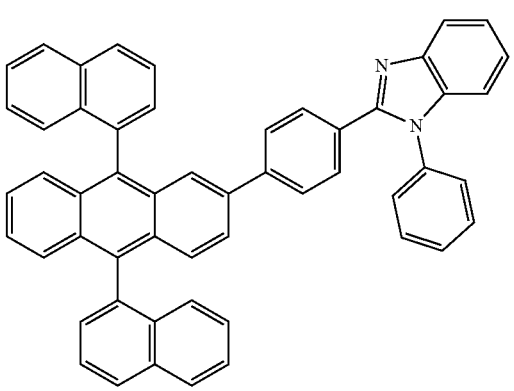

115
-continued
ET7
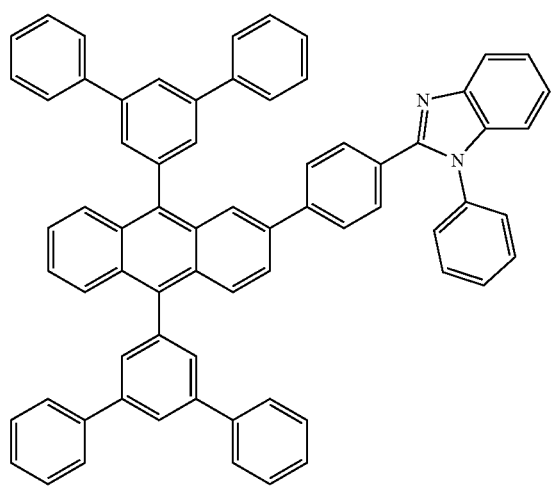
ET8
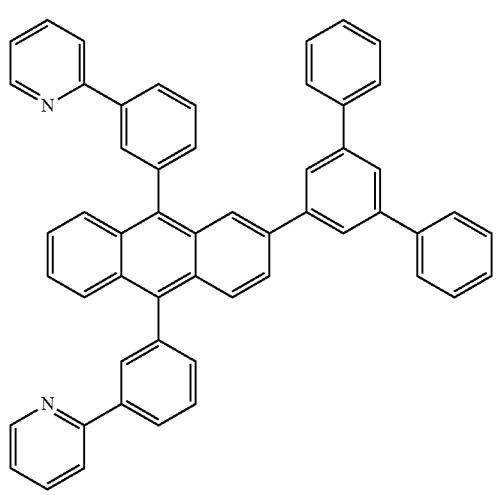
ET9
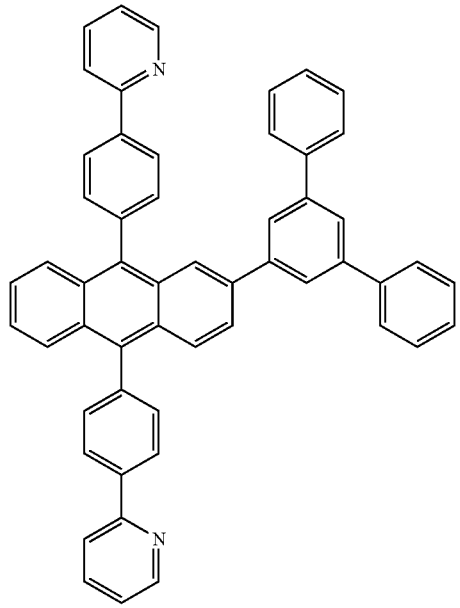
116
-continued
ET10
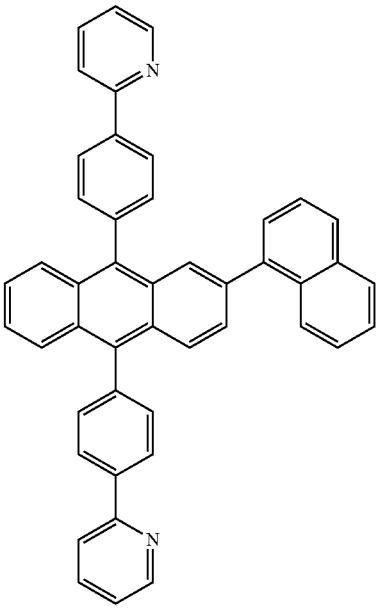
ET11
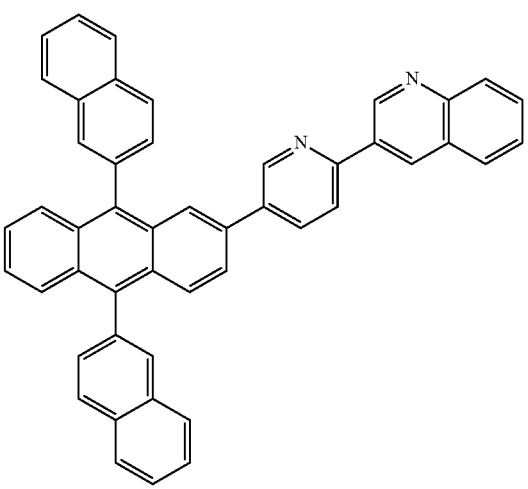
ET12
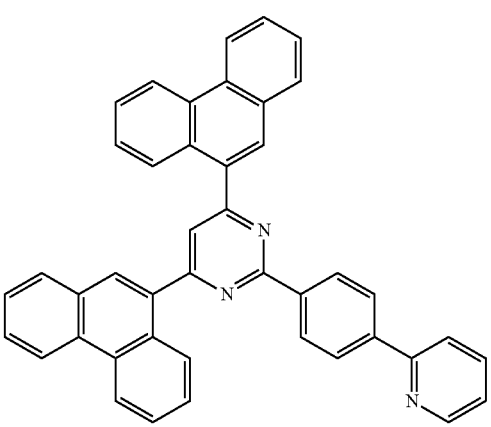

ET13

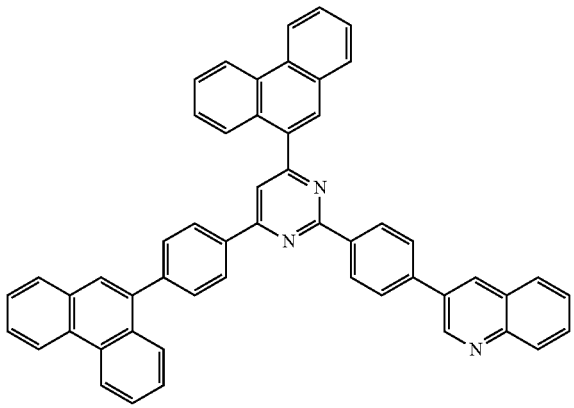

ET14

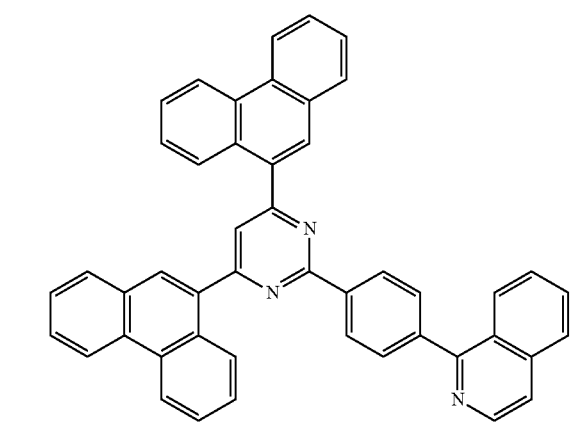

ET15

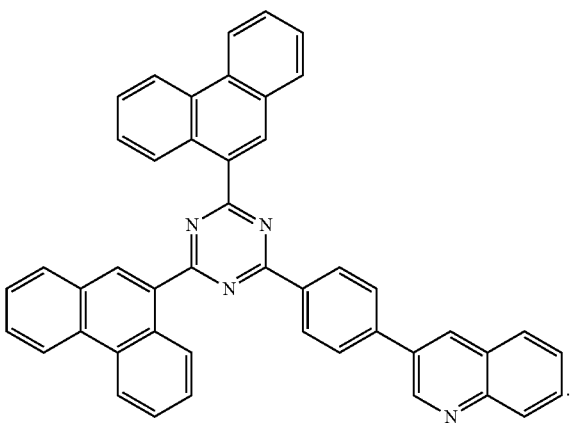

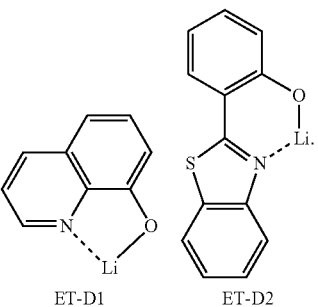

ET-D1   ET-D2

The thickness of the electron transport layer may be about 100 Å to about 1,000 Å, and in some embodiments, about 150 Å to about 500 Å. When the thickness of the electron transport layer is within these ranges, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) and/or ET-D2.

The electron transport region may include an electron injection layer that facilitates electron injection from the second electrode 190.

The electron injection layer may be formed on the electron transport layer using one or more suitable methods, such as vacuum-deposition, spin coating, casting, an LB method, ink-jet printing, laser-printing, and/or LITI. When the electron injection layer is formed by vacuum-deposition and/or spin coating, the vacuum-deposition and coating conditions for the electron injection layer may be similar to the vacuum-deposition and coating conditions for the hole injection layer.

The electron injection layer may include at least one compound selected from LiF, NaCl, CsF, $Li_2O$, BaO, and LiQ.

The thickness of the electron injection layer may be about 1 Å to about 100 Å, and in some embodiments, about 3 Å to about 90 Å. When the thickness of the electron injection layer is within these ranges, excellent electron injection characteristics may be obtained without a substantial increase in driving voltage.

The second electrode 190 is positioned on the organic layer 150. The second electrode 190 may be a cathode that is an electron injection electrode, and in this regard, the material for the second electrode may be a material having a low work function, and such a material may be metal, an alloy, an electrically conductive compound, and/or a mixture thereof. Non-limiting examples of the material for the second electrode may include lithium (Li), magnesium (Mg), aluminum (Al), aluminum-lithium (Al—Li), calcium (Ca), magnesium-indium (Mg—In), and magnesium-silver (Mg—Ag). In some embodiments, the second electrode material may be ITO or IZO. The second electrode 190 may be a reflective electrode, a semi-transmissive electrode, or a transmissive electrode.

In one or more embodiments, the organic layer of the organic light-emitting device may be formed by vacuum-depositing the compound or using a wet method in which the compound is prepared as a solution, and the solution of the compound is used for coating.

In one or more embodiments, the organic light-emitting device may be included in various types (e.g., kinds) of flat panel display apparatuses, for example, a passive matrix organic light-emitting display apparatus and an active matrix organic light-emitting display apparatus. When the organic light-emitting device is included in an active matrix organic light-emitting display apparatus, a first electrode positioned on a substrate may be a pixel electrode, and the first electrode may be electrically connected to a source electrode or drain electrode of a thin film transistor. In some embodiments, the organic light-emitting device may be included in a flat panel display apparatus that may display images on both sides.

Hereinbefore, the organic light-emitting device has been described with reference to the drawing, but embodiments of the present disclosure are not limited thereto.

Hereinafter, descriptions of representative substituents as used herein are as follows (carbon numbers defined for the substituents are non-limited and do not limit properties of the substituents, and substituents that are not defined herein may be defined according to their general description).

The term "$C_1$-$C_{60}$ alkyl group" as used herein may refer to a linear or branched aliphatic hydrocarbon monovalent group having 1 to 60 carbon atoms, and non-limiting examples thereof may include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein may refer to a divalent group having substantially the same structure as the $C_1$-$C_{60}$ alkyl group.

The term "$C_1$-$C_{60}$ alkoxy group" as used herein may refer to a monovalent group represented by —O-$A_{101}$ (wherein $A_{101}$ is a $C_1$-$C_{60}$ alkyl group), and non-limiting examples thereof may include a methoxy group, an ethoxy group, and an isopropyloxy group.

The term "$C_2$-$C_{60}$ alkenyl group" as used herein may refer to a hydrocarbon group formed by substituting at least one carbon-carbon double bond in the body (e.g., middle) or at the terminus of the $C_2$-$C_{60}$ alkyl group, and non-limiting examples thereof may include an ethenyl group, a propenyl group, and a butenyl group. The term "$C_2$-$C_{60}$ alkenylene group" as used herein may refer to a divalent group having substantially the same structure as a $C_2$-$C_{60}$ alkenyl group.

The term "$C_2$-$C_{60}$ alkynyl group" as used herein may refer to a hydrocarbon group formed by substituting at least one carbon-carbon triple bond in the body (e.g., middle) or at the terminus of the $C_2$-$C_{60}$ alkyl group, and non-limiting examples thereof may include an ethynyl group and a propynyl group. The term "$C_2$-$C_{60}$ alkynylene group" as used herein may refer to a divalent group having substantially the same structure as a $C_2$-$C_{60}$ alkynyl group.

The term "$C_3$-$C_{10}$ cycloalkyl group" as used herein may refer to a monovalent monocyclic saturated hydrocarbon group including 3 to 10 carbon atoms, and non-limiting examples thereof may include a cyclopropyl group, a cyclobutyl group, a cyclopentyl group, a cyclohexyl group, and a cycloheptyl group. The term "$C_3$-$C_{10}$ cycloalkylene group" as used herein may refer to a divalent group having substantially the same structure as a $C_3$-$C_{10}$ cycloalkyl group.

The term "$C_1$-$C_{10}$ heterocycloalkyl group" as used herein may refer to a monovalent monocyclic group including at least one heteroatom selected from N, O, phosphorus (P), and S as a ring-forming atom, and 1 to 10 carbon atoms. Non-limiting examples thereof may include a tetrahydrofuranyl group and a tetrahydrothiophenyl group. The term "$C_2$-$C_{10}$ heterocycloalkylene group" as used herein may refer to a divalent group having substantially the same structure as a $C_2$-$C_{10}$ heterocycloalkyl group.

The term "$C_3$-$C_{10}$ cycloalkenyl group" as used herein may refer to a monovalent monocyclic group including 3 to 10 carbon atoms and at least one double bond in the ring thereof and does not have aromaticity, and non-limiting examples thereof may include a cyclopentenyl group, a cyclohexenyl group, and a cycloheptenyl group. The term "$C_3$-$C_{10}$ cycloalkenylene group" as used herein may refer to a divalent group having substantially the same structure as a $C_3$-$C_{10}$ cycloalkenyl group.

The term "$C_2$-$C_{10}$ heterocycloalkenyl group" as used herein may refer to a monovalent monocyclic group including at least one heteroatom selected from N, O, P, and S as a ring-forming atom, 2 to 10 carbon atoms, and at least one double bond in its ring. Non-limiting examples of the $C_2$-$C_{10}$ heterocycloalkenyl group may include a 2,3-hydrofuranyl group and a 2,3-hydrothiophenyl group. The term "$C_2$-$C_{10}$ heterocycloalkenylene group" as used herein may refer to a divalent group having substantially the same structure as a $C_2$-$C_{10}$ heterocycloalkenyl group.

The term "$C_6$-$C_{60}$ aryl group" as used herein may refer to a monovalent group including a carbocyclic aromatic system having 6 to 60 carbon atoms, and the term "$C_6$-$C_{60}$ arylene group" as used herein may refer to a divalent group including a carbocyclic aromatic system having 6 to 60 carbon atoms. Non-limiting examples of the $C_6$-$C_{60}$ aryl group may include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the rings may be fused to each other.

The term "$C_1$-$C_{60}$ heteroaryl group" as used herein may refer to a monovalent group having a carbocyclic aromatic system that has at least one heteroatom selected from N, O, Si, P, and S as a ring-forming atom and 1 to 60 carbon atoms. The term "$C_1$-$C_{60}$ heteroarylene group" as used herein may refer to a divalent group having a carbocyclic aromatic system that has at least one heteroatom selected from N, O, P, and S as a ring-forming atom and 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein may indicate —O-$A_{102}$ (wherein $A_{102}$ is a $C_6$-$C_{60}$ aryl group), and the term "$C_6$-$C_{60}$ arylthio group" as used herein may indicate —S-$A_{103}$ (wherein $A_{103}$ is a $C_6$-$C_{60}$ aryl group).

The term "monovalent non-aromatic condensed polycyclic group" as used herein may refer to a monovalent group that has two or more rings condensed to each other, and has only carbon atoms (for example, the number of carbon atoms may be 8 to 60) as ring-forming atoms, wherein the molecular structure as a whole is non-aromatic in the entire molecular structure. A non-limiting example of the monovalent non-aromatic condensed polycyclic group is a fluorenyl group. The term "divalent non-aromatic condensed polycyclic group" as used herein may refer to a divalent group having substantially the same structure as the monovalent non-aromatic condensed polycyclic group.

The term "monovalent non-aromatic condensed heteropolycyclic group" as used herein may refer to a monovalent group that has two or more rings condensed to each other, has a heteroatom selected from N, O, P, and S in addition to 2 to 60 carbon atoms as ring-forming atoms, wherein the entire molecular structure is non-aromatic. The monovalent non-aromatic condensed heteropolycyclic group may include a carbazolyl group. The term "divalent non-aromatic condensed hetero-polycyclic group" as used herein may refer to a divalent group having substantially the same structure as the monovalent non-aromatic condensed heteropolycyclic group.

At least one of the substituents of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$) (e.g., a substituted amino group), —Si($Q_{13}$)($Q_{14}$)($Q_{15}$) (e.g., a substituted silyl group), and —B($Q_{16}$)($Q_{17}$) (e.g., a substituted boryl group);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_2$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$) (e.g., a substituted amino group), —Si($Q_{13}$)($Q_{14}$)($Q_{15}$) (e.g., a substituted silyl group), and —B($Q_{16}$)($Q_{17}$) (e.g., a substituted boryl group);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

As used herein, "Ph" may refer to a phenyl group, "Me" may refer to a methyl group, "Et" may refer to an ethyl group, and "ter-Bu" or "Bu$^t$" may refer to a tert-butyl group.

Hereinafter, an organic light-emitting device according to an embodiment of the present disclosure will be described in further detail with reference to Examples.

SYNTHESIS EXAMPLE

Synthesis Example 1

Synthesis of Compound 5

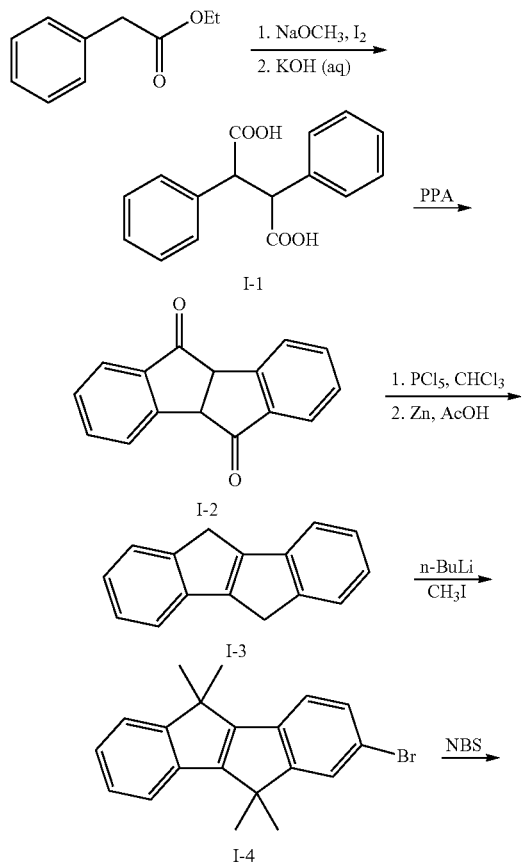

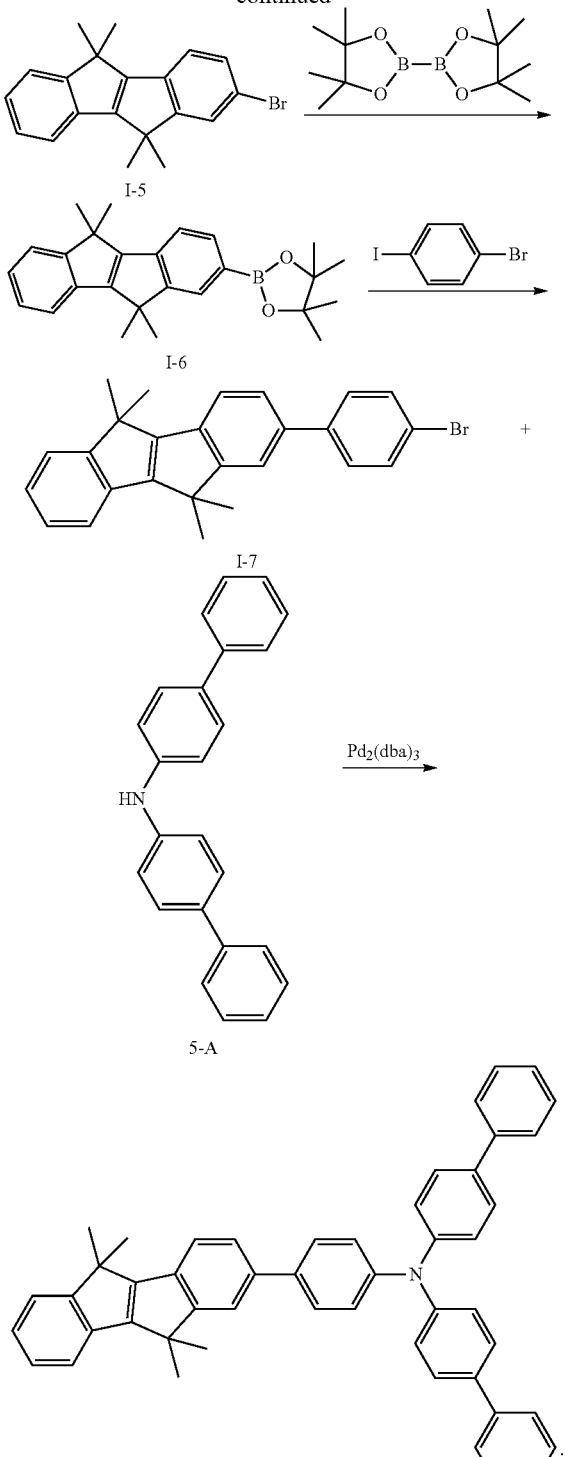

Synthesis of Intermediate I-1

2.54 g (10 mmol) of $I_2$ dissolved in 12 mL of THF was added to a reactant prepared by dissolving 3.3 mL (20 mmol) of ethyl phenyl acetate and 1.08 g (20 mmol) of $NaOCH_3$ in 25 mL of THF. The reaction solution was stirred at a temperature of −78° C. for 10 minutes, and then 5 ml of 5%

NaHSO$_4$ (aq) was added thereto at room temperature. 4.21 g (75 mmol) of KOH dissolved in 65 mL of water was added to the reaction solution, stirred at a temperature of 40° C. for 5 hours, and 5 mL of concentrated HCl was added thereto. The reaction solution was cooled at room temperature and filtered to obtain a precipitate, and then the precipitate was washed with 5 mL of water and dried under vacuum conditions for 24 hours to obtain 2.66 g of Intermediate I-1 (yield: 49%). The compound thus produced was confirmed by Mass Spectrometry/Fast Atom Bombardment (MS/FAB).

$C_{16}H_{14}O_4$: calc. 270.09, found 270.25.

Synthesis of Intermediate I-2

5.41 g (20 mmol) of Intermediate I-1 was added to 500 mL of a polyphosphoric acid (PPA) solution heated to a temperature of 100° C., and the resulting mixture was stirred at a temperature of 125° C. for 21 hours. Then, the reaction solution was further heated at a temperature of 150° C. for 2 hours. The reaction solution was cooled to 80° C., 600 mL of water was added thereto, the mixture was stirred for 2 hours, and the precipitate thus produced was filtered. The precipitate was dissolved in 140 mL of a hot NaHCO$_3$ aqueous solution and stirred for 30 minutes. The precipitate was isolated via filtration and dried under vacuum condition for 12 hours to obtain 4.03 g of Intermediate I-2 (yield: 86%). The compound thus obtained was confirmed by MS/FAB.

$C_{16}H_{10}O_2$: calc. 234.07, found 234.20.

Synthesis of Intermediate I-3

4.69 g (20 mmol) of Intermediate I-2 was dissolved in 20 mL of chloroform, and 8.75 g (42 mmol) of PCl$_5$ was added thereto and refluxed at a temperature of 50° C. for 30 minutes. The reaction solution was cooled to room temperature, the solvent was removed therefrom under vacuum conditions, the residue thus obtained was diluted with boiling acetic acid, and then 25 g of zinc dust was slowly added thereto. The resulting precipitate was filtered and washed with boiling acetic acid, and then the residue thus obtained was separated and purified using silica gel column chromatography to obtain 3.71 g of Intermediate I-3 (yield: 91%). The compound thus obtained was confirmed by MS/FAB.

$C_{16}H_{12}$: calc. 204.09, found 204.31.

Synthesis of Intermediate I-4

2.04 g (10 mmol) of Intermediate I-3 and 37.5 mL (60 mmol) of n-BuLi (1.60 M hexane solution) were slowly reacted in THF at a temperature of −78° C. for 10 minutes. 3.8 mL (60 mmol) of iodomethane was added to the reaction solution, stirred at room temperature for 3 hours, and 5 mL of 1N HCl (aq) was added thereto. From the reaction solution, the organic layer was separated, and the remaining water layer was extracted twice with 100 mL of dichloromethane to collect an organic layer. The organic layer thus collected was dried with magnesium sulfate, and the residue obtained after filtering and evaporating the solvent was separated and purified using silica gel column chromatography to obtain 2.03 g of Intermediate I-4 (yield: 78%). The compound thus produced was confirmed by MS/FAB.

$C_{20}H_{20}$: calc. 260.15, found 260.21.

Synthesis of Intermediate I-5

3.56 g (20 mmol) of N-bromosuccinimide (NBS) was completely dissolved in 50 mL of dimethylformamide (DMF), and 2.60 g (10 mmol) of Intermediate I-4 was added to the solution and stirred at room temperature for 24 hours. 50 mL of water was added to the solution, and an organic layer was obtained by extracting the reaction solution twice with 50 mL of dichloromethane. The organic layer thus collected was dried with magnesium sulfate, and the residue obtained after filtering and evaporating the solvent therefrom was separated and purified using silica gel column chromatography to obtain 2.55 g of Intermediate I-5 (yield: 61%). The compound thus produced was confirmed by MS/FAB.

$C_{20}H_{18}Br$: calc. 339.27, found 339.30.

Synthesis of Intermediate I-6

2.21 g (10.0 mmol) of Intermediate I-5, 2.54 g (10.0 mmol) of bis(pinacolato)diboron, 0.36 g (0.5 mmol) of PdCl$_2$(dppf)$_2$, and 2.94 g (30.0 mmol) of KOAc were dissolved in 40 mL of DMSO, and the mixture was stirred at a temperature of 80° C. for 6 hours. The reaction solution was cooled to room temperature, and 50 mL of water was added to the solution. An organic layer was obtained by extracting the reaction solution three times with 50 mL of diethyl ether and dried with magnesium sulfate, and the residue obtained after evaporating the solvent therefrom was separated and purified using silica gel column chromatography to obtain 3.09 g of Intermediate I-6 (yield: 80%). The compound thus produced was confirmed by MS/FAB.

$C_{26}H_{31}BO_2$: calc. 386.34, found 386.38.

Synthesis of Intermediate I-7

1.16 g (2.99 mmol) of Intermediate I-6, 0.93 g (3.29 mmol) of 4-bromoiodobenzene, 0.29 g (0.25 mmol) of tetrakis(triphenylphosphine)palladium (Pd(PPh$_3$)$_4$), and 0.62 g (4.48 mmol) of K$_2$CO$_3$ were dissolved in 60 mL of a THF/H$_2$O mixture solution (having a solvent ratio of THF/H$_2$O=2/1), and the mixture was stirred at a temperature of 70° C. for 5 hours. The reaction solution was cooled to room temperature, 40 mL of water was added to the solution, and an organic layer was obtained by extracting the reaction solution three times with 50 mL of ethyl ether. The organic layer thus collected was dried with magnesium sulfate, and the residue obtained after filtering and evaporating the solvent was separated and purified using silica gel column chromatography to obtain 0.96 g of Intermediate I-7 (yield: 74%). The compound thus produced was confirmed by MS/FAB.

$C_{26}H_{23}Br$: calc. 415.37, found 415.39.

Synthesis of Compound 5

8.31 g (20.0 mmol) of Intermediate I-7, 6.43 g (20.0 mmol) of Intermediate 5-A, 0.37 g (0.4 mmol) of Pd$_2$(dba)$_3$, 0.08 g (0.4 mmol) of P(t-Bu)$_3$, and 5.76 g (60.0 mmol) of t-BuOK were dissolved in 90 mL of toluene, and the mixture was stirred at a temperature of 85° C. for 12 hours. The reaction solution was cooled to room temperature, 50 mL of water was added to the solution, and an organic layer was obtained by extracting three times with 50 mL of diethyl ether. The organic layer thus collected was dried with magnesium sulfate, and the residue obtained after filtering and evaporating the solvent was separated and purified using silica gel column chromatography to obtain 10.9 g of Compound 5 (yield: 83%). The compound thus produced was confirmed using $^1$H NMR (CDCl$_3$, 400 MHz) and MS/FAB.

δ=9.26 (s, 1H), 8.46 (s, 1H), 8.23 (s, 1H), 7.78 (s, 1H), 7.60-7.46 (m, 12H), 7.29-6.78 (m, 14H), 6.65-6.60 (m, 3H), 6.48-6.40 (m, 1H), 6.25-6.20 (m, 2H), 6.00-5.98 (m, 2H), 2.55 (s, 3H), 2.50 (s, 3H)

$C_{50}H_{41}N$: calc. 655.88, found 655.90.

Synthesis Example 2

Synthesis of Compound 10

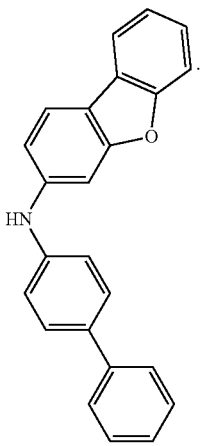

10-A

Compound 10 was synthesized in a similar manner as Compound 5, except that Intermediate 10-A was used instead of Intermediate 5-A. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{50}H_{39}NO$: calc. 869.86, found 869.87.

Synthesis Example 3

Synthesis of Compound 14

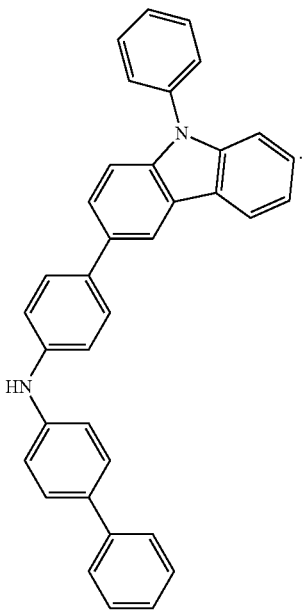

14-A

Compound 14 was synthesized in a similar manner as Compound 5, except that Intermediate 14-A was used instead of Intermediate 5-A. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{62}H_{48}N_2$: calc. 821.08, found 821.11.

Synthesis Example 4

Synthesis of Compound 19

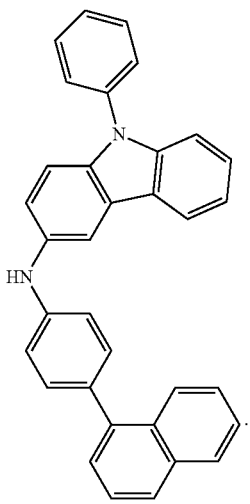

19-A

Compound 19 was synthesized in a similar manner as Compound 5, except that Intermediate 19-A was used instead of Intermediate 5-A. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{60}H_{46}N_2$: calc. 795.04, found 795.06.

Synthesis Example 5

Synthesis of Compound 24

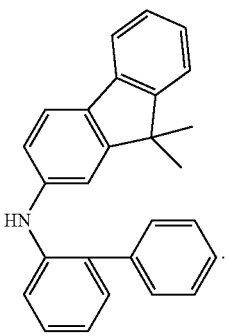

24-A

Compound 24 was synthesized in a similar manner as Compound 5, except that Intermediate 24-A was used instead of Intermediate 5-A. The compound thus produced was confirmed by using $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

C$_{53}$H$_{45}$N: calc. 695.95, found 695.98.

Synthesis Example 6

Synthesis of Compound 28

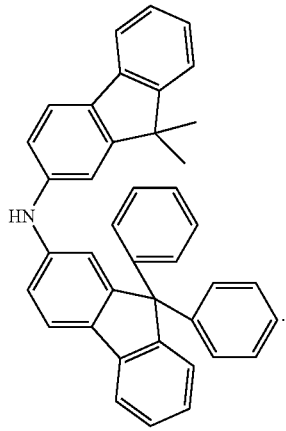

28-A

Compound 28 was synthesized in a similar manner as Compound 5, except that Intermediate 28-A was used instead of Intermediate 5-A. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

C$_{66}$H$_{53}$N: calc. 860.15, found 860.16.

Synthesis Example 7

Synthesis of Compound 31

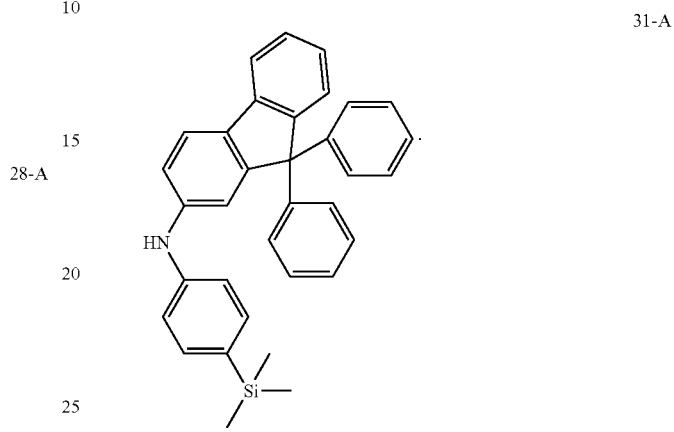

31-A

Compound 31 was synthesized in a similar manner as Compound 5, except that Intermediate 31-A was used instead of Intermediate 5-A. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

C$_{60}$H$_{53}$NSi: calc. 816.17, found 816.19.

Synthesis Example 8

Synthesis of Compound 39

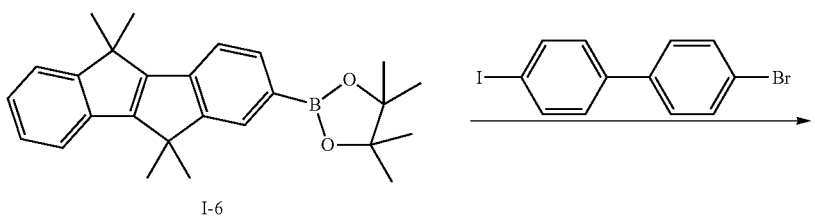

I-6

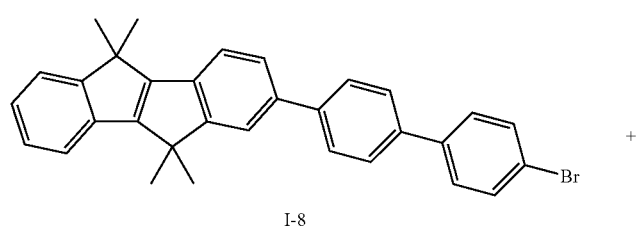

I-8

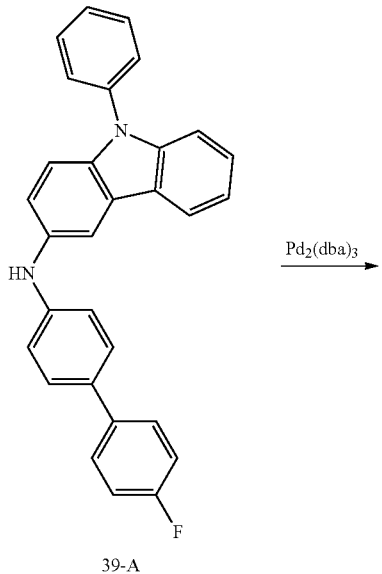

39-A

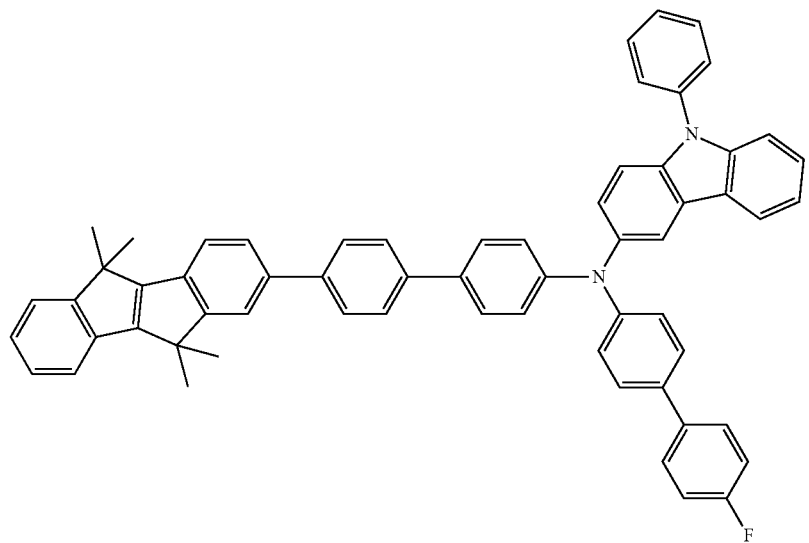

39

Intermediate I-8 was synthesized in a similar manner as Intermediate I-7, except that 4-bromo-4'-iodo-1,1'-biphenyl was used instead of 4-bromoiodobenzene. Compound 39 was synthesized in a similar manner as Compound 5, except that Intermediate I-8 was used instead of Intermediate I-7, and Intermediate 39-A was used instead of Intermediate 5-A in the final Pd$_2$(dba)$_3$ coupling. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

C$_{62}$H$_{47}$FN$_2$: calc. 839.07, found 839.09.

Synthesis Example 9

Synthesis of Compound 43

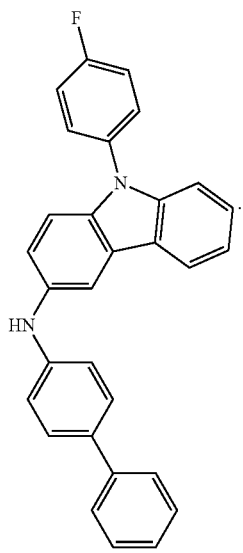

43-A

Compound 43 was synthesized in a similar manner as Compound 5, except that Intermediate I-5 was used instead of Intermediate I-7, and Intermediate 43-A was used instead of Intermediate 5-A in the final $Pd_2(dba)_3$ coupling. The compound thus produced was confirmed by $^1H$ NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{50}H_{39}FN_2$: calc. 686.87, found 686.90.

Synthesis Example 10

Synthesis of Compound 48

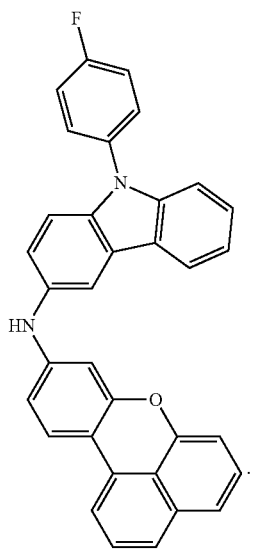

48-A

Compound 48 was synthesized in substantially the same manner as used in the synthesis of Compound 5, except that Intermediate I-5 was used instead of Intermediate I-7, and Intermediate 48-A was used instead of Intermediate 5-A in the final $Pd_2(dba)_3$ coupling. The compound thus produced was confirmed by $^1H$ NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{54}H_{39}FN_2O$: calc. 750.91, found 750.99.

Synthesis Example 11

Synthesis of Compound 51

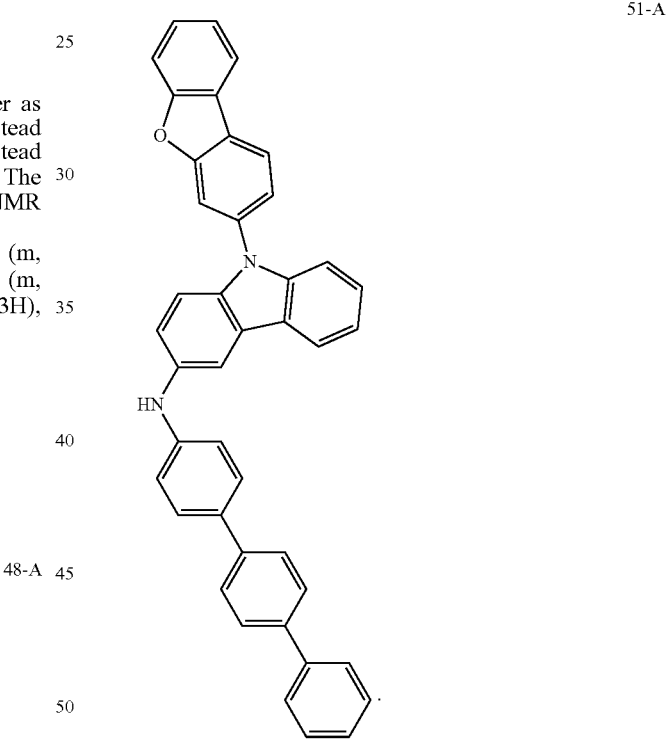

51-A

Compound 51 was synthesized in substantially the same manner as used in the synthesis of Compound 5, except that Intermediate I-5 was used instead of Intermediate I-7, and Intermediate 51-A was used instead of Intermediate 5-A in the final $Pd_2(dba)_3$ coupling. The compound thus produced was confirmed by using $^1H$ NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{62}H_{46}FN_2$: calc. 835.06, found 835.07.

Synthesis Example 12

Synthesis of Compound 54

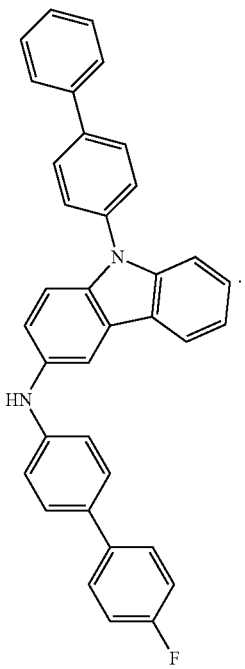

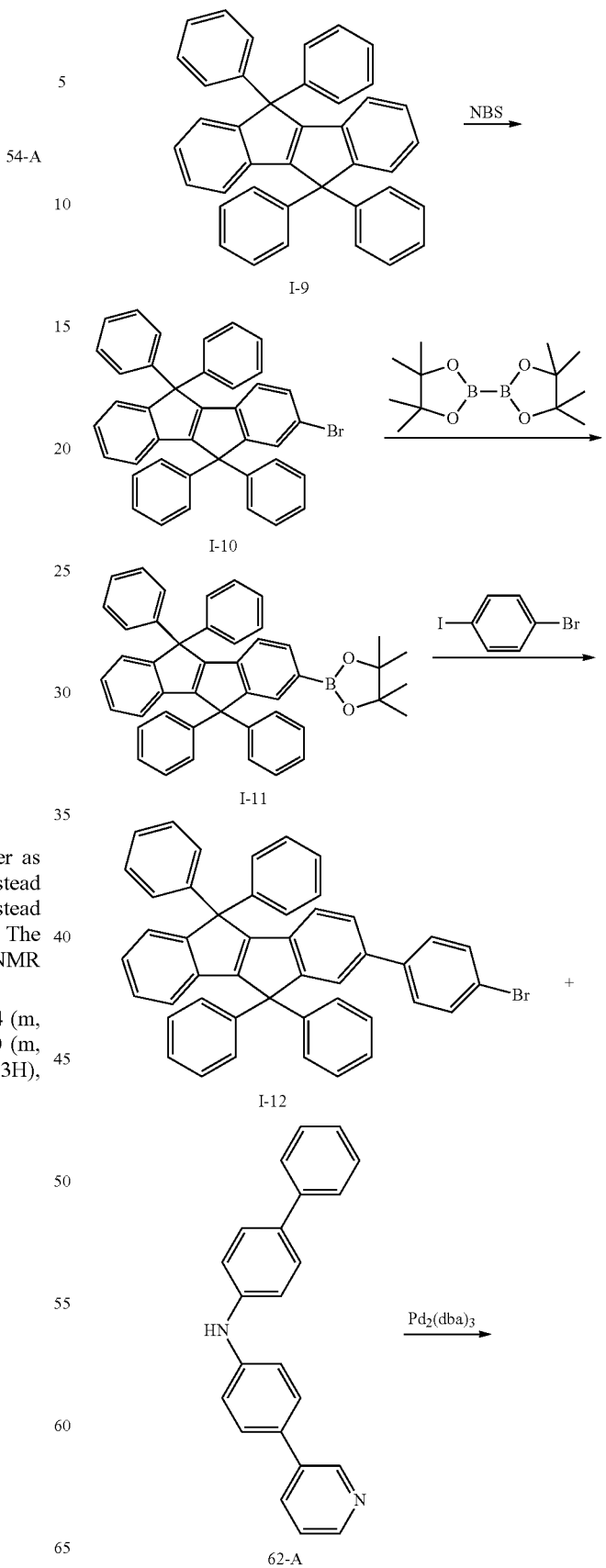

Compound 54 was synthesized in a similar manner as Compound 5, except that Intermediate I-5 was used instead of Intermediate I-7, and Intermediate 54-A was used instead of Intermediate 5-A in the final $Pd_2(dba)_3$ coupling. The compound thus produced was confirmed by using $^1$H NMR ($CDCl_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{56}H_{43}FN_2$: calc. 762.97, found 762.99.

Synthesis Example 13

Synthesis of Compound 62

-continued

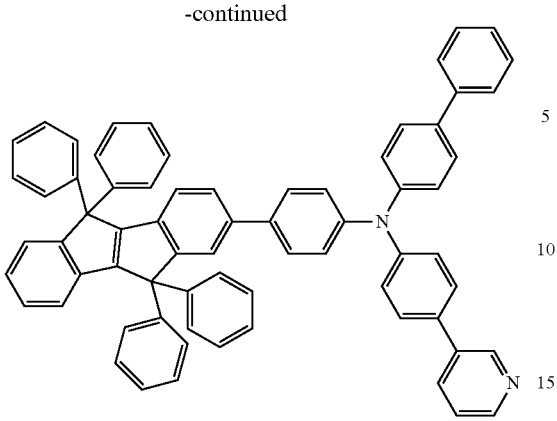

62

Synthesis of Intermediate I-9

20.4 g (100 mmol) of Intermediate I-3 was dissolved in 100 mL of toluene under a nitrogen atmosphere, and 51.0 g (250 mmol) of iodobenzene was added thereto and stirred for 10 minutes. Then, 280 mg (1 mmol) of tricyclohexylphosphine, 224 mg (1 mmol) of Pd(OAc)$_2$, and 336 g (300 mmol) of t-BuOK were added thereto, stirred at a temperature of 130° C. for 12 hours, and cooled to room temperature. 100 mL of water was added to the reaction solution, and an organic layer was thrice extracted therefrom with 100 mL of toluene. The organic layer thus collected was dried with magnesium sulfate, and the residue obtained after filtering and evaporating the solvent therefrom was separated and purified using silica gel column chromatography to obtain 46 g of Intermediate I-9 (yield: 91%). The compound thus produced was confirmed by MS/FAB.

$C_{40}H_{28}$: calc. 508.66, found 508.68.

Synthesis of Intermediate I-10

Intermediate I-10 was synthesized in a similar manner as Intermediate I-5, except that Intermediate I-9 was used instead of Intermediate I-4. The compound thus produced was confirmed by MS/FAB.

$C_{40}H_{27}Br$: calc. 587.56, found 587.57.

Synthesis of Intermediate I-11

Intermediate I-11 was synthesized in a similar manner as Intermediate I-6, except that Intermediate I-10 was used instead of Intermediate I-5. The compound thus produced was confirmed by using MS/FAB.

$C_{46}H_{39}BO_2$: calc. 634.62, found 634.66.

Synthesis of Intermediate I-12

Intermediate I-12 was synthesized in a similar manner as Intermediate I-7, except that Intermediate I-11 was used instead of Intermediate I-6. The compound thus produced was confirmed by MS/FAB.

$C_{46}H_{31}Br$: calc. 663.65, found 663.67.

Synthesis of Compound 62

Compound 62 was synthesized in a similar manner as Compound 5, except that Intermediate I-12 was used instead of Intermediate I-7, and Intermediate 62-A was used instead of Intermediate 5-A in the final Pd$_2$(dba)$_3$ coupling. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{69}H_{48}N_2$: calc. 905.15, found 905.16.

Synthesis Example 14

Synthesis of Compound 66

-continued

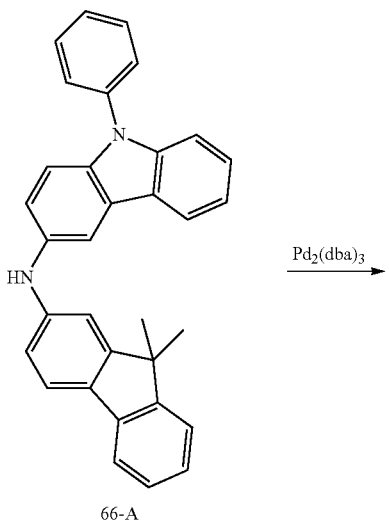

66-A

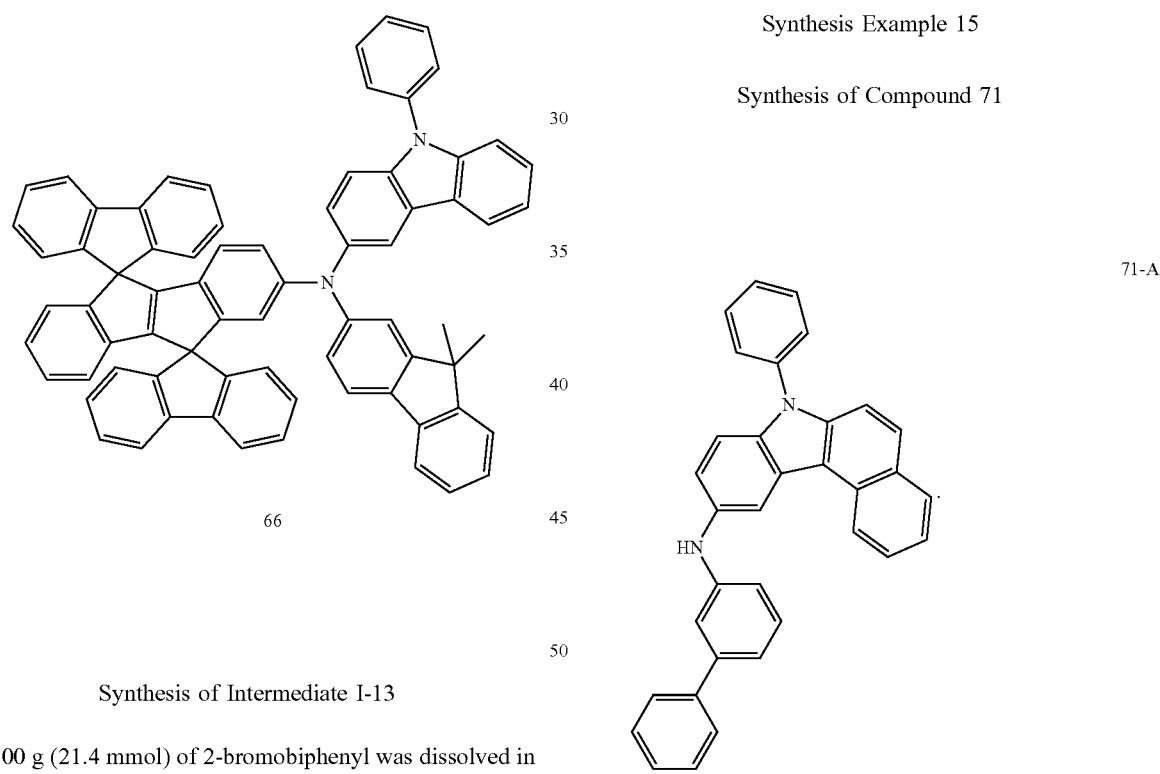

66

Synthesis of Intermediate I-13

5.00 g (21.4 mmol) of 2-bromobiphenyl was dissolved in 11.0 mL of THF, and 0.57 g (23.3 mmol) of magnesium was added thereto at room temperature. When a Grignard reactant was produced, a solution prepared by dissolving 5.06 g (21.4 mmol) of Intermediate I-2 in 5 mL of THF was added thereto dropwise. The mixture was stirred at a temperature of 85° C. for 4 hours and cooled to room temperature to produce a yellow precipitate, and the precipitate was washed with methanol to obtain 6.83 g of Intermediate I-13 (yield: 63%). The compound thus produced was confirmed by MS/FAB.

$C_{40}H_{26}$: calc. 506.64, found 506.65.

Synthesis of Intermediate I-14

Intermediate I-14 was synthesized in a similar manner as Intermediate I-5, except that Intermediate I-13 was used instead of Intermediate I-4. The compound thus produced was confirmed by MS/FAB.

$C_{40}H_{25}Br$: calc. 585.54, found 585.55.

Synthesis of Compound 66

Compound 66 was synthesized in a similar manner as Compound 5, except that Intermediate I-14 was used instead of Intermediate I-7, and Intermediate 66-A was used instead of Intermediate 5-A in the final $Pd_2(dba)_3$ coupling. The compound thus produced was confirmed by $^1$H NMR ($CDCl_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{73}H_{48}N_2$: calc. 953.20, found 953.22.

Synthesis Example 15

Synthesis of Compound 71

71-A

Compound 71 was synthesized in a similar manner as Compound 5, except that Intermediate 71-A was used instead of Intermediate 5-A in the final $Pd_2(dba)_3$ coupling. The compound thus produced was confirmed by using $^1$H NMR ($CDCl_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{60}H_{46}N_2$: calc. 795.04, found 795.05.

Synthesis Example 16

Synthesis of Compound 76

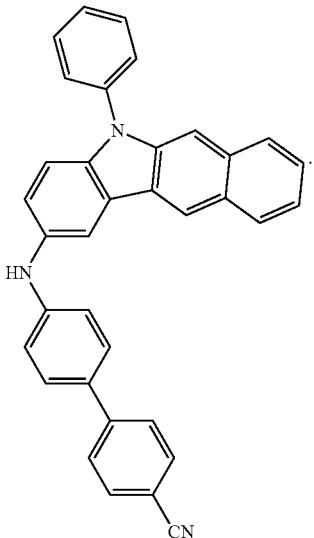

76-A

Compound 76 was synthesized in a similar manner as Compound 5, except that Intermediate 76-A was used instead of Intermediate 5-A. The compound thus produced was confirmed by $^1$H NMR (CDCl$_3$, 400 MHz) and MS/FAB.

δ=9.26 (s, 1H), 8.48 (s, 1H), 8.23 (s, 1H), 7.90-7.74 (m, 9H), 7.50-7.25 (m, 5H), 7.18-6.90 (m, 9H), 6.74-6.50 (m, 4H), 6.25-6.20 (m, 2H), 6.15-6.10 (m, 2H), 2.75 (s, 3H), 2.70 (s, 3H)

$C_{61}H_{45}N_3$: calc. 820.05, found 820.06.

The compounds were identified by $^1$H NMR and MS/FAB. The results thereof are shown in Table 1.

The synthetic methods used to prepare compounds other than the compounds shown in Table 1 may be understood by one of ordinary skill in the art by referring to the synthetic pathways and raw materials used in Synthesis Examples 1 to 16.

TABLE 1

| Compound | $^1$H NMR (CDCl$_3$, 400 MHz) | MS/FAB found | MS/FAB calc. | Yield (%) |
|---|---|---|---|---|
| 2 | δ = 8.25-8.22 (m, 1H), 7.89-7.84 (m, 2H), 7.60-7.29 (m, 19H), 6.92-6.84 (m, 3H), 6.60-6.54 (m, 2H), 1.50 (s, 6H), 1.46 (m, 6H) | 629.86 | 629.84 | 78 |
| 5 | δ = 8.15-8.12 (m, 1H), 7.87-7.84 (m, 1H), 7.56-7.52 (m, 6H), 7.48-7.25 (m, 14H), 7.28-7.25 (m, 1H), 6.80-6.74 (m, 6H), 1.50 (s, 6H), 1.46 (m, 6H) | 655.90 | 655.88 | 83 |
| 7 | δ = 8.15-8.12 (m, 1H), 7.97 (d, 1H), 7.76-7.72 (m, 1H), 7.60-7.55 (m, 4H), 7.48-7.20 (m, 12H), 7.13-7.08 (m, 2H), 6.75 (d, 1H), 6.54-6.45 (m, 5H), 1.53 (s, 6H), 1.50 (s, 6H), 1.46 (m, 6H) | 695.96 | 695.95 | 75 |
| 10 | δ = 8.15-8.12 (m, 1H), 7.87-7.75 (m, 3H), 7.60-7.52 (m, 5H), 7.48-7.20 (m, 12H), 6.98-6.95 (m, 2H), 6.73-6.70 (m, 2H), 6.68-6.62 (m, 2H), 1.47 (s, 6H), 1.44 (s, 6H) | 869.88 | 869.87 | 85 |
| 12 | δ = 8.20-8.18 (m, 1H), 8.15-8.10 (m, 2H), 7.87-7.85 (m, 2H), 7.58-7.53 (m, 4H), 7.48-7.25 (m, 11H), 7.22-7.20 (m, 1H), 7.15-7.13 (m, 1H), 7.06 (dd, 1H), 6.75-6.60 (m, 4H), 1.50 (s, 6H), 1.46 (s, 6H) | 685.93 | 685.92 | 88 |
| 13 | δ = 8.22-8.20 (m, 1H), 8.14-8.11 (m, 1H), 7.85-7.83 (m, 1H), 7.60-7.20 (m, 24H), 6.86-6.84 (m, 2H), 6.68-6.62 (m, 3H), 1.50 (s, 6H), 1.46 (m, 6H) | 743.99 | 743.98 | 81 |
| 14 | δ = 8.25-8.22 (m, 1H), 8.15-8.12 (m, 1H), 8.05-8.03 (m, 1H), 7.85 (d, 1H), 7.75-7.73 (m, 1H), 7.68 (dd, 1H), 7.58-7.18 (m, 24H), 6.87-6.82 (m, 4H), 6.65-6.60 (m, 2H), 1.42 (s, 6H), 1.38 (s, 6H) | 821.11 | 821.08 | 74 |
| 15 | δ = 8.15-8.10 (m, 3H), 7.86 (d, 1H), 7.60-7.55 (m, 4H), 7.48-7.21 (m, 18H), 6.86-6.80 (m, 4H), 6.72-6.68 (m, 2H), 1.42 (s, 6H), 1.38 (s, 6H) | 745.01 | 744.98 | 80 |
| 16 | δ = 8.20-8.18 (m, 1H), 8.15-8.13 (m, 1H), 7.84 (d, 1H), 7.58-7.46 (m, 6H), 7.43-7.25 (m, 13H), 6.86-7.83 (m, 2H), 6.68-6.65 (m, 2H), 6.60 (dd, 1H), 1.50 (s, 6H), 1.46 (s, 6H), 0.25 (s, 9H) | 741.07 | 741.06 | 77 |
| 17 | δ = 8.83-8.80 (m, 1H), 8.45-8.42 (m, 1H), 8.22-8.20 (m, 1H), 8.14-8.12 (m, 1H), 7.96-7.94 (m, 1H), 7.85 (d, 1H), 7.58-7.46 (m, 6H), 7.42-7.20 (m, 14H), 6.85-6.74 (m, 4H), 6.61 (dd, 1H), 1.50 (s, 6H), 1.46 (s, 6H) | 745.98 | 745.97 | 77 |
| 19 | δ = 8.23-8.20 (m, 1H), 8.15-8.12 (m, 1H), 7.87-7.85 (m, 2H), 7.75-7.70 (m, 1H), 7.65-7.62 (m, 1H), 7.57-7.45 (m, 10H), 7.45-7.20 (m, 12H), 7.05-7.00 (m, 1H), 6.88-6.83 (m, 2H), 6.57 (dd, 1H), 6.46-6.43 (m, 2H), 1.42 (s, 6H), 1.36 (s, 6H) | 795.06 | 795.04 | 71 |
| 21 | δ = 8.23-8.20 (m, 1H), 8.17-8.14 (m, 1H), 7.96 (d, 1H), 7.77-7.73 (m, 2H), 7.58-7.52 (m, 2H), | 785.05 | 785.04 | 80 |

TABLE 1-continued

| Compound | ¹H NMR (CDCl₃, 400 MHz) | MS/FAB found | MS/FAB calc. | Yield (%) |
|---|---|---|---|---|
|  | 7.52-7.22 (m, 16H), 7.13-7.10 (m, 2H), 6.96 (dd, 1H), 6.75 (dd, 1H), 6.56-6.50 (m, 3H), 1.52 (s, 6H), 1.46 (s, 6H), 1.38 (s, 6H) |  |  |  |
| 22 | δ = 8.23-8.20 (m, 1H), 8.17-8.14 (m, 1H), 7.87-7.84 (m, 2H), 7.58-7.54 (m, 2H), 7.51-7.10 (m, 28H), 6.80-6.78 (m, 1H), 6.70 (dd, 1H), 6.57-6.50 (m, 4H), 1.42 (s, 6H), 1.30 (s, 6H) | 909.19 | 909.18 | 73 |
| 24 | δ = 8.15-8.12 (m, 1H), 7.86 (d, 1H), 7.76 (d, 1H), 7.60-7.10 (m, 18H), 7.00-6.95 (m, 1H), 6.60 (dd, 1H), 6.35-6.32 (m, 3H), 6.25-6.22 (m, 1H), 1.61 (s, 6H), 1.46 (s, 6H), 1.38 (s, 6H) | 695.98 | 695.95 | 77 |
| 27 | δ = 8.15-8.12 (m, 1H), 7.85 (d, 1H), 7.77-7.73 (m, 2H), 7.58-7.52 (m, 2H), 7.46-7.22 (m, 9H), 7.13-7.10 (m, 4H), 6.73-6.70 (m, 2H), 6.46-6.42 (m, 4H), 1.61 (s, 12H), 1.46 (s, 6H), 1.38 (s, 6H) | 736.04 | 736.01 | 74 |
| 28 | δ = 8.15-8.12 (m, 1H), 7.87-7.84 (m, 2H), 7.75-7.72 (m, 1H), 7.58-7.52 (m, 2H), 7.46-7.10 (m, 22H), 6.80-6.78 (m, 1H), 6.75-6.70 (m, 2H), 6.53-6.52 (m, 1H), 6.46-6.42 (m, 3H), 1.56 (s, 6H), 1.46 (s, 6H), 1.38 (s, 6H) | 860.16 | 860.15 | 85 |
| 31 | δ = 8.16-8.14 (m, 1H), 7.87-7.84 (m, 2H), 7.58-7.54 (m, 2H), 7.46-7.14 (m, 20H), 6.82-6.70 (m, 4H), 6.60-6.54 (m, 2H), 6.42-6.40 (m, 1H), 1.42 (s, 6H), 1.38 (s, 6H), 0.26 (s, 9H) | 816.19 | 816.17 | 86 |
| 32 | δ = 8.15-8.12 (m, 1H), 7.87-7.84 (m, 2H), 7.58-7.54 (m, 2H), 7.46-7.38 (m, 3H), 7.32-7.15 (m, 15H), 6.97-6.90 (m, 2H), 6.82-6.70 (m, 4H), 6.56-6.52 (m, 2H), 6.42-6.40 (m, 1H), 1.46 (s, 6H), 1.38 (s, 6H) | 761.99 | 761.98 | 89 |
| 36 | δ = 8.15-8.12 (m, 1H), 8.10-8.05 (m, 1H), 7.96-7.90 (m, 1H), 7.82-7.80 (m, 2H), 7.65-7.55 (m, 5H), 7.52-7.25 (m, 16H), 6.92 (d, 1H), 6.47-6.43 (m, 4H), 1.46 (s, 6H), 1.40 (s, 6H) | 705.97 | 705.94 | 90 |
| 37 | δ = 8.15-8.12 (m, 1H), 7.87-7.85 (m, 1H), 7.73-7.65 (m, 4H), 7.60-7.55 (m, 4H), 7.48-7.26 (m, 17H), 6.85-6.80 (m, 4H), 6.62-6.58 (m, 2H), 1.46 (s, 6H), 1.40 (s, 6H) | 731.99 | 731.98 | 84 |
| 39 | δ = 8.22-8.20 (m, 1H), 8.15-8.13 (m, 1H), 7.87-7.85 (m, 1H), 7.73-7.65 (m, 4H), 7.53-7.23 (m, 21H), 7.06-7.00 (m, 2H), 6.72-6.68 (m, 4H), 6.60-6.54 (m, 1H), 1.42 (s, 6H), 1.30 (s, 6H) | 839.10 | 839.09 | 82 |
| 41 | δ = 8.20-8.18 (m, 1H), 8.17-8.15 (m, 1H), 7.92-7.85 (m, 4H), 7.75-7.68 (m, 4H), 7.50-7.15 (m, 24H), 6.90 (d, 1H), 6.76-6.72 (m, 3H), 6.64-6.60 (m, 2H), 6.52-6.48 (m, 2H), 1.46 (s, 6H), 1.40 (s, 6H) | 983.33 | 983.27 | 86 |
| 43 | δ = 8.23-8.20 (m, 1H), 8.15-8.12 (m, 1H), 7.87-7.85 (m, 1H), 7.60-7.55 (m, 2H), 7.48-7.23 (m, 15H), 7.10-7.04 (m, 4H), 6.95 (dd, 1H), 6.60-6.55 (m, 2H), 1.42 (s, 6H), 1.40 (s, 6H) | 686.90 | 686.87 | 76 |
| 44 | δ = 8.23-8.20 (m, 1H), 8.15-8.12 (m, 1H), 7.85-7.80 (m, 3H), 7.53-7.52 (m, 1H), 7.42-7.23 (m, 12H), 7.10-7.04 (m, 6H), 6.90 (dd, 1H), 1.42 (s, 6H), 1.40 (s, 6H) | 700.86 | 700.85 | 74 |
| 48 | δ = 8.25-8.20 (m, 2H), 8.15-8.12 (m, 1H), 7.82 (d, 1H), 7.76 (d, 1H), 7.60-7.53 (m, 3H), 7.52-7.50 (m, 1H), 7.42-7.23 (m, 11H), 7.10-7.04 (m, 4H), 6.72-6.70 (m, 1H), 6.62-6.55 (m, 2H), 1.42 (s, 6H), 1.40 (s, 6H) | 750.99 | 750.91 | 73 |
| 51 | δ = 8.25-8.20 (m, 1H), 8.16-8.14 (m, 1H), 8.06-8.04 (m, 1H), 7.92-7.84 (m, 2H), 7.72-7.62 (m, 4H), 7.54-7.50 (m, 3H), 7.48-7.35 (m, 12H), 7.30-7.20 (m, 5H), 7.10-7.06 (m, 2H), 6.65-6.60 (m, 3H), 1.42 (s, 6H), 1.40 (s, 6H) | 835.07 | 835.06 | 71 |
| 52 | δ = 8.27-8.25 (m, 1H), 8.15-8.12 (m, 1H), 8.05-8.03 (m, 1H), 7.92-7.90 (m, 1H), 7.86-7.84 (m, 1H), 7.82-7.78 (m, 1H), 7.70-7.65 (m, 2H), 7.50-7.25 (m, 21H), 7.15-7.05 (m, 2H), 6.86-6.84 (m, 2H), 6.62 (d, 1H), 1.52 (s, 6H), 1.42 (s, 6H), 1.40 (s, 6H) | 875.13 | 875.12 | 76 |
| 54 | δ = 8.22-8.20 (m, 1H), 8.16-8.14 (m, 1H), 7.75-7.72 (m, 1H), 7.58-7.36 (m, 17H), 7.31-7.24 (m, 4H), 7.10-6.93 (m, 5H), 6.64-6.60 (m, 2H), 1.42 (s, 6H), 1.40 (s, 6H) | 762.99 | 762.97 | 72 |
| 56 | δ = 8.25-8.20 (m, 1H), 8.16-8.14 (m, 1H), 7.80-7.76 (m, 2H), 7.65-7.60 (m, 4H), 7.58-7.55 (m, 2H), 7.50-7.35 (m, 17H), 7.32-7.22 (m, 4H), 7.08-7.04 (m, 2H), 6.92-6.90 (m, 1H), 6.85-6.83 (m, 2H), 1.42 (s, 6H), 1.40 (s, 6H) | 821.11 | 821.08 | 76 |
| 60 | δ = 8.10-8.08 (m, 1H), 7.76-7.74 (m, 2H), 7.52-7.04 (m, 32H), 6.87-6.55 (m, 14H) | 904.18 | 904.16 | 74 |

TABLE 1-continued

| Compound | $^1$H NMR (CDCl$_3$, 400 MHz) | MS/FAB found | MS/FAB calc. | Yield (%) |
|---|---|---|---|---|
| 62 | δ = 8.85-8.80 (m, 1H), 8.52-8.50 (m, 1H), 8.04-7.96 (m, 4H), 7.52-7.02 (m, 28H), 6.87-6.75 (m, 14H) | 905.16 | 905.15 | 74 |
| 66 | δ = 8.20-8.18 (m, 1H), 8.10-8.06 (m, 1H), 7.85-7.80 (m, 4H), 7.78-7.72 (m, 2H), 7.52-7.46 (m, 5H), 7.40-6.75 (m, 24H), 6.60-6.52 (m, 5H), 1.51 (s, 6H) | 953.22 | 953.20 | 71 |
| 67 | δ = 8.21-8.18 (m, 1H), 7.80-6.98 (m, 31H), 6.68-6.51 (m, 5H) | 852.01 | 852.00 | 72 |
| 70 | δ = 8.25-8.22 (m, 1H), 8.15-8.12 (m, 1H), 8.07-8.04 (m, 1H), 7.90-7.85 (m, 2H), 7.74-7.72 (m, 1H), 7.58-7.21 (m, 23H), 6.85-6.82 (m, 2H), 6.68-6.62 (m, 3H), 1.51 (s, 6H), 1.45 (s, 6H) | 795.09 | 795.04 | 70 |
| 71 | δ = 8.26-8.24 (m, 1H), 8.15-8.12 (m, 1H), 8.07-8.04 (m, 1H), 7.90-7.85 (m, 2H), 7.74-7.72 (m, 1H), 7.58-7.19 (m, 22H), 7.03 (t, 1H), 6.96-6.88 (m, 2H), 6.60-6.54 (m, 2H), 6.48 (dd, 1H), 1.51 (s, 6H), 1.45 (s, 6H) | 795.05 | 795.04 | 76 |
| 76 | δ = 8.65 (m, 1H), 8.18-8.12 (m, 2H), 8.07-8.04 (m, 2H), 7.86 (d, 1H), 7.68-7.18 (m, 23H), 6.86-6.82 (m, 2H), 6.70-6.65 (m, 2H), 6.60 (dd, 1H), 1.51 (s, 6H), 1.45 (s, 6H) | 820.06 | 820.05 | 71 |
| 78 | δ = 8.65-8.62 (m, 1H), 8.17-8.12 (m, 1H), 8.07-8.04 (m, 3H), 7.86-7.80 (m, 2H), 7.74-7.72 (m, 1H), 7.62-7.15 (m, 20H), 6.92 (dd, 1H), 6.65-6.52 (m, 3H), 1.51 (s, 6H), 1.45 (s, 6H) | 825.09 | 825.08 | 72 |
| 80 | δ = δ = 8.52 (s, 1H), 8.10-8.06 (m, 3H), 7.78-6.98 (m, 28H), 6.75-7.60 (m, 10H), 6.27-6.24 (m, 3H) | 909.15 | 909.12 | 82 |

Organic Light-Emitting Device Manufacturing Examples

Example 1

As an anode, an indium tin oxide (ITO) glass substrate (available from Corning) having a thickness of 15 Ω/cm² (1200 Å) was cut to a size of 50 mm×50 mm×0.7 mm, sonicated in isopropyl alcohol and pure water for 5 minutes each, and then cleaned with UV and ozone for 30 minutes. The ITO glass substrate was then mounted on a vacuum depositor.

2-TNATA was vacuum deposited on the substrate at a thickness of 600 Å to form a hole injection layer, and then Compound 5, as a hole transporting compound, was vacuum deposited thereon at a thickness of 300 Å to form a hole transport layer.

9,10-di-naphthalene-2-yl-anthracene (also referred to as ADN), which is a commonly used blue fluorescent host, and N,N,N',N'-tetraphenyl-pyrene-1,6-diamine (TPD), which is a commonly used blue fluorescent dopant, were co-deposited at a weight ratio of 98:2 on the hole transport layer to form an emission layer having a thickness of 300 Å.

Alq$_3$ was deposited on the emission layer to form an electron transport layer having a thickness of 300 Å, LiF (which is a halogenated alkali metal) was deposited on the electron transport layer to form an electron injection layer having a thickness of 10 Å, and Al was deposited on the electrode injection layer to form a LiF/Al electrode (a cathode) having a thickness of 3,000 Å, thereby completing the manufacture of an organic light-emitting device.

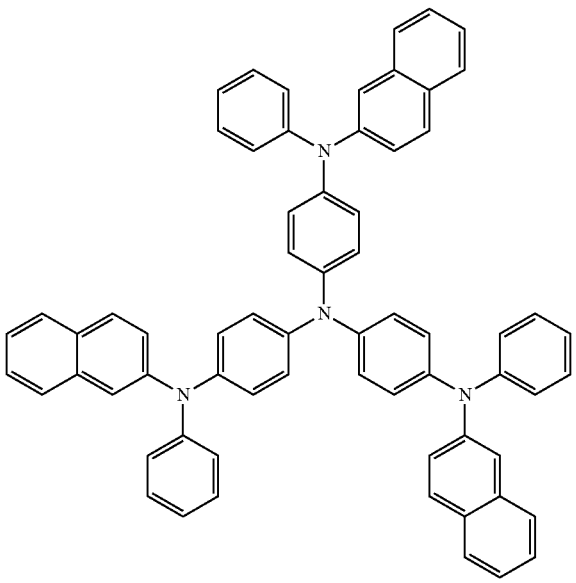

2-TNATA

-continued

ADN

TPD

Example 2

An organic light-emitting device was manufactured in a similar manner as in Example 1, except that Compound 10 was used instead of Compound 5 in the formation of the hole transport layer.

Example 3

An organic light-emitting device was manufactured in a similar manner as in Example 1, except that Compound 14 was used instead of Compound 5 in the formation of the hole transport layer.

Example 4

An organic light-emitting device was manufactured in a similar manner as in Example 1, except that Compound 19 was used instead of Compound 5 in the formation of the hole transport layer.

Example 5

An organic light-emitting device was manufactured in a similar manner as in Example 1, except that Compound 24 was used instead of Compound 5 in the formation of the hole transport layer.

Example 6

An organic light-emitting device was manufactured in a similar manner as in Example 1, except that Compound 28was used instead of Compound 5 in the formation of the hole transport layer.

Example 7

An organic light-emitting device was manufactured in a similar manner as in Example 1, except that Compound 31 was used instead of Compound 5 in the formation of the hole transport layer.

Example 8

An organic light-emitting device was manufactured in a similar manner as in Example 1, except that Compound 39 was used instead of Compound 5 in the formation of the hole transport layer.

Example 9

An organic light-emitting device was manufactured in a similar manner as in Example 1, except that Compound 43 was used instead of Compound 5 in the formation of the hole transport layer.

Example 10

An organic light-emitting device was manufactured in a similar manner as in Example 1, except that Compound 48 was used instead of Compound 5 in the formation of the hole transport layer.

Example 11

An organic light-emitting device was manufactured in a similar manner as in Example 1, except that Compound 51 was used instead of Compound 5 in the formation of the hole transport layer.

Example 12

An organic light-emitting device was manufactured in a similar manner as in Example 1, except that Compound 54 was used instead of Compound 5 in the formation of the hole transport layer.

Example 13

An organic light-emitting device was manufactured in a similar manner as in Example 1, except that Compound 62 was used instead of Compound 5 in the formation of the hole transport layer.

Example 14

An organic light-emitting device was manufactured in a similar manner as in Example 1, except that Compound 66 was used instead of Compound 5 in the formation of the hole transport layer.

Example 15

An organic light-emitting device was manufactured in a similar manner as in Example 1, except that Compound 71 was used instead of Compound 5 in the formation of the hole transport layer.

Example 16

An organic light-emitting device was manufactured in a similar manner as in Example 1, except that Compound 76 was used instead of Compound 5 in the formation of the hole transport layer.

Comparative Example 1

An organic light-emitting device was manufactured in a similar manner as in Example 1, except that NPB, which is a commonly used material, was used instead of Compound 5 in the formation of the hole transport layer.

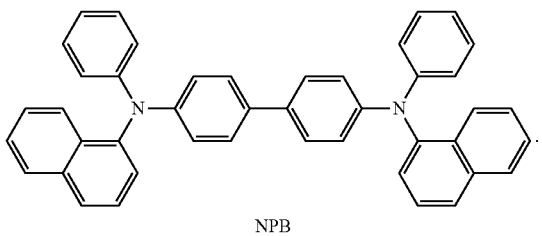 [SMILES: c1ccc(N(c2ccc(-c3ccc(N(c4ccccc4)c4cccc5ccccc45)cc3)cc2)c2cccc3ccccc23)cc1 ; "NPB"]

NPB

Comparative Example 2

An organic light-emitting device was manufactured in a similar manner as in Example 1, except that Compound 335, which is a commonly used material, was used instead of Compound 5 in the formation of the hole transport layer.

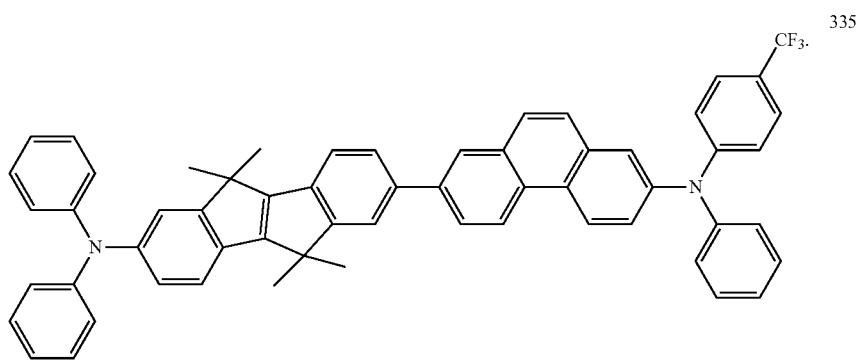 [SMILES: CC1(C)C2=C(c3ccc(-c4ccc5c(ccc6cc(N(c7ccccc7)c7ccc(C(F)(F)F)cc7)ccc65)c4)cc31)C(C)(C)c1cc(N(c3ccccc3)c3ccccc3)ccc12]

335

As a result of using a compound represented by Formula 1 according to an embodiment of the present disclosure as a hole transport material, all such Examples exhibited better current, voltage, and luminance (I-V-L) characteristics and improved or increased lifespans compared to those Comparative Examples containing the commonly used materials NPB and Compound 335. In this regard, it may be concluded that the compound represented by Formula 1 according to an embodiment of the present disclosure may be used as a material in the hole transport region to produce beneficial effects. The results with respect to each of the Examples and the representative lifespans of the compounds are shown in Table 2.

TABLE 2

|  | Hole transport layer | Driving voltage (V) | Current density (mA/cm$^2$) | Luminance (cd/m$^2$) | Efficiency (cd/A) | Color of emitted light | Half life (hr @ 100 mA/cm$^2$) |
|---|---|---|---|---|---|---|---|
| Example 1 | Compound 5 | 5.45 | 50 | 3110 | 6.22 | blue | 350 hr |
| Example 2 | Compound 10 | 5.42 | 50 | 3108 | 6.21 | blue | 350 hr |
| Example 3 | Compound 14 | 5.62 | 50 | 3220 | 6.44 | blue | 340 hr |
| Example 4 | Compound 19 | 5.65 | 50 | 3185 | 6.33 | blue | 342 hour |
| Example 5 | Compound 24 | 5.55 | 50 | 3065 | 6.13 | blue | 335 hr |
| Example 6 | Compound 28 | 5.71 | 50 | 3075 | 6.15 | blue | 360 hr |
| Example 7 | Compound 31 | 5.49 | 50 | 3220 | 6.44 | blue | 365 hour |
| Example 8 | Compound 39 | 5.46 | 50 | 3250 | 6.50 | blue | 380 hr |
| Example 9 | Compound 43 | 5.49 | 50 | 3330 | 6.66 | blue | 330 hr |
| Example 10 | Compound 48 | 5.51 | 50 | 3200 | 6.40 | blue | 340 hr |
| Example 11 | Compound 51 | 5.54 | 50 | 3220 | 6.44 | blue | 324 hr |
| Example 12 | Compound 54 | 5.48 | 50 | 3215 | 6.43 | blue | 320 hr |
| Example 13 | Compound 62 | 5.68 | 50 | 3075 | 6.15 | blue | 315 hr |

TABLE 2-continued

| | Hole transport layer | Driving voltage (V) | Current density (mA/cm$^2$) | Luminance (cd/m$^2$) | Efficiency (cd/A) | Color of emitted light | Half life (hr @ 100 mA/cm$^2$) |
|---|---|---|---|---|---|---|---|
| Example 14 | Compound 66 | 5.59 | 50 | 3190 | 6.38 | blue | 310 hr |
| Example 15 | Compound 71 | 5.56 | 50 | 3070 | 6.14 | blue | 344 hr |
| Example 16 | Compound 76 | 5.47 | 50 | 3012 | 6.02 | blue | 305 hr |
| Comparative Example 1 | NPB | 7.01 | 50 | 2645 | 5.29 | blue | 258 hr |
| Comparative Example 2 | Compound 335 | 6.80 | 50 | 2765 | 5.60 | blue | 270 hr |

As described above, according to one or more of the above embodiments, an organic light-emitting device including a compound represented by Formula 1 may have excellent hole transporting ability and material stability, and thus may be used as a material for a hole transport region. An organic light-emitting device using the compound represented by Formula 1 may exhibit high efficiency, low voltage, high luminance, and a long lifespan.

It should be understood that the example embodiments described herein should be considered in a descriptive sense only and not for purposes of limitation. Descriptions of features or aspects within each example embodiment should typically be considered as being available for other similar features or aspects in other example embodiments.

While one or more example embodiments have been described with reference to the drawing, it will be understood by those of ordinary skill in the art that various changes in form and details may be made therein without departing from the spirit and scope of the present disclosure as defined by the following claims and equivalents thereof.

What is claimed is:

1. A compound represented by Formula 1:

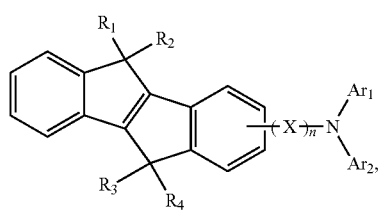

Formula 1 wherein, in Formula 1, $R_1$ to $R_4$ are each independently selected from hydrogen, deuterium, a halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $Ar_1$ and $Ar_2$ are each independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

X is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, n is an integer selected from 0 to 5, and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, substituted $C_6$-$C_{60}$ arylene group, substituted $C_1$-$C_{60}$ heteroarylene group, substituted divalent non-aromatic condensed polycyclic group, and substituted divalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), and —B(Q$_{16}$)(Q$_{17}$);

a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group; and a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), and —B(Q$_{26}$)(Q$_{27}$), wherein Q$_{11}$ to Q$_{17}$ and Q$_{21}$ to Q$_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

2. The compound of claim 1, wherein, in Formula 1, R$_1$ to R$_4$ are each independently selected from a substituted or unsubstituted C$_1$-C$_{60}$ alkyl group, a substituted or unsubstituted C$_6$-C$_{60}$ aryl group, and a substituted or unsubstituted C$_1$-C$_{60}$ heteroaryl group.

3. The compound of claim 1, wherein, in Formula 1, adjacent substituents of R$_1$ to R$_4$ are linked to form a ring.

4. The compound of claim 1, wherein, in Formula 1, Ar$_1$ and Ar$_2$ are each independently selected from a substituted or unsubstituted C$_6$-C$_{60}$ aryl group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

5. The compound of claim 1, wherein, in Formula 1, X is at least one group selected from Formulae 2a and 2b:

2a

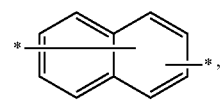

2b wherein, in Formulae 2a and 2b, * denotes a binding site.

6. The compound of claim 1, wherein, in Formula 1, Ar$_1$ and Ar$_2$ are each independently selected from Formulae 3a to 3g:

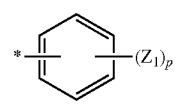

3a

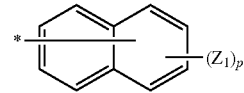

3b

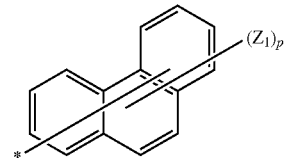

3c

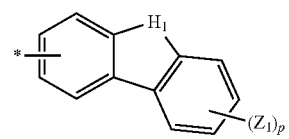

3d

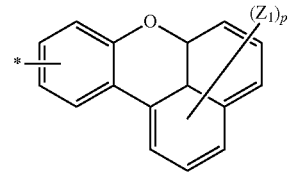

3e

-continued

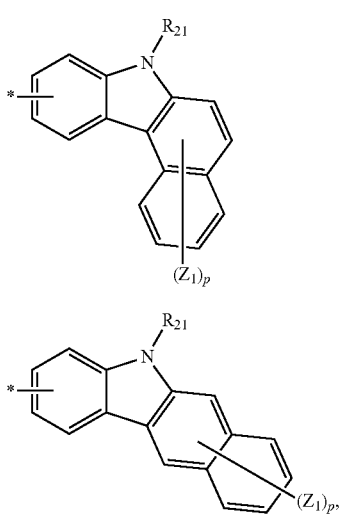

3f

3g wherein, in Formulae 3a to 3g,

H$_1$ denotes O, S, NR$_{31}$, or CR$_{32}$R$_{33}$,

R$_{31}$ to R$_{33}$, R$_{21}$, and Z$_1$ are each independently selected from hydrogen, deuterium, a halogen, SiR$_{41}$R$_{42}$R$_{43}$, a substituted or unsubstituted C$_1$-C$_{20}$ alkyl group, a substituted or unsubstituted C$_6$-C$_{20}$ aryl group, a substituted or unsubstituted C$_1$-C$_{20}$ heteroaryl group, a substituted or unsubstituted monovalent non-aromatic condensed polycyclic group, and a substituted or unsubstituted monovalent non-aromatic condensed heteropolycyclic group, R$_{41}$ to R$_{43}$ are each independently selected from a substituted or unsubstituted C$_1$-C$_{20}$ alkyl group and a substituted or unsubstituted C$_6$-C$_{20}$ aryl group, p denotes an integer selected from 1 to 9, and

* denotes a binding site.

7. The compound of claim 6, wherein R$_{32}$ and R$_{33}$ are linked to form a ring.

8. The compound of claim 1, wherein, in Formula 1, R$_1$ to R$_4$ are each independently selected from Formulae 4a to 4c:

*—CH$_3$    4a

*—$\overset{H_2}{C}$—CH$_3$    4b

4c

[benzene ring with (Z$_1$)$_p$]

wherein, in Formulae 4a to 4c,

Z$_1$ is selected from hydrogen, deuterium, a halogen, a substituted or unsubstituted C$_1$-C$_{20}$ alkyl group, a substituted or unsubstituted C$_6$-C$_{20}$ aryl group, a substituted or unsubstituted C$_1$-C$_{20}$ heteroaryl group, a substituted or unsubstituted monovalent non-aromatic condensed polycyclic group, and a substituted or unsubstituted monovalent non-aromatic condensed heteropolycyclic group, p is an integer selected from 1 to 5, and

* denotes a binding site.

9. The compound of claim 1, wherein the compound represented by Formula 1 is a compound represented by Formula 2:

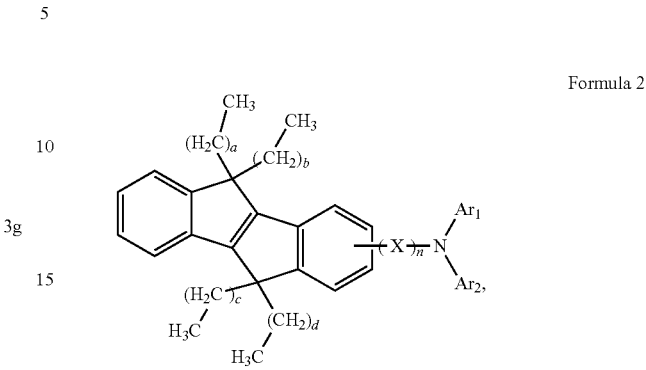

Formula 2 wherein, in Formula 2, a, b, c, and d are each independently an integer selected from 0 and 1.

10. The compound of claim 1, wherein the compound represented by Formula 1 is a compound represented by Formula 3:

Formula 3

11. The compound of claim 1, wherein the compound represented by Formula 1 is a compound represented by Formula 4:

Formula 4

12. The compound of claim 1, wherein the compound represented by Formula 1 is selected from the compounds below:

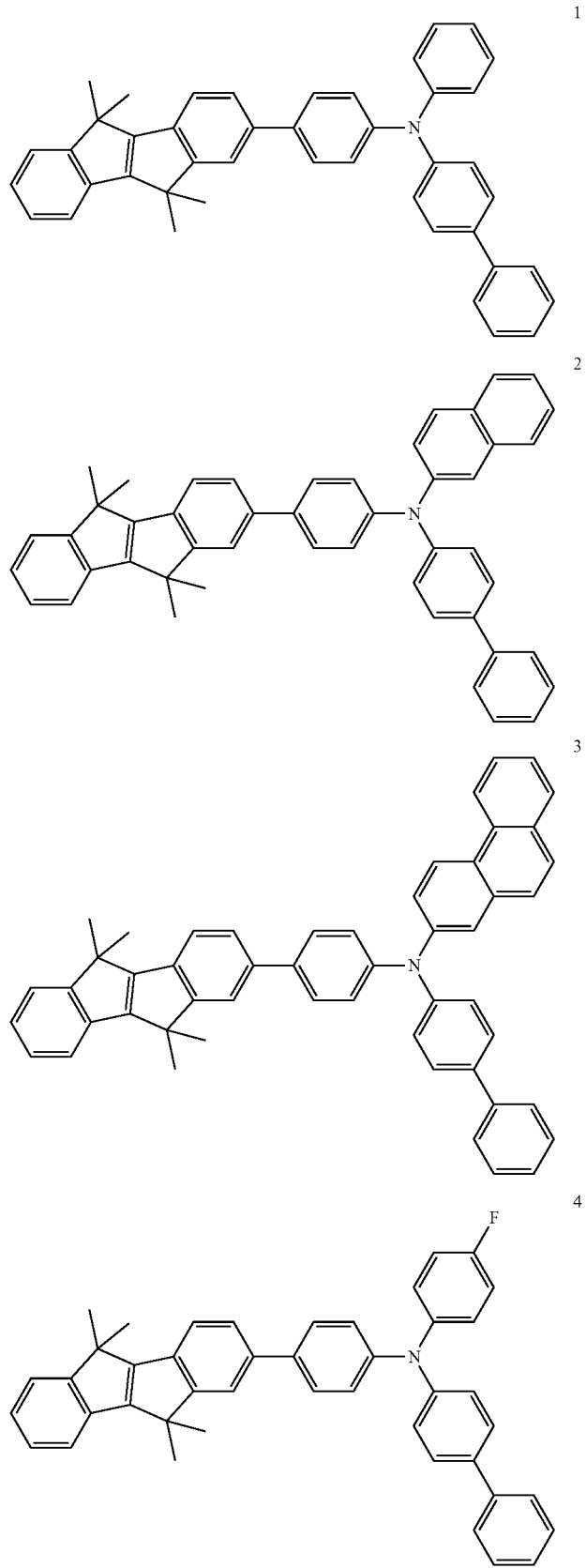

-continued
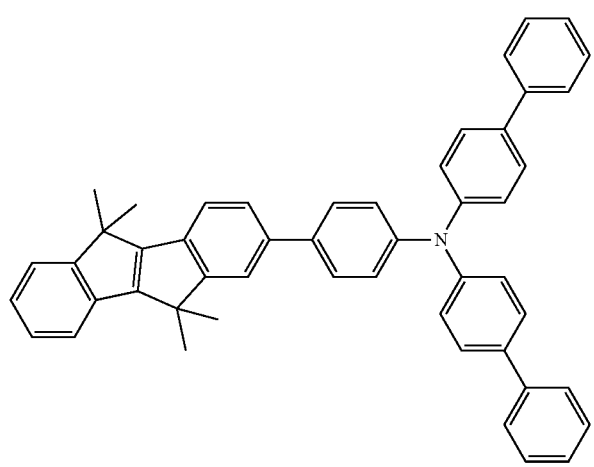
5
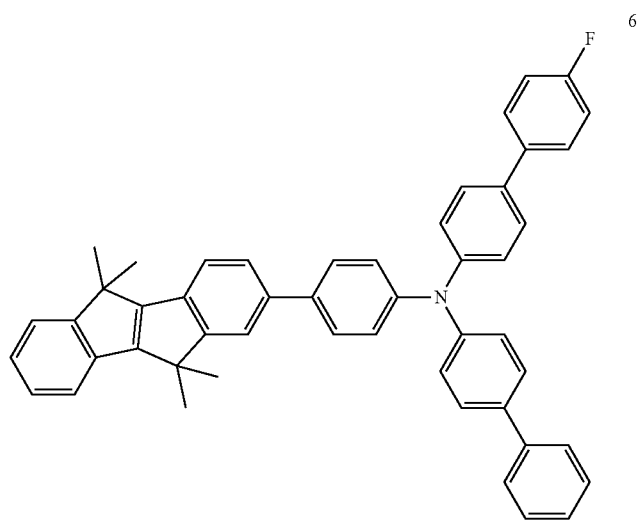
6
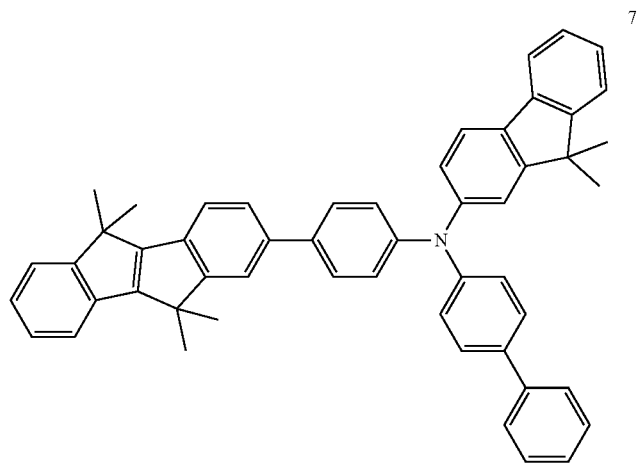
7

-continued
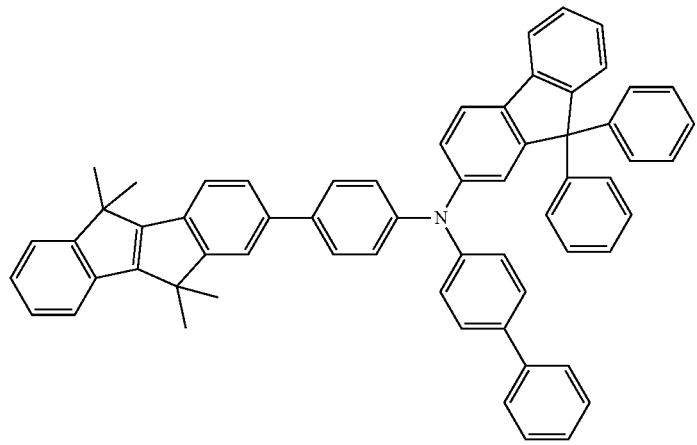
8
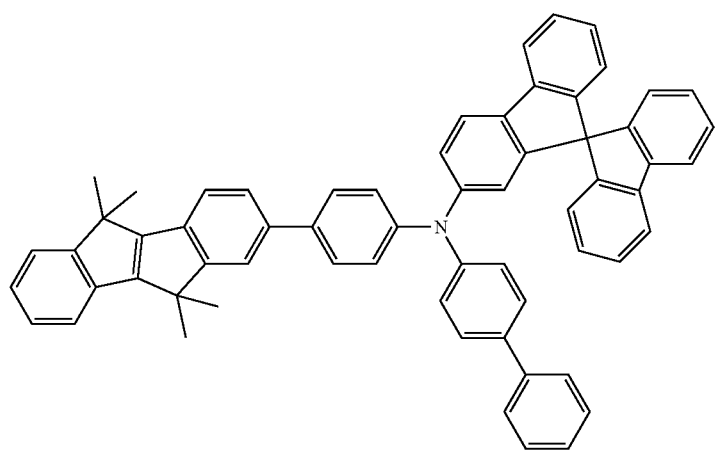
9
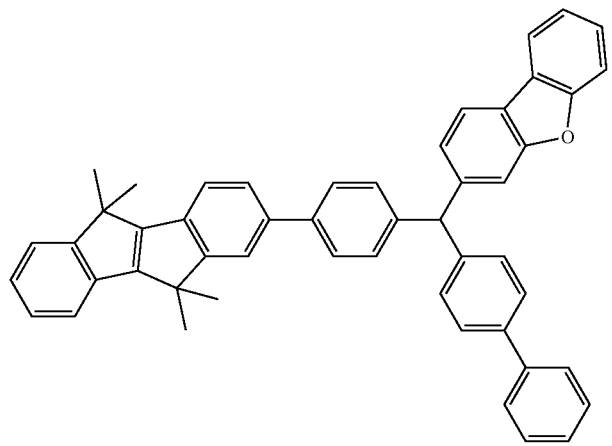
10

-continued
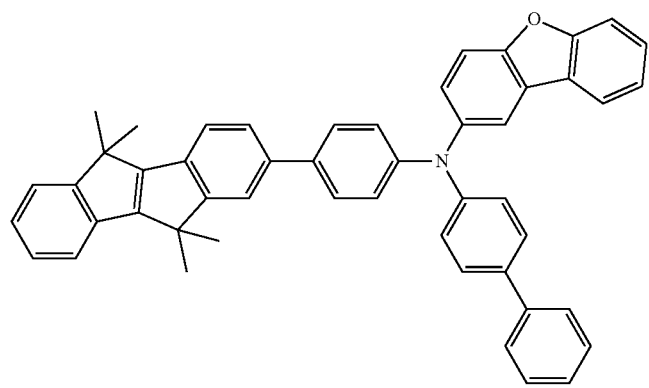
11
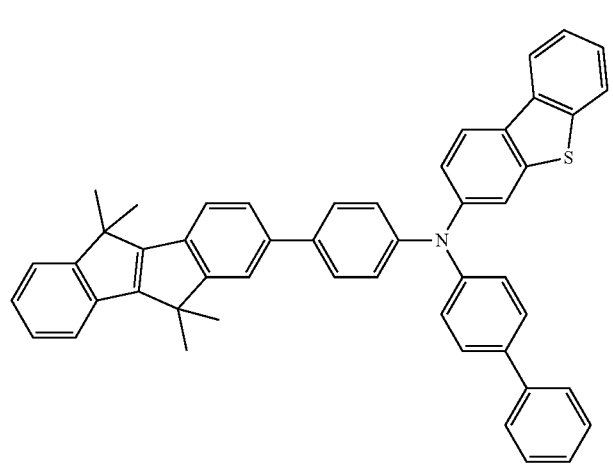
12
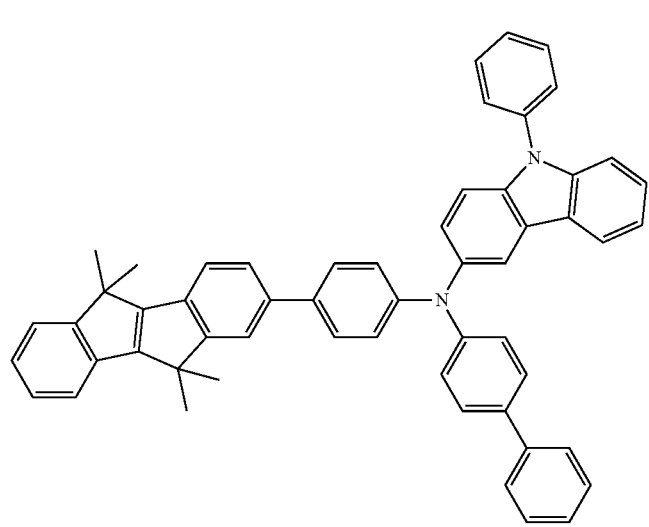
13

-continued
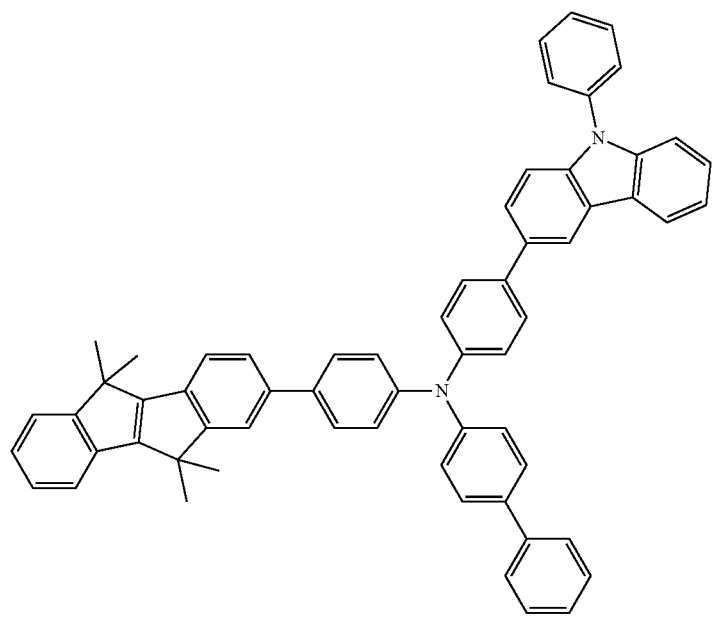
14
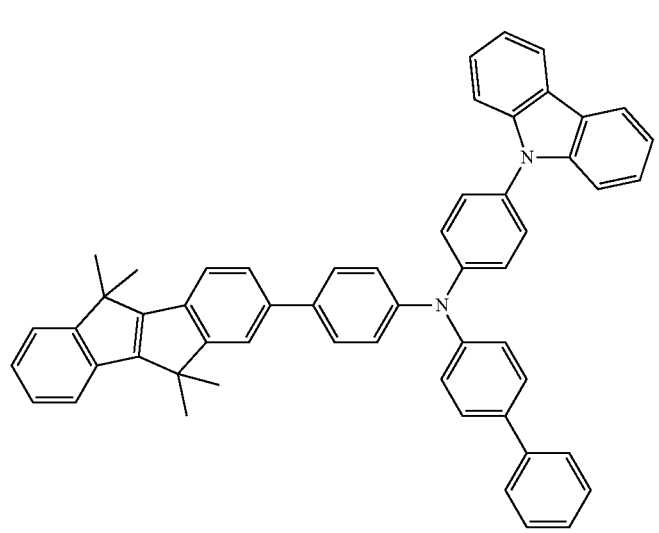
15
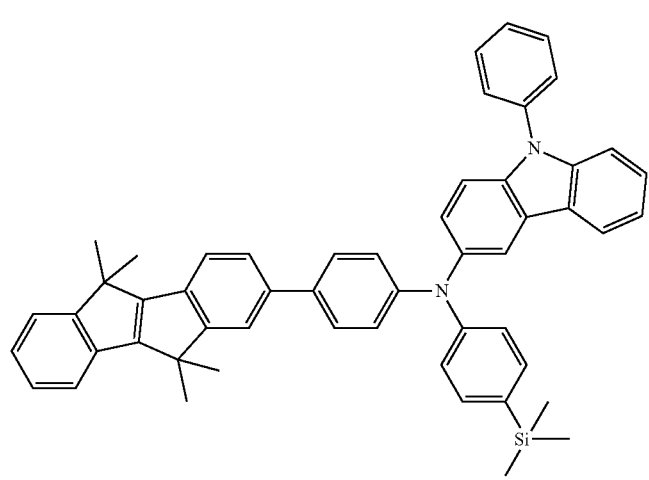
16

-continued
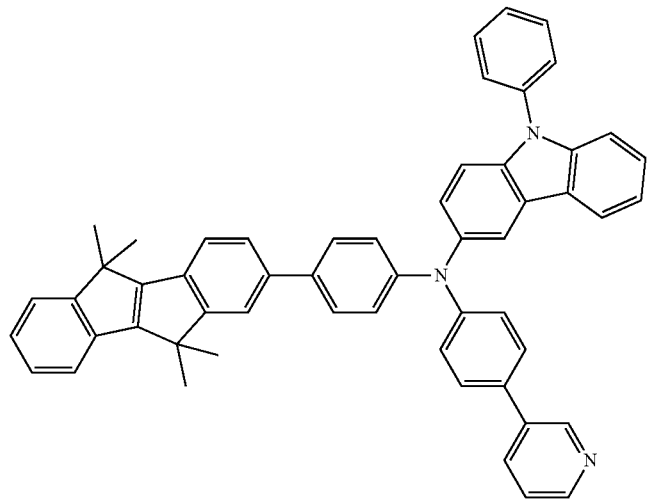
17
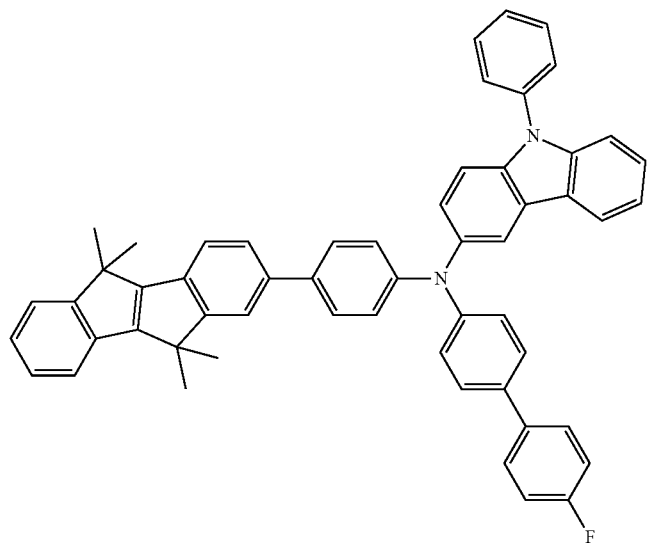
18
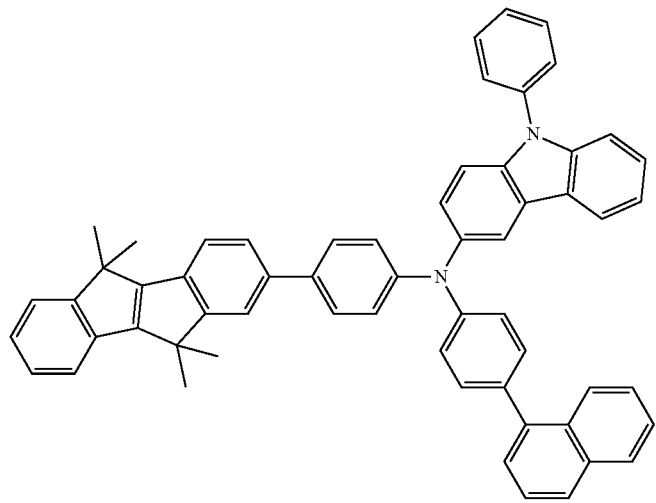
19

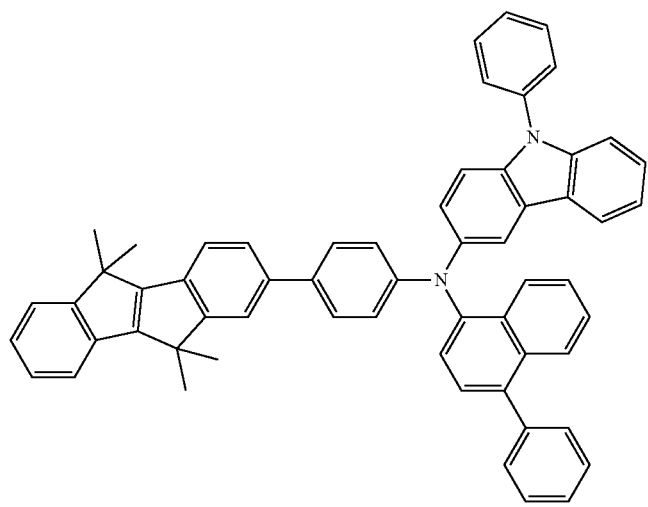
20
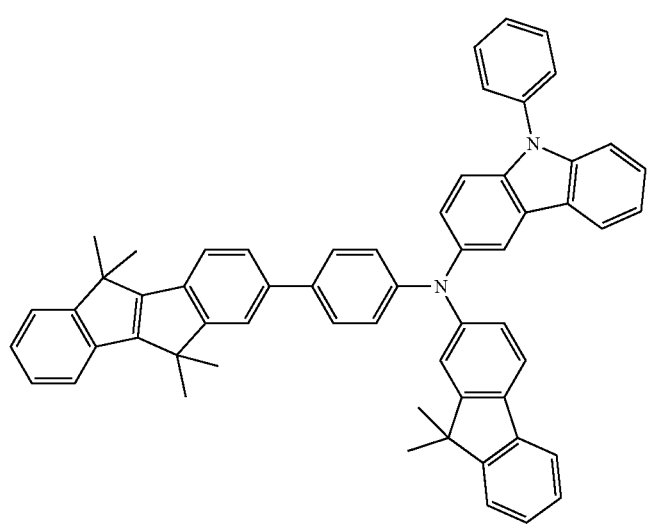
21
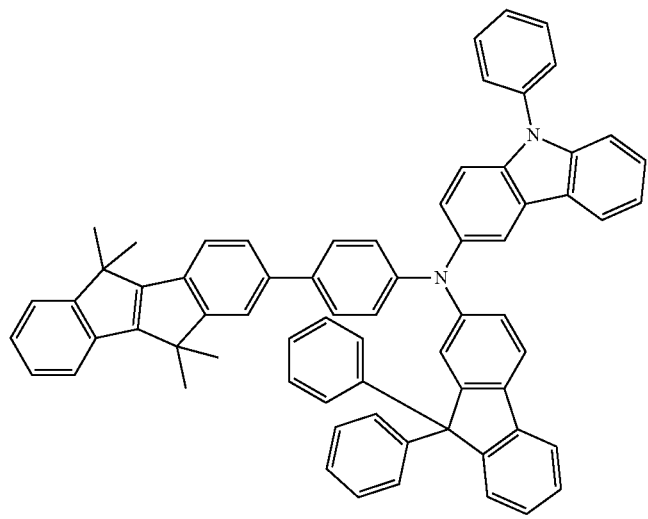
22

-continued
23
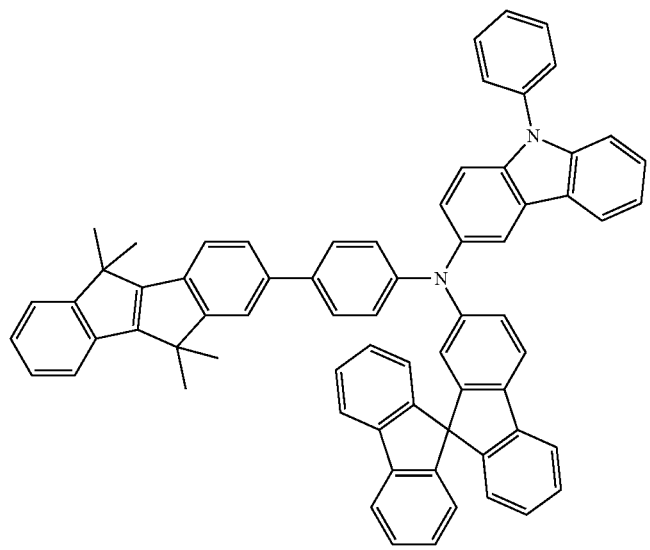
24
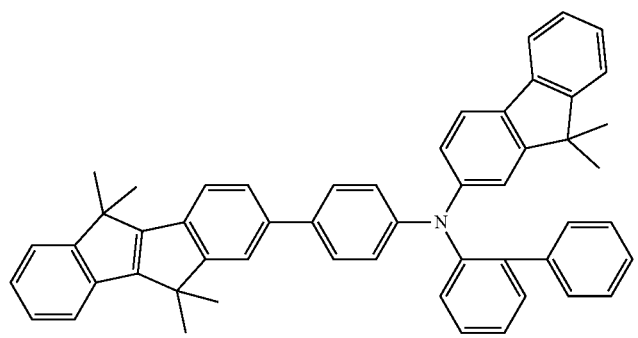
25
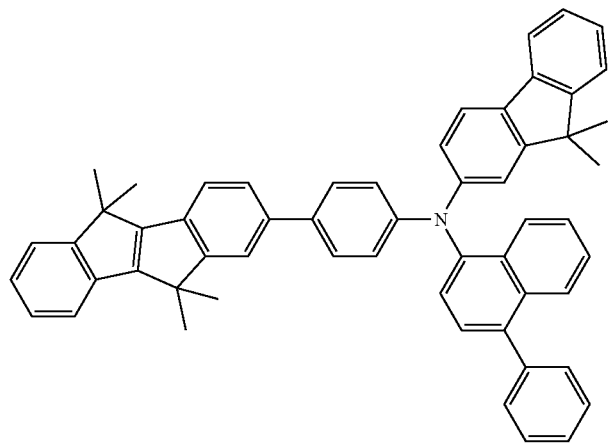

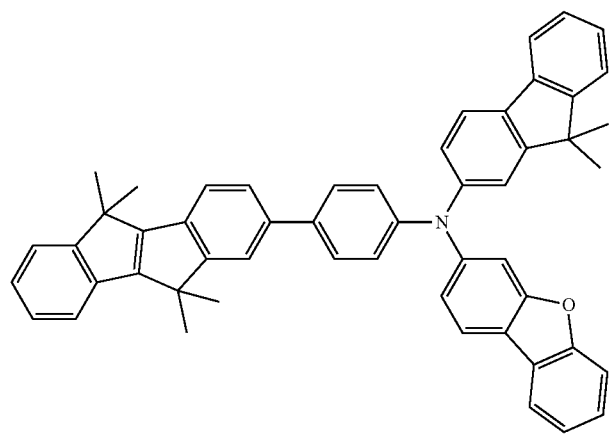
26
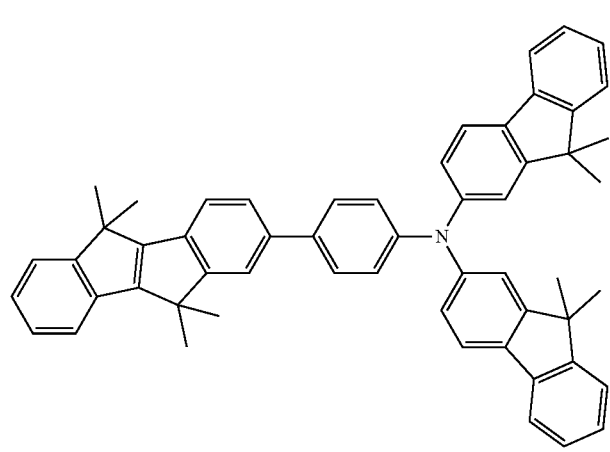
27
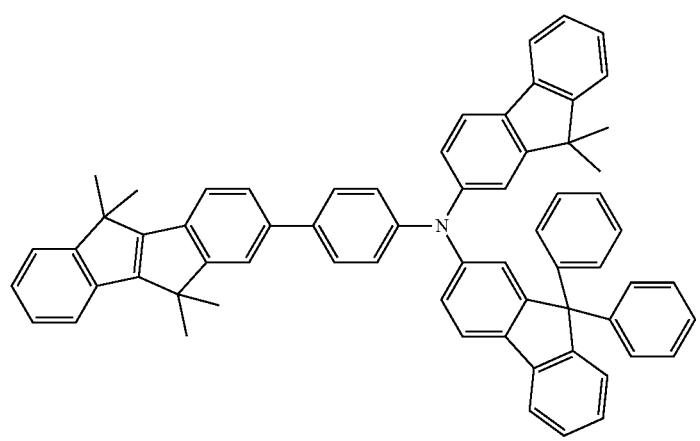
28

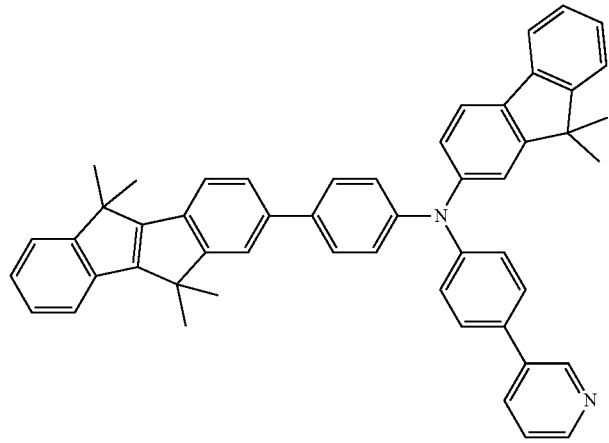
29
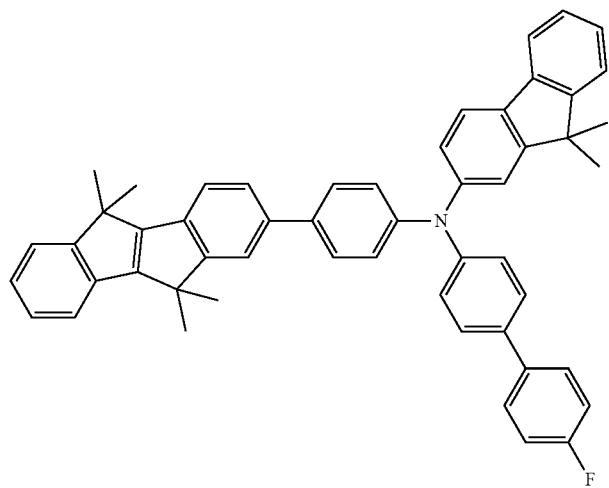
30
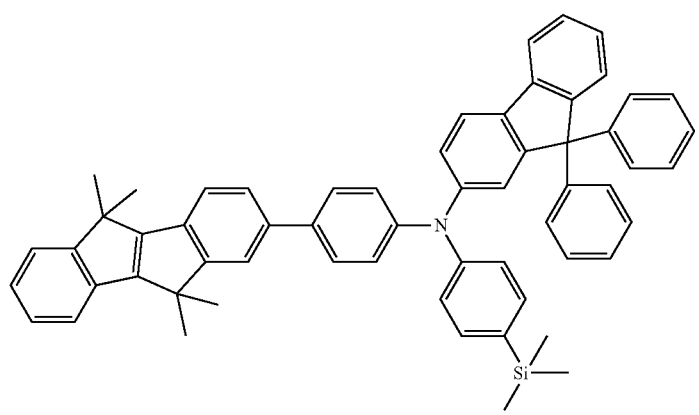
31

-continued
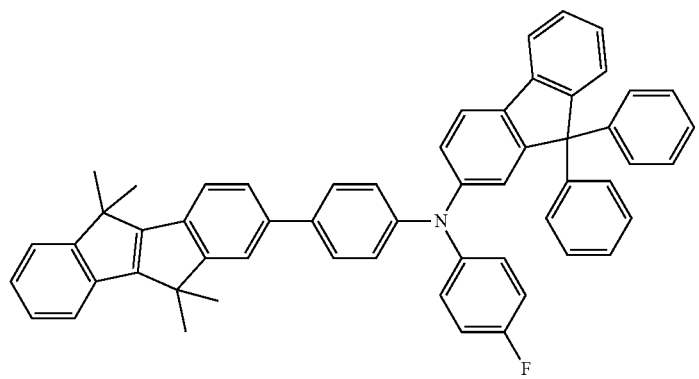
32
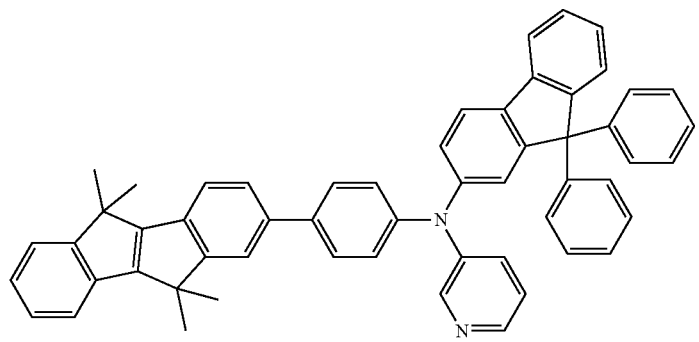
33
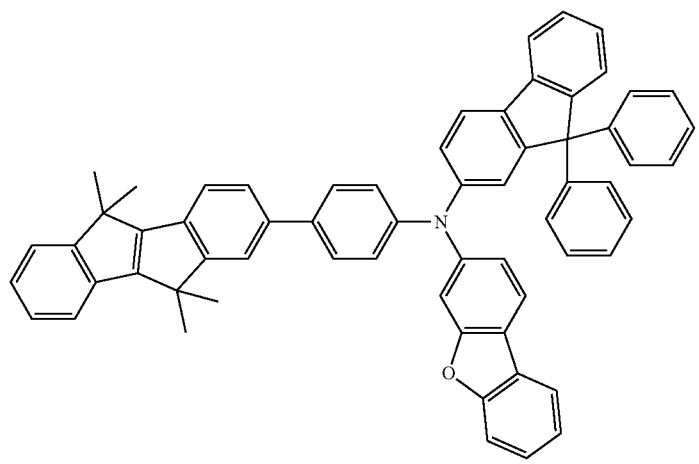
34
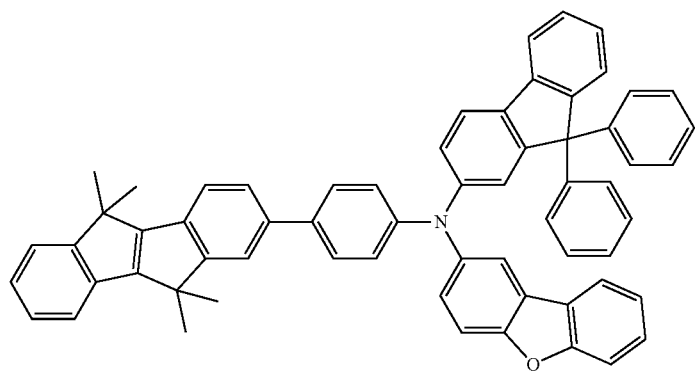
35

-continued
36
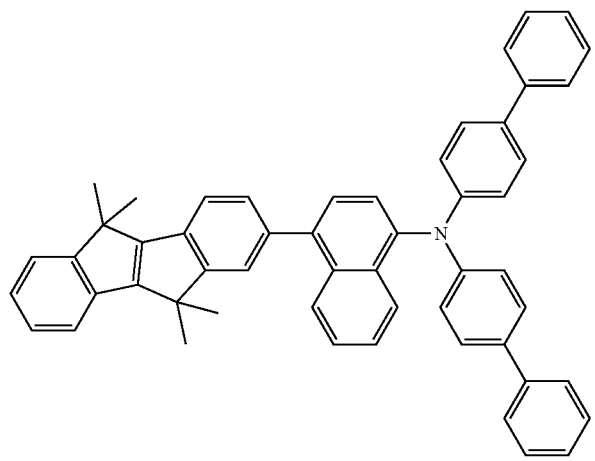
37
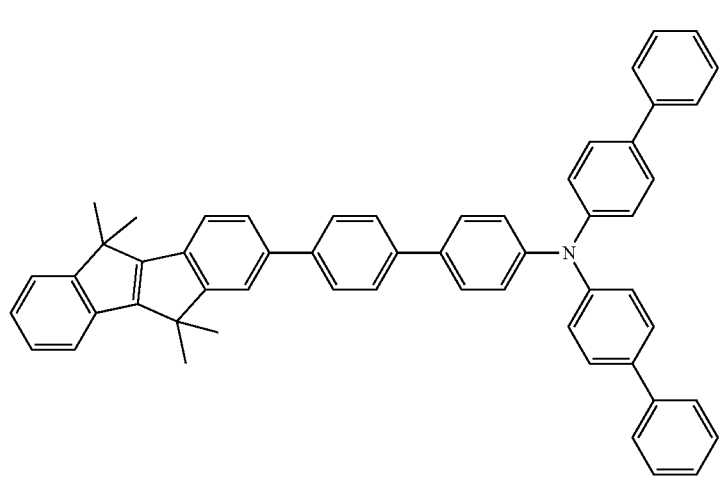
38
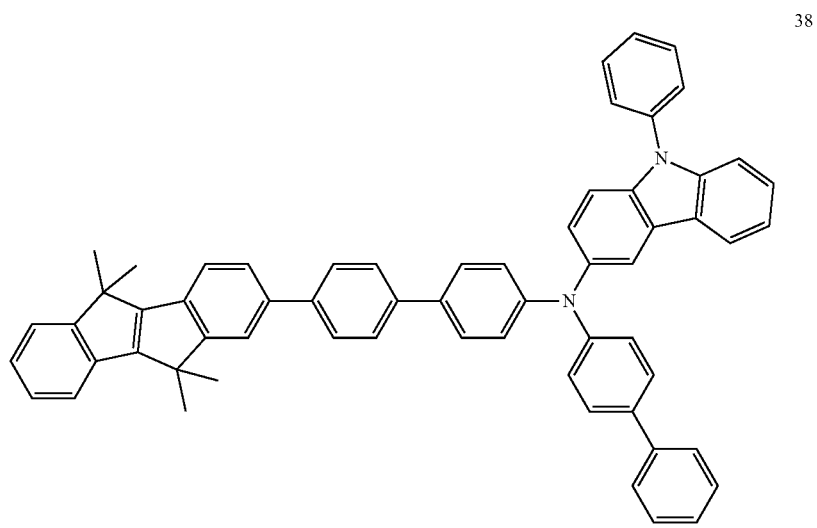

-continued
39
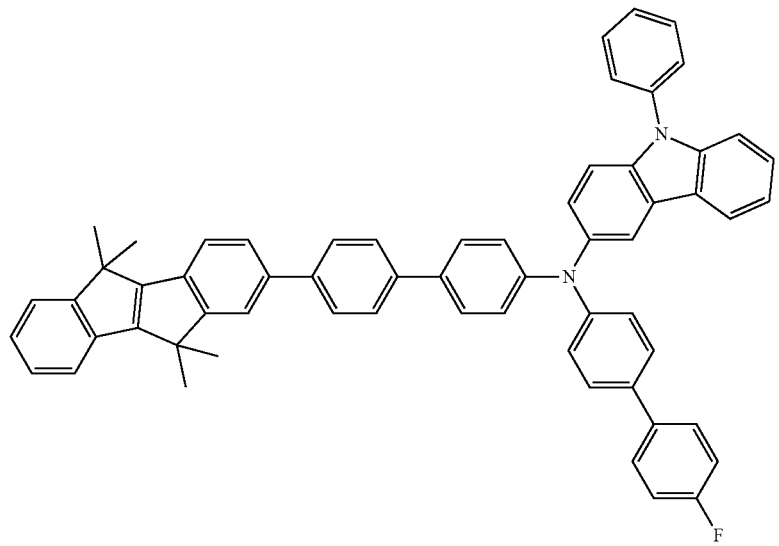
40
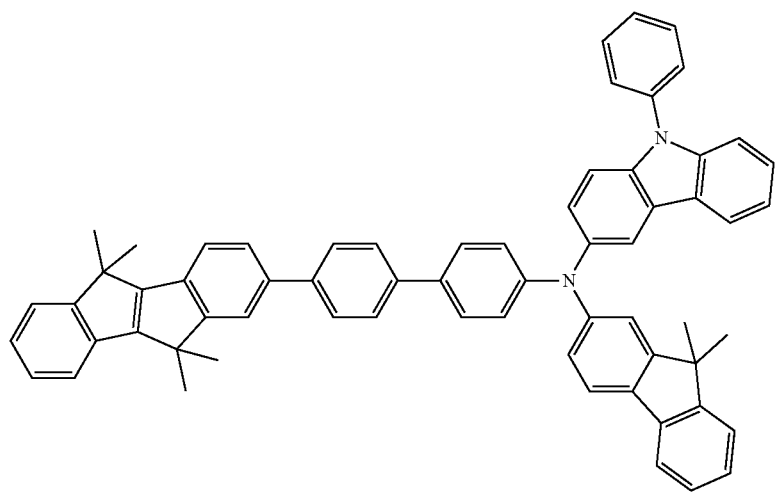
41
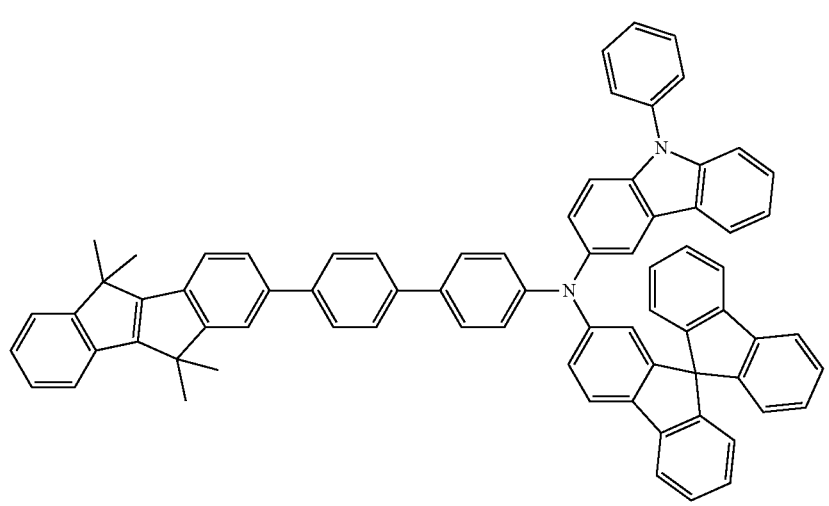

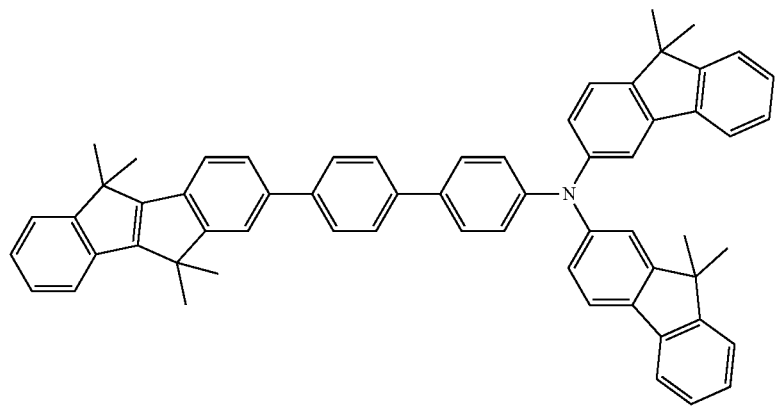
42
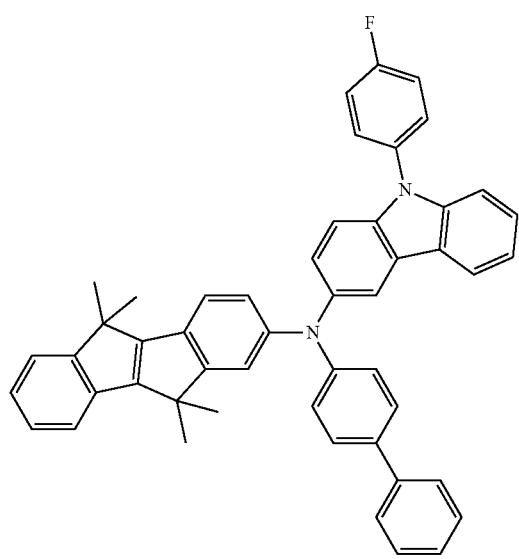
43
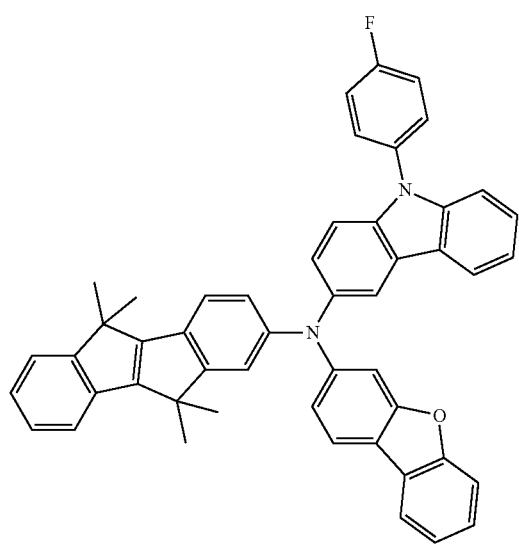
44

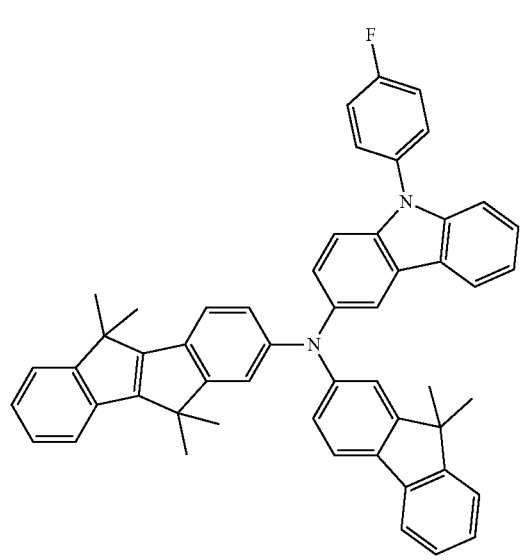
45
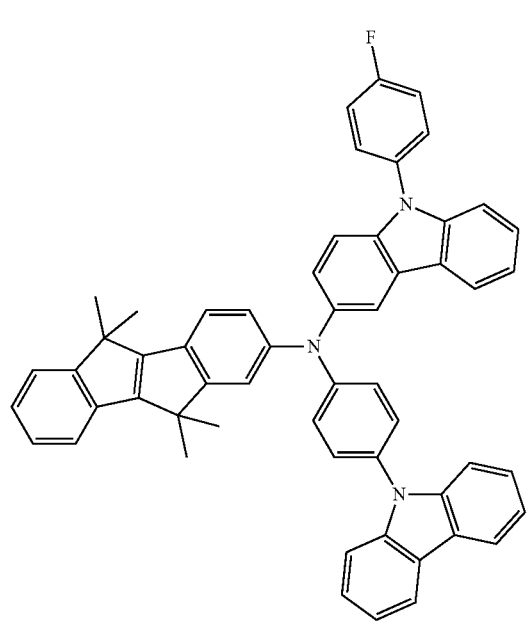
46

-continued
47
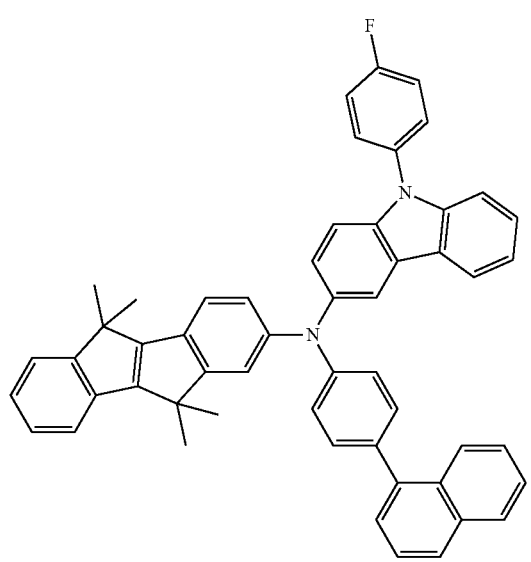
48
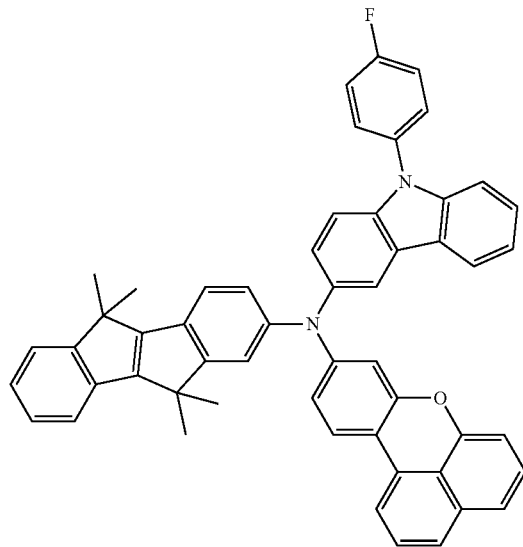
49
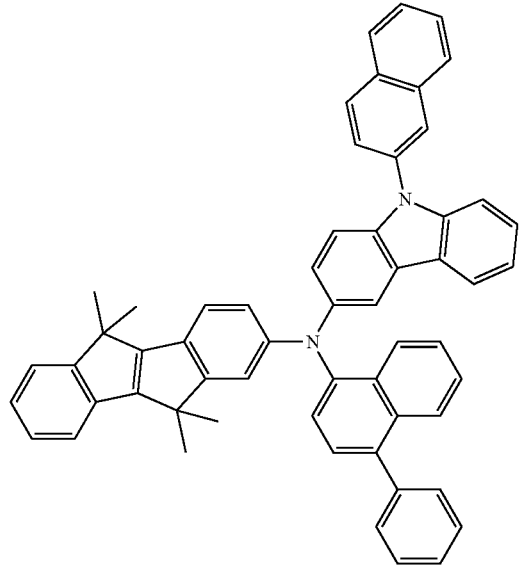

50
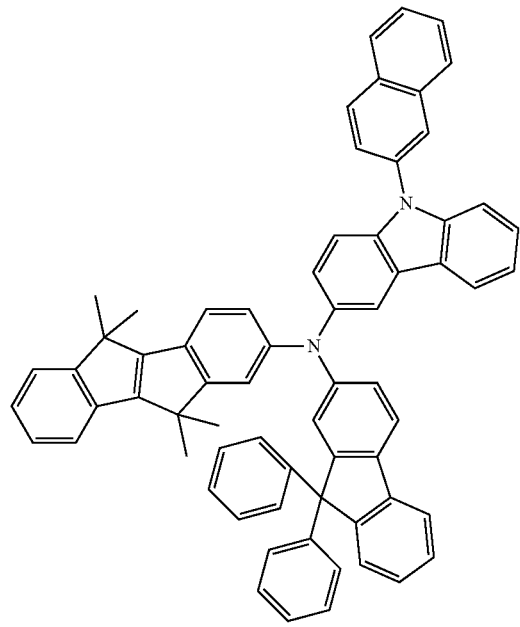
51
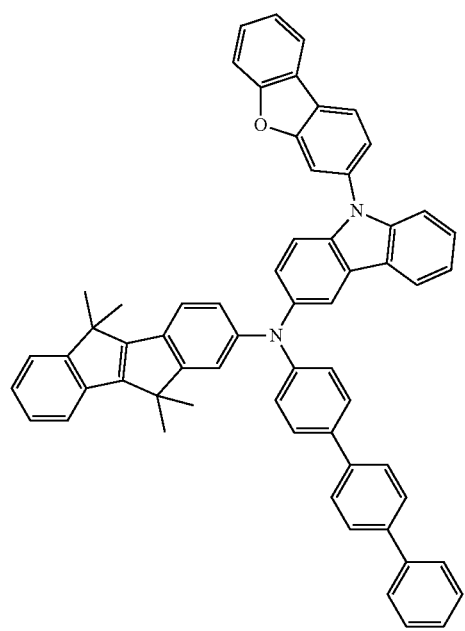

-continued
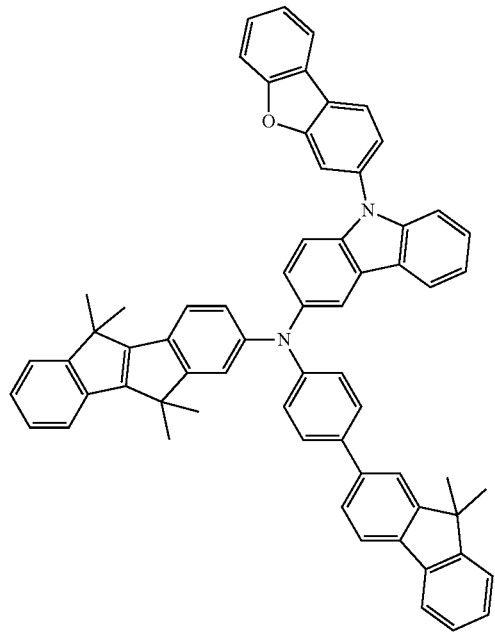
52
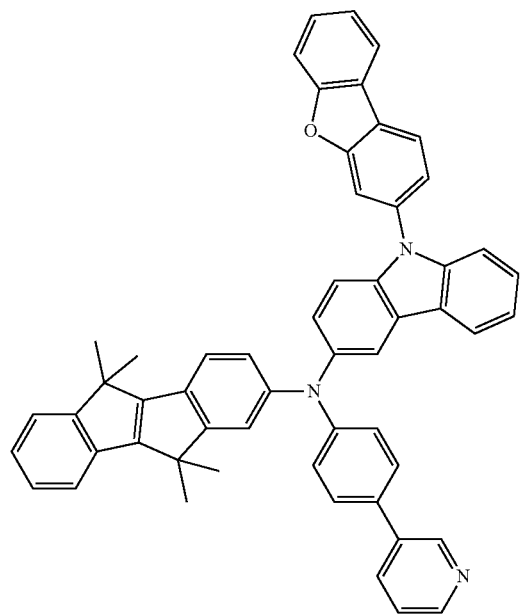
53

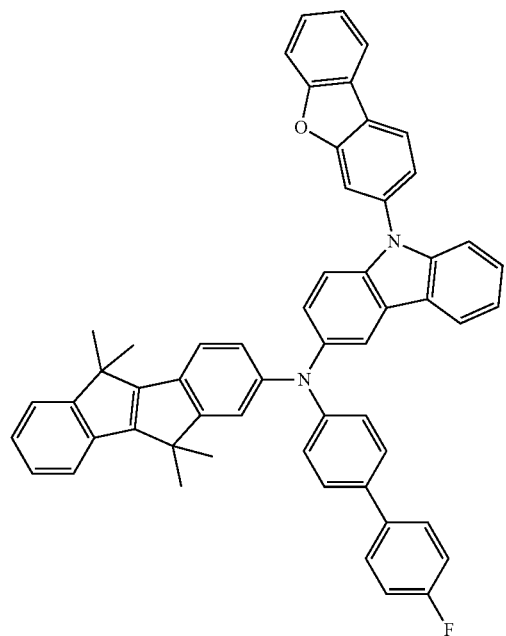
54
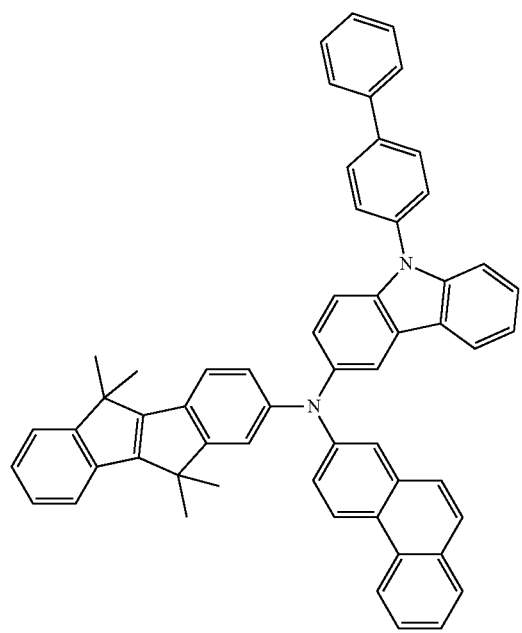
55

56
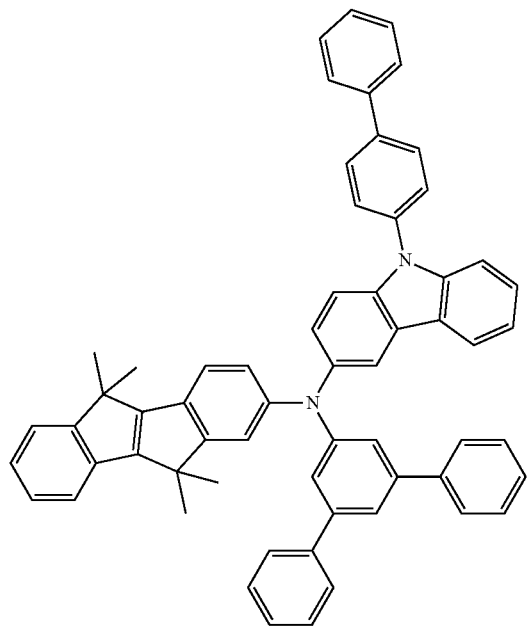
57
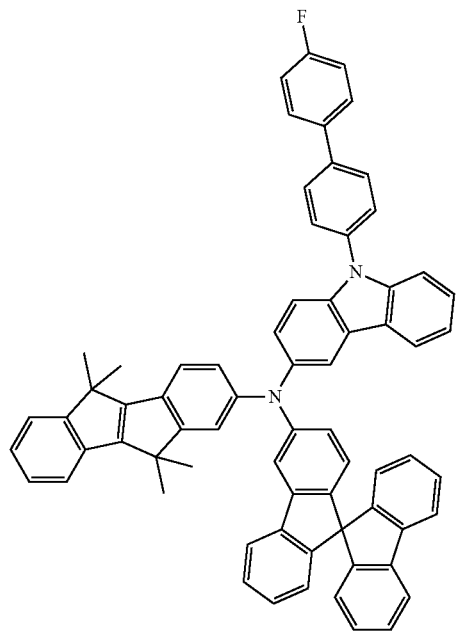
58
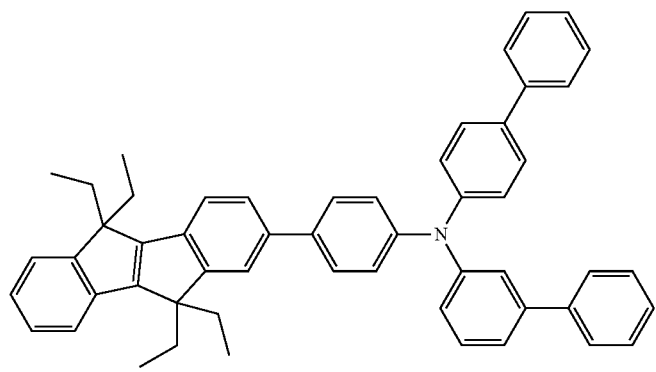

-continued
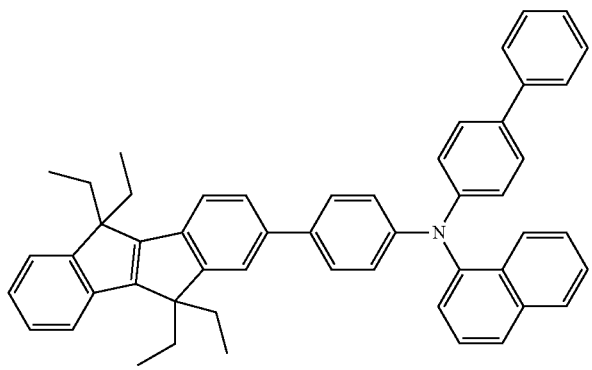
59
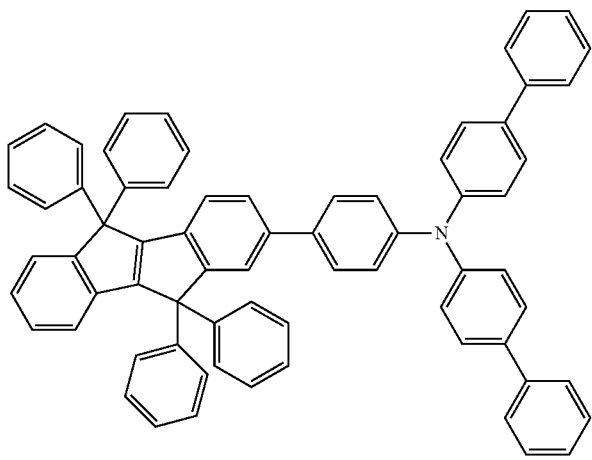
60
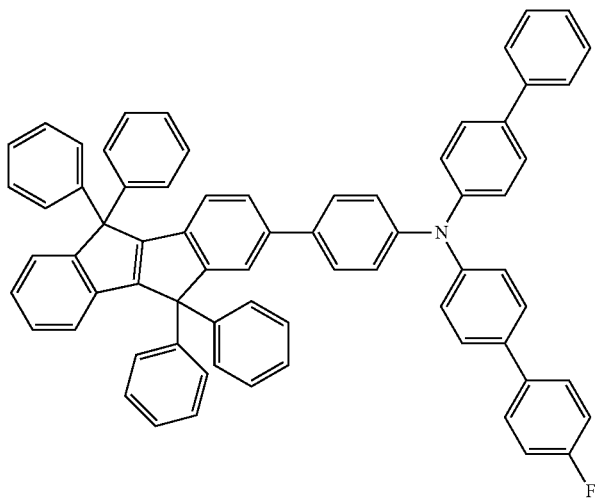
61

-continued
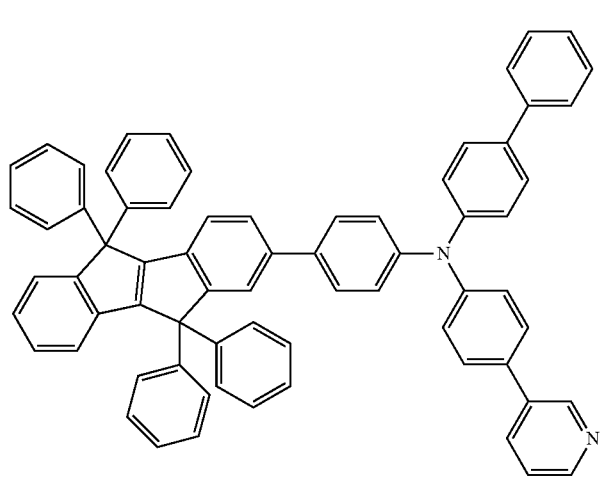
62
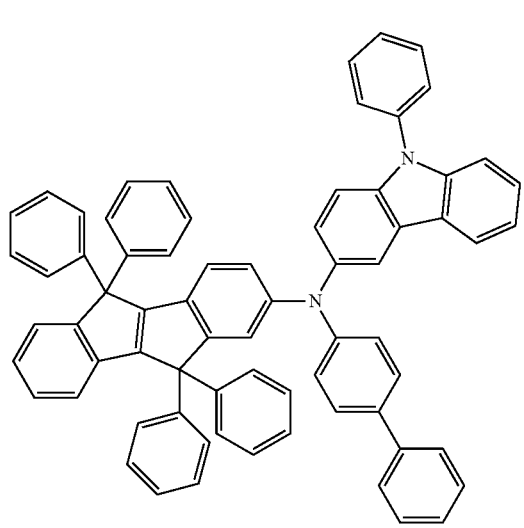
63
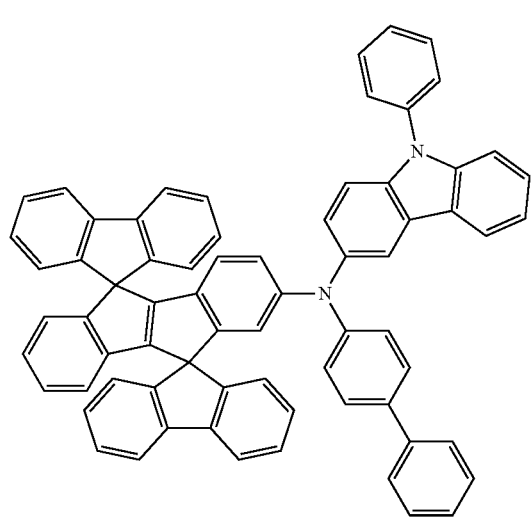
64

-continued
65
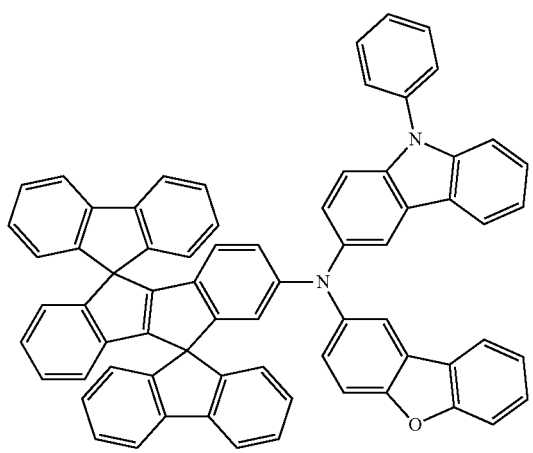
66
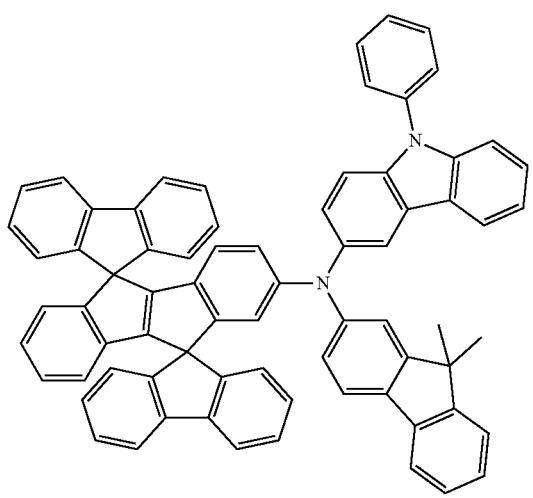
67
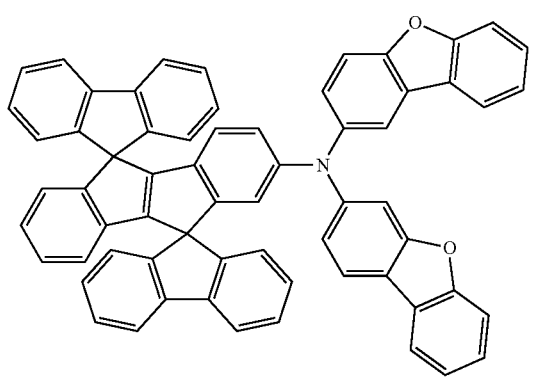

-continued
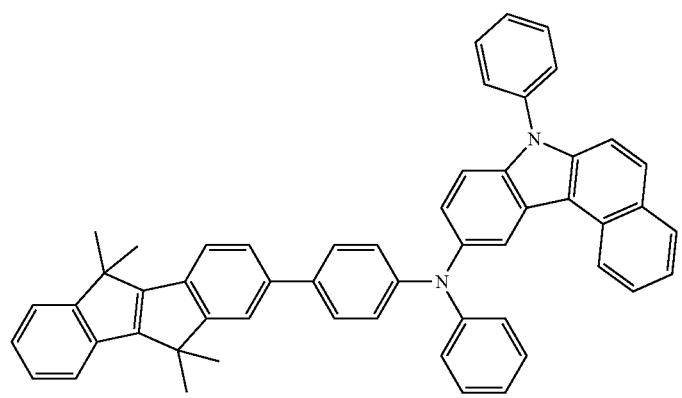
68
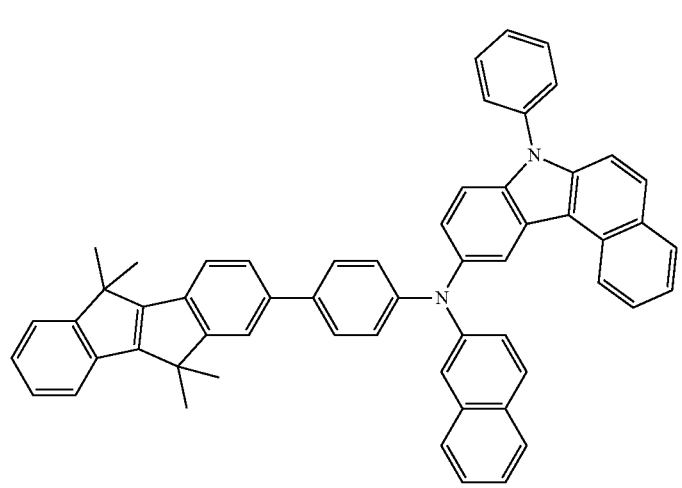
69
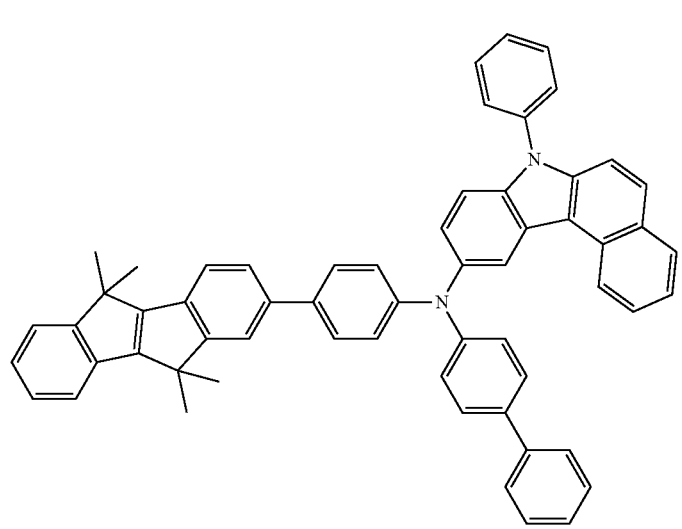
70

71
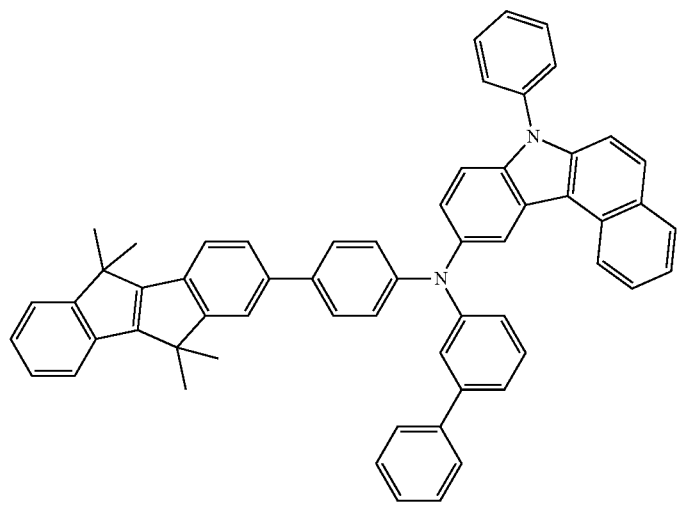
72
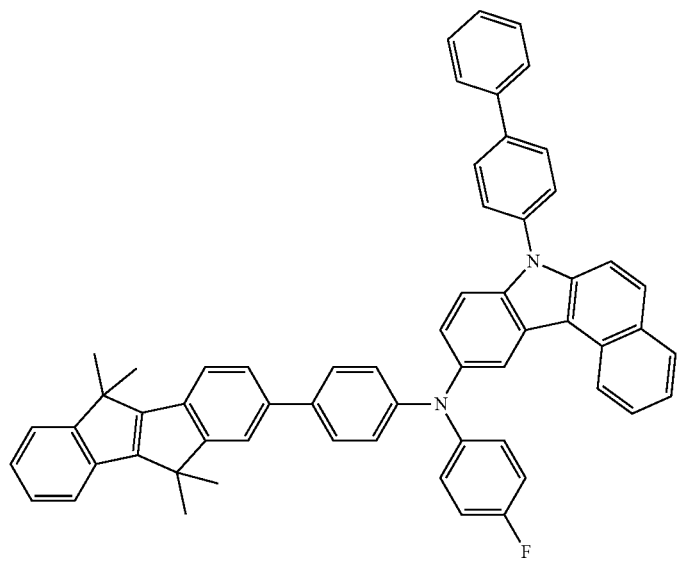
73
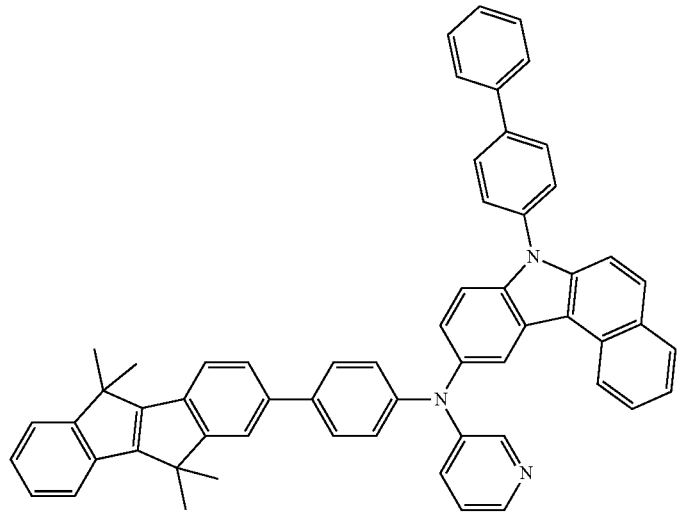

-continued
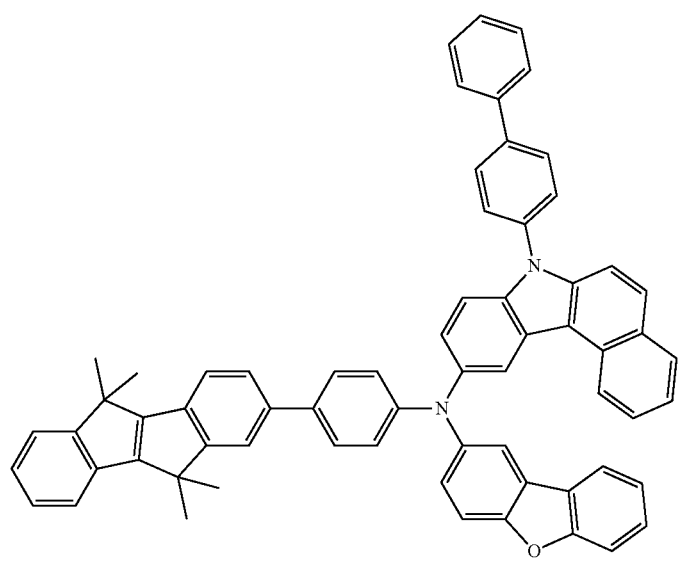
74
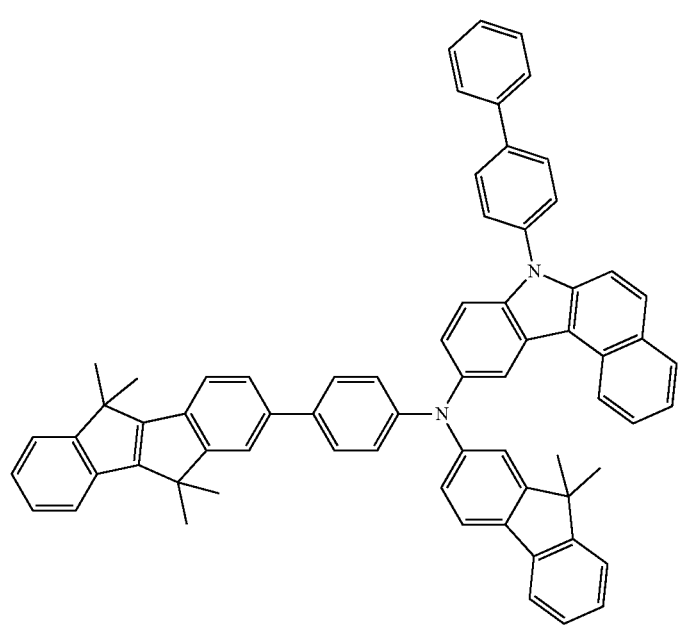
75

-continued
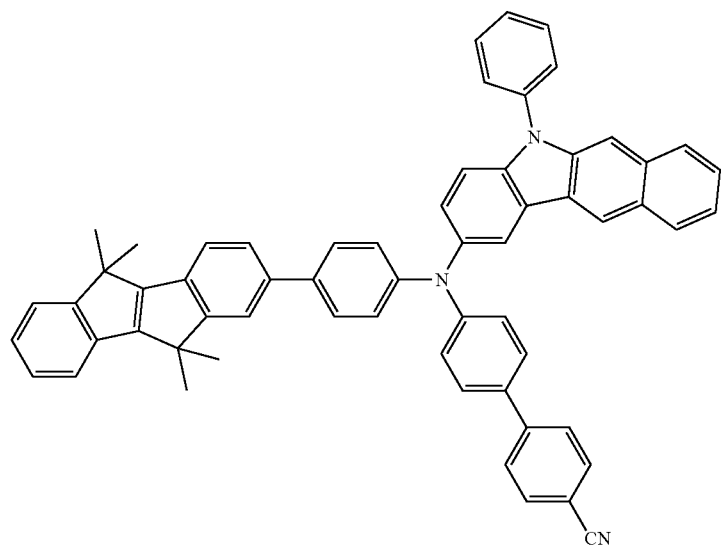
76
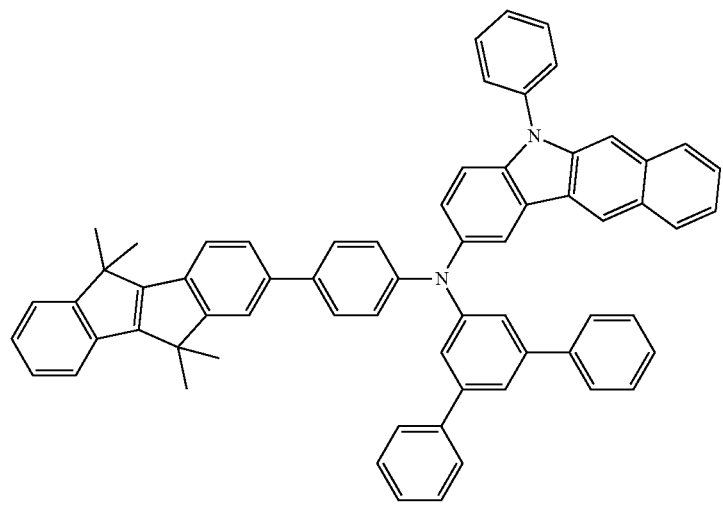
77
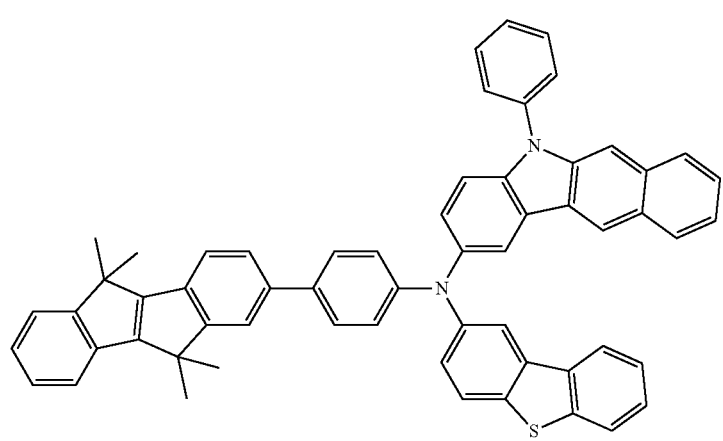
78

-continued
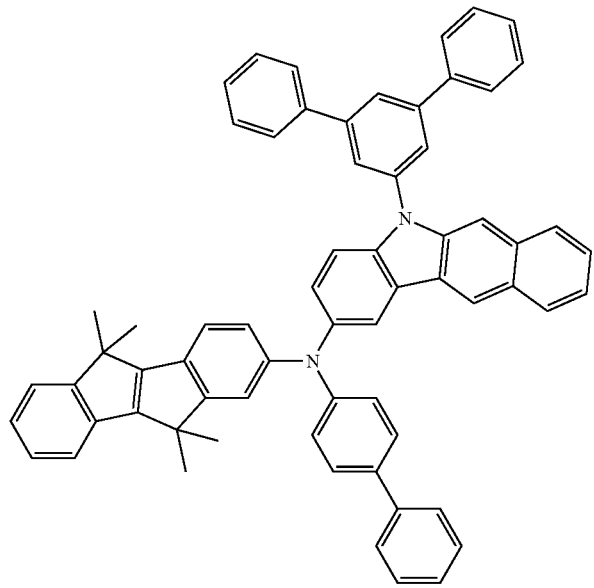
79
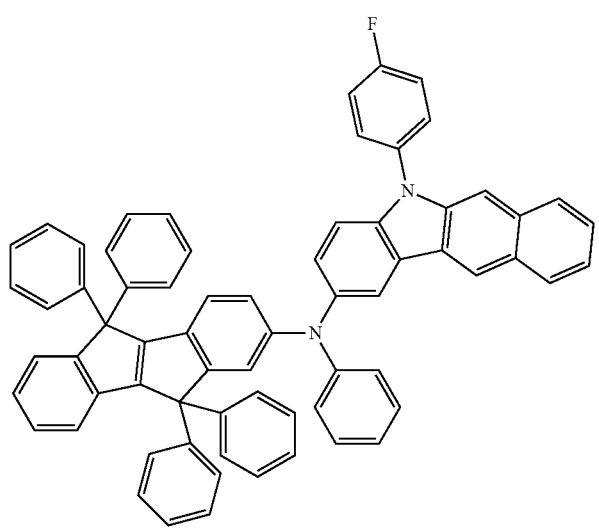
80

-continued

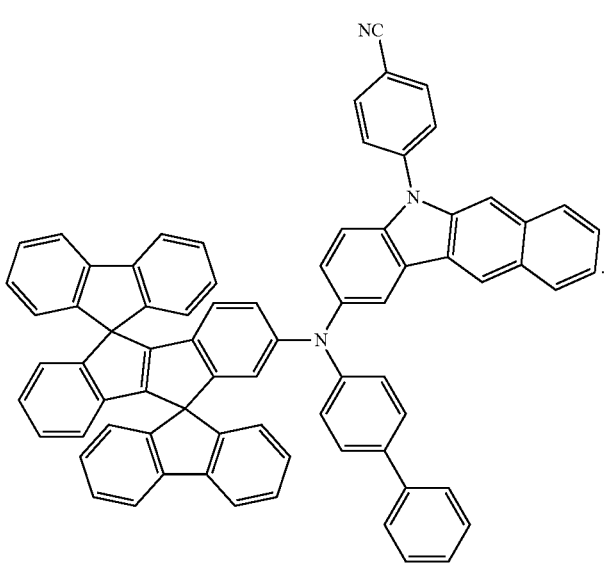
81

13. An organic light-emitting device comprising:
a first electrode;
a second electrode facing the first electrode; and
an organic layer between the first electrode and the second electrode and comprising an emission layer,
wherein the organic layer comprises the compound of claim 1.

14. The organic light-emitting device of claim 13, wherein:
the first electrode is an anode,
the second electrode is a cathode, and
the organic layer comprises:
i) a hole transport region between the first electrode and the emission layer and comprising a hole transport layer and at least one layer selected from a hole injection layer and an electron blocking layer; and
ii) an electron transport region between the emission layer and the second electrode and comprising at least one layer selected from an electron transport layer, a hole blocking layer, and an electron injection layer.

15. The organic light-emitting device of claim 14, wherein the hole transport region comprises the compound of claim 1.

16. The organic light-emitting device of claim 14, wherein the hole transport layer comprises the compound of claim 1.

17. The organic light-emitting device of claim 14, wherein the hole transport region comprises a charge-generating material.

18. The organic light-emitting device of claim 17, wherein the charge-generating material is a p-dopant.

19. The organic light-emitting device of claim 18, wherein the p-dopant is selected from a quinone derivative, a metal oxide, and a compound containing a cyano group.

20. A display device comprising the organic light-emitting device of claim 13, in which a first electrode is electrically connected to a source electrode or a drain electrode of a thin film transistor.

* * * * *